US011549126B2

(12) United States Patent
Gurumurthy et al.

(10) Patent No.: US 11,549,126 B2
(45) Date of Patent: *Jan. 10, 2023

(54) TREATMENT METHODS USING DNA EDITING WITH SINGLE-STRANDED DNA

(71) Applicants: Board of Regents of the University of Nebraska, Lincoln, NE (US); Tokai University Educational System, Hiratsuka (JP)

(72) Inventors: Channabasavaiah B. Gurumurthy, Omaha, NE (US); Hiromi Miura, Kanagawa (JP); Masato Ohtsuka, Kanagawa (JP)

(73) Assignees: BOARD OF REGENTS OF THE UNIVERSITY OF NEBRASKA, Lincoln, NE (US); TOKAI UNIVERSITY EDUCATIONAL SYSTEM, Tokyo (JP)

( * ) Notice: Subject to any disclaimer, the term of this patent is extended or adjusted under 35 U.S.C. 154(b) by 382 days.

This patent is subject to a terminal disclaimer.

(21) Appl. No.: 15/828,979

(22) Filed: Dec. 1, 2017

(65) Prior Publication Data
US 2018/0127787 A1 May 10, 2018

Related U.S. Application Data

(63) Continuation-in-part of application No. PCT/US2016/035660, filed on Jun. 3, 2016.

(60) Provisional application No. 62/170,306, filed on Jun. 3, 2015.

(51) Int. Cl.
*C12N 15/90* (2006.01)
*C12N 15/10* (2006.01)
*A01K 67/027* (2006.01)
*C12N 9/22* (2006.01)
*C12N 15/11* (2006.01)
*C12N 15/85* (2006.01)
*C12N 9/96* (2006.01)

(52) U.S. Cl.
CPC ........ *C12N 15/907* (2013.01); *A01K 67/0275* (2013.01); *A01K 67/0276* (2013.01); *A01K 67/0278* (2013.01); *C12N 9/22* (2013.01); *C12N 9/96* (2013.01); *C12N 15/102* (2013.01); *C12N 15/11* (2013.01); *C12N 15/8509* (2013.01); *A01K 2217/058* (2013.01); *A01K 2217/203* (2013.01); *A01K 2227/105* (2013.01); *C12N 2310/20* (2017.05); *C12N 2510/00* (2013.01)

(58) Field of Classification Search
CPC .................................................. C12N 2310/20
See application file for complete search history.

(56) References Cited

U.S. PATENT DOCUMENTS

| | | | |
|---|---|---|---|
| 5,066,584 A | 11/1991 | Gyllensten et al. | |
| 5,578,709 A | 11/1996 | Woiszwillo | |
| 5,603,960 A | 2/1997 | O'Hagan | |
| 5,723,269 A | 3/1998 | Akagi et al. | |
| 5,871,747 A | 2/1999 | Gengoux-Sedlik et al. | |
| 5,981,719 A | 11/1999 | Woiszwillo et al. | |
| 6,022,564 A | 2/2000 | Takechi et al. | |
| 6,090,925 A | 7/2000 | Woiszwillo et al. | |
| 6,210,707 B1 | 4/2001 | Papahadjopoulos et al. | |
| 6,264,987 B1 | 7/2001 | Wright et al. | |
| 6,309,569 B1 | 10/2001 | Farrar et al. | |
| 6,379,704 B2 | 4/2002 | Wright et al. | |
| 6,528,087 B2 | 3/2003 | Papahadjopoulos et al. | |
| 6,534,092 B2 | 3/2003 | Wright et al. | |
| 6,565,777 B2 | 5/2003 | Farrar et al. | |
| 6,884,435 B1 | 4/2005 | O'Hagan et al. | |
| 6,913,767 B1 | 7/2005 | Cleland et al. | |
| 7,396,664 B2 | 7/2008 | Daly et al. | |
| 8,252,324 B2 | 8/2012 | Petrenko | |
| 8,697,359 B1 | 4/2014 | Zhang | |
| 8,735,067 B2 | 5/2014 | Zhang et al. | |
| 8,895,308 B1 | 11/2014 | Zhang et al. | |
| 8,932,814 B2 | 1/2015 | Cong et al. | |
| 8,993,233 B2 | 3/2015 | Zhang et al. | |
| 9,637,739 B2 | 5/2017 | Sikšnys et al. | |
| 2005/0106594 A1* | 5/2005 | Ellington .............. | C12N 15/111 435/6.11 |
| 2007/0081972 A1 | 4/2007 | Sandler et al. | |
| 2007/0160581 A1 | 7/2007 | Conrad et al. | |
| 2010/0267093 A1 | 10/2010 | Court et al. | |
| 2011/0165630 A1* | 7/2011 | Maresca ............. | C12N 15/1082 435/91.53 |
| 2013/0137180 A1 | 5/2013 | Chen et al. | |
| 2013/0326645 A1 | 12/2013 | Cost et al. | |
| 2014/0066388 A1 | 3/2014 | Anderson et al. | |
| 2014/0068797 A1* | 3/2014 | Doudna ................. | C12N 15/63 800/18 |
| 2014/0113375 A1* | 4/2014 | Liu ...................... | C12N 15/102 435/462 |

(Continued)

FOREIGN PATENT DOCUMENTS

| | | |
|---|---|---|
| CN | 104195177 | 12/2014 |
| WO | WO 2012/012738 | 1/2012 |

(Continued)

OTHER PUBLICATIONS

Kunzelmann et al. (1996) Gene targeting of CFTR DNA in CF epithelial cells. Gene Therapy, 3:859-867 (Year: 1996).*

(Continued)

Primary Examiner — Lora E Barnhart Driscoll
Assistant Examiner — Catherine Konopka
(74) Attorney, Agent, or Firm — Quarles & Brady LLP

(57) ABSTRACT

Disclosed are compositions, methods, and kits for modifying DNA within cells as well as compositions and methods for modifying gene expression in a cell. In particular, the invention generally relates to compositions, methods, and kits for DNA editing using single-stranded DNA. Compositions and methods for modifying gene expression using artificial microRNAs (amiRNA) are also contemplated.

19 Claims, 22 Drawing Sheets

Specification includes a Sequence Listing.

(56) References Cited

U.S. PATENT DOCUMENTS

| | | |
|---|---|---|
| 2014/0170753 A1 | 6/2014 | Zhang |
| 2014/0179770 A1 | 6/2014 | Zhang et al. |
| 2014/0186843 A1 | 7/2014 | Zhang et al. |
| 2014/0186919 A1 | 7/2014 | Zhang et al. |
| 2014/0189896 A1 | 7/2014 | Zhang et al. |
| 2014/0234972 A1 | 8/2014 | Zhang et al. |
| 2014/0242664 A1 | 8/2014 | Zhang et al. |
| 2014/0242699 A1 | 8/2014 | Zhang |
| 2014/0242702 A1 | 8/2014 | Chen et al. |
| 2014/0273233 A1 | 9/2014 | Chen et al. |
| 2014/0287938 A1 | 9/2014 | Zhang et al. |
| 2014/0294773 A1 | 10/2014 | Brouns et al. |
| 2014/0310830 A1 | 10/2014 | Zhang et al. |
| 2014/0357530 A1 | 12/2014 | Zhang et al. |
| 2014/0359795 A1 | 12/2014 | Fahrenkrug et al. |
| 2014/0359796 A1 | 12/2014 | Fahrenkrug et al. |
| 2015/0031133 A1 | 1/2015 | Church et al. |
| 2015/0059010 A1 | 2/2015 | Cigan et al. |
| 2015/0232883 A1 | 8/2015 | Dahlman et al. |
| 2015/0284727 A1 | 10/2015 | Kim et al. |
| 2016/0017366 A1 | 1/2016 | Chen et al. |

FOREIGN PATENT DOCUMENTS

| | | | |
|---|---|---|---|
| WO | WO-2012012738 A1 * | 1/2012 | ........... C12N 15/907 |
| WO | WO2012/115806 | 8/2012 | |
| WO | WO2012/054425 | 9/2012 | |
| WO | WO2013/176772 | 11/2013 | |
| WO | WO2013/191769 | 12/2013 | |
| WO | WO2014/093595 | 6/2014 | |
| WO | WO2014/093635 | 6/2014 | |
| WO | WO2014/093701 | 6/2014 | |
| WO | WO2014/144951 | 9/2014 | |
| WO | WO2014/150624 | 9/2014 | |
| WO | WO2014/172458 | 10/2014 | |
| WO | WO2014/204726 | 12/2014 | |
| WO | WO2015/030881 | 3/2015 | |
| WO | WO2015/089351 | 6/2015 | |
| WO | WO2016/196887 | 12/2016 | |

OTHER PUBLICATIONS

Naldini, L. (2011) Ex vivo gene transfer and correction for cell-based therapies. Nature Reviews Genetics, 12:301-315 (Year: 2011).*
Qin et al. (2015) Efficient CRISPR/Cas9-Mediated Genome Editing in Mice by Zygote Electroporation of Nuclease. Genetics, 200: 423-430 (Year: 2015).*
SuperScript III First-Strand Synthesis System for RT-PCR (Invitrogen, 2003, Cat. No. 18080-051, 4 pages) (Year: 2003).*
Cong et al., (2013) Multiplex Genome Engineering Using CRISPR/Cas Systems. Science, 339:819-823 (Year: 2013).*
Epicentre (AmpliScribe™ T7 High Yield Transcription Kit, Epicentre Technologies, An Illumina Company, Lit. # 040 (Year: 2012).*
Sun, M. et al., "CRISPR/Cas9 Genome Editing System in Drosophila," Advanced Techniques in Biology and Medicine. 2015, S1: 003 doi: 10.4172/2379-1764.
Article entitled Easi-CRISPR: thanks to a new method, gene editing becomes much easier.
Article entitled "Best of 2017: Top Picks from Genome Biology".
Hu, T. et al., "Comparative Studies of Various Artificial microRNA Expression Vectors for RNAi in Mammalian Cells" 2010 Mol Biotechnol 46:34-40.
Supplementary European Search Report and Opinion dated Oct. 2, 2018 for European Application No. 16804495.6.
Aida et al., Gene cassette knock-in in mammalian cells and zygotes by enhanced MMEJ. BMC Genomics. 2016;17. doi:10.1186/s12864-016-3331-9.
Banan, M. "Recent advances in CRISPR/Cas9-mediated knock-ins in mammalian cells." Journal of biotechnology 308 (2020): 1-9.
Bishop Ka, et al. CRISPR/Cas9-mediated insertion of loxP sites in the mouse Dock7 gene provides an effective alternative to use of targeted embryonic stem cells. G3 Bethesda Md. 2016;6:2051-61.
Bollen, Y., et al. "How to create state-of-the-art genetic model systems: strategies for optimal CRISPR-mediated genome editing." Nucleic acids research 46.13 (2018): 6435-6454.
Burgio, G. "Redefining mouse transgenesis with CRISPR/Cas9 genome editing technology." Genome biology 19.1 (2018): 1-3.
Cohen, "Any idiot can do it." Genome editor CRISPR could put mutant mice in everyone's reach, Nov. 3, 2016.
Flemr M, et al. Single-step generation of conditional knockout mouse embryonic stem cells. Cell Rep. 2015;12:709-16.
Fontaine Da, et al. Attention to background strain is essential for metabolic research: C57BL/6 and the International Knockout Mouse Consortium. Diabetes. 2016;65:25-33.
Gu et al. 2011. The role of Tet3 DNA dioxygenase in epigenetic reprogramming by oocytes. Nature 477 606-610.
He, X. et al. "New turns for high efficiency knock-in of large DNA in human pluripotent stem cells." Stem cells International 2018 (2018).
Ison Jr, et al. Age-related hearing loss in C57BL/6 J mice has both frequency-specific and non-frequency-specific components that produce a hyperacusis-like exaggeration of the acoustic startle reflex. J Assoc Res Otolaryngol. 2007;8:539-50.
Lee Ay, et al. Conditional targeting of Ispd using paired Cas9 nickase and a single DNA template in mice. FEBS Open Bio. 2014;4:637-42.
Li, H. et al., Design and specificity of long ssDNA donors for CRISPR-based knock-in, bioRxiv, Aug. 21, 2017, pp. 1-24.
Ma Y, et al. Generating rats with conditional alleles using CRISPR/Cas9. Cell Res. 2014;24:122-5.
Miano Jm, et al. A CRISPR path to engineering new genetic mouse models for cardiovascular research. Arterioscler Thromb Vase Biol. 2016;36:1058-75.
Miura et al., Easi-CRISPR for creating knock-in and conditional knockout mouse models using long ssDNA donors, Nat. Protoc. Jan. 2018; 13(1):195-215.
Murgha et al., Combined in vitgro transcription and reverse transcription to amplify and label complex synthetic oligonucleotide probe libraries. BioTechniques 58:301-307. (Jun. 2015).
Oji A, et al. CRISPR/Cas9 mediated genome editing in ES cells and its application for chimeric analysis in mice. Sci Rep. 2016;6:31666.
Paix, A, et. al, Precision genome editing using synthesis-dependent repair of Cas9-induced DNA breaks, PNAS, Nov. 28, 2017, pp. E10745-E10754.
Rajewsky K, et al. Conditional gene targeting. J Clin Invest. 1996;98:600-3.
Roth, T. I., et. al., Reprogramming human T cell function and specificity with non-viral genome targeting, Nature, vol. 559, Jul. 19, 2019.
Ryu, S.-M., et al. "Evolution of CRISPR towards accurate and efficient mammal genome engineering." BMB reports 52.8 (2019): 475.
Skarnes Wc, et al. A conditional knockout resource for the genome-wide study of mouse gene function. Nature. 2011;474:337-42.
Superscript III First-Strand Synthesis System for RT-=PCR (Invitrogen, 2003, Cat. No. 18080-051, 4 pages).
Wang et al. Highly efficient CRISPR/HDR-mediated knock-in for mouse embryonic stem cells and zygotes. BioTechniques. 2015;59. doi:10.2144/000114339.
Yamamoto, Y. et al. "Making ends meet: targeted integration of DNA fragments by genome editing." Chromosoma 127.4 (2018): 405-420.
Yang H, et al. One-step generation of mice carrying reporter and conditional alleles by CRISPR/Cas-mediated genome engineering. Cell. 2013;154:1370-9.
Zhu, F., et al. "Humanising the mouse genome piece by piece." Nature communications 10.1 (2019): 1-13.
Beby, F. et al.,"The homeobox gene Otx2 in development and disease," Exp Eye Res 2013, 111:9-16.
Bernard, C. et al., "Graded Otx2 activities demonstrate dose-sensitive eye and retina phenotypes," Hum Mol Genet 2014, 23:1742-1753.
Bharali, D.J. et al., "Nanoparticles and cancer therapy: A concise review with emphasis on dendrimers," International Journal of Nanomedicine 2009, 4:1-7.

(56) References Cited

OTHER PUBLICATIONS

Burge, C. et al., "Prediction of complete gene structures in human genomic DNA," J Mol Biol 1997, 268:78-94.
Carlson, D.F. et al., "Targeting DNA With Fingers and TALENs," Molecular Therapy Nucleic Acids 2012, 1(1):e3.
Chen, F. et al., "High-frequency genome editing using ssDNA oligonucleotides with zinc-finger nucleases," Nat Methods 2011, 8(9):753-5.
Chu, V.T. et al., "Increasing the efficiency of homology-directed repair for CRISPR-Cas9-induced precise gene editing in mammalian cells," Nat Biotechnol. 2015, 33(5):543-8.
Cismaru et al., "Polymeric Nanoparticles with Biomedical Applications," Rev. Roum. Chim., 2010, 55(8):433-442.
Le Cong et al., "Multiplex Genome Engineering Using CRISPR/Cas Systems," Science 2013, 339(6121):819-823.
Esfand, R. et al., "Poly(amidoamine) (PAMAM) dendrimers: from biomimicry to drug delivery and biomedical applications," Drug Discov. Today 2001, 6(8):427-436.
Gaj, T. et al., "ZHN, TALEN, and CRISPR/Cas-based methods for genome engineering," Trends in Biotechnology 2013, 31(7):397-405.
Gao, F. et al., "DNA-guided genome editing using the Natronobacterium gregoryi Argonaute," Nature Biotechnology 2016, 34:768-773.
Fisher, E.M. et al., "New approaches for modelling sporadic genetic disease in the mouse," Dis Model Mech 2009, 2:446-453.
Fossat, N. et al., "Temporal and spatial delineation of mouse Otx2 functions by conditional self-knockout," EMBO Rep 2006, 7:824-830.
Harms, D.W. et al., "Mouse Genome Editing Using the CRISPR/Cas System," Curr Protoc Hum Genet 2014, 83:15.
Hasuwa, H. et al., "Small interfering RNA and gene silencing in transgenic mice and rats," FEBS Lett 2002, 532:227-230.
Hickman-Davis, J.M. et al., "Transgenic mice," Paediatr Respir Rev 2006, 7:49-53.
Hide, T. et al., "Genetic modifiers of otocephalic phenotypes in Otx2 heterozygous mutant mice," Development 2002, 129:4347 4357.
Horii, T. et al., "Challenges to increasing targeting efficiency in genome engineering," J Reprod Dev. 2016, 62(1):7-9.
Inui, M. et al., "Rapid generation of mouse models with defined point mutations by the CRISPR/Cas9 system," Sci Rep 2014, 5396.
Kleinhammer, A. et al., "Gene knockdown in the mouse through RNAi," Methods Enzymol 2010, 477:387-414.
Kouadjo, K.E. et al., "Housekeeping and tissue-specific genes in mouse tissues," BMC Genomics 2007, 8:127.
Kumari, A. et al., "Biodegradable polymeric nanoparticles based drug delivery systems," Colloids and Surfaces B: Biointerfaces 2010, 75:1-18.
Lin, S. et al., "Enhanced homology-directed human genome engineering by controlled timing of CRISPR/Cas9 delivery," eLife 2014, 3:e04766.
Liu, D. et al., "Dosage-dependent requirement of BMP type II receptor for maintenance of vascular integrity," Blood 2007, 110:1502-1510.
Mali, P. et al., "RNA-guided human genome engineering via Cas9," Science 2013, 339(6121): 823-826.
Maruyama, T. et al., "Increasing the efficiency of precise genome editing with CRISPR-Cas9 by inhibition of nonhomologous end joining," Nat Biotechnol. 2015, 33(5):538-42.
Matsuo, I. et al., "Mouse Otx2 functions in the formation and patterning of rostral head," Genes Dev 1995, 9:2646-2658.
Miura, H. et al., "CRISPR/Cas9-based generation of knockdown mice by intronic insertion of artificial microRNA using longer single-stranded DNA," Sci Rep. 2015, 5:12799.
Miura, H. et al., "Assessment of Artificial MiRNA Architectures for Higher Knockdown Efficiencies without the Undesired Effects in Mice," PLoS One 2015, 10:1-17.
Montague, T.G. et al., "CHOPCHOP: a CRISPR/Cas9 and TALEN web tool for genome editing," Nucleic Acids Res 2014, 42:W401-407.
Moreira, J.N. et al., "Use of the Post-Insertion Technique to Insert Peptide Ligands into Pre-Formed Stealth Liposomes with Retention of Binding Activity and Cytotoxicity," Pharm. Res. 2002, 19:265-269.
Moreno-Maldonado, R. et al., "RNAi-mediated knockdown of IKK1 in transgenic mice using a transgenic construct containing the human H1 promoter," ScientificWorldJournal 2014, 193803.
Mutsaers, A.J. et al., "Modeling distinct osteosarcoma subtypes in vivo using Cre:lox and lineage-restricted transgenic shRNA," Bone 2013, 55:166-178.
Nagavarma, B.N. et al., "Different Techniques for Preparation of polymeric Nanoparticles," Asian J. of Pharma. and Clin. Res. 2012, 5(3):16-23.
Nakade, S. et al., "Microhomology-mediated end-joining-dependent integration of donor DNA in cells and animals using TALENs and CRISPR/Cas9," Nat Commun. 2014, 5:5560.
Nakao, H. et al., "A possible aid in targeted insertion of large DNA elements by CRISPR/Cas in mouse zygotes," Genes 2016, N Y N 2000.
Oberdoerffer, P. et al., "Unidirectional Cre-mediated genetic inversion in mice using the mutant loxP pair lox66/lox71," Nucleic Acids Res 2003, 31:e140.
Ohtsuka, M. et al., "Pronuclear injection-based mouse targeted transgenesis for reproducible and highly efficient transgene expression," Nucleic Acids Res 2010, 38:e198.
Ohtsuka, M. et al., "Fluorescent transgenic mice suitable for multi-color aggregation chimera studies," Cell Tissue Res 2012, 350:251-260.
O'Shaughnessy, J.A. et al., "Pegylated liposomal doxorubicin in the treatment of breast cancer," Clin. Breast cancer 2003, 4:318-328.
Podolska, K. et al., "Targeting genes in living mammals by RNA interference," Brief Funct Genomics 2011, 10:238-247.
Premsrirut, P.K. et al., "A rapid and scalable system for studying gene function in mice using conditional RNA interference," Cell 2011, 145:145-158.
Qiu, L. et al., "A construct with fluorescent indicators for conditional expression of miRNA," BMC Biotechnol 2008, 8:77.
Quadros, R.M. et al., "Insertion of sequences at the original provirus integration site of mouse ROSA26 locus using the CRISPR/Cas9 system," FEBS Open Bio 2015, 5:191-197.
Quadros, R.M. et al., "Easi-CRISPR: a robust method for one-step generation of mice carrying conditional and insertion alleles using long ssDNA donors and CRISPR ribonucleoproteins," Genome Biology 2017, 18:92.
Ran, F.A. et al., "Genome engineering using the CRISPR-Cas9 system," Nat Protoc 2013, 8:2281-2308.
Reis, C.P. et al., "Nanoencapsulation I. Methods for preparation of drug-loaded polymeric nanoparticles," Nanomedicine 2006, 2(I):8-21.
Richardson, C.D. et al., "Enhancing homology-directed genome editing by catalytically active and inactive CRISPR-Cas9 using asymmetric donor DNA," Nat Biotechnol. 2016, 34(3):339-44.
Sakuma, T. et al., "MMEJ-assisted gene knock-in using TALENs and CRISPR-Cas9 with the PITCh systems," Nat Protoc. 2016, 11(1):118-33.
Sarnova, L. et al., "Shortcomings of short hairpin RNA-based transgenic RNA interference in mouse oocytes," J Negat Results Biomed 2010, 9:8.
Sato, M. et al., "Generation of $\alpha$-1,3-Galactosyltransferase-Deficient Porcine Embryonic Fibroblasts by CRISPR/Cas9-Mediated Knock-in of a Small Mutated Sequence and a Targeted Toxin-Based Selection System," Reprod Domest Anim 2015, 50(5):872-80.
Seibler, J. et al., "Single copy shRNA configuration for ubiquitous gene knockdown in mice," Nucleic Acids Res 2005, 33:e67.
Seruggia, D. et al., "The new CRISPR-Cas system: RNA-guided genome engineering to efficiently produce any desired genetic alteration in animals," Transgenic Res 2014, 23: 707-716.
Shen, B. et al., "Efficient genome modification by CRISPR-Cas9 nickase with minimal off-target effects," Nat Methods 2014, 11:399-402.

(56) References Cited

OTHER PUBLICATIONS

Shmakov, S. et al., "Discovery and Functional Characterization of Diverse Class 2 CRISPR-Cas Systems," Molecular Cell 2015, 60:1-13.

Singh, P. et al., "A Mouse Geneticist's Practical Guide to CRISPR Applications," Genetics 2015, 199:1-15.

Soldner, F. et al., "Generation of isogenic pluripotent stem cells differing exclusively at two early onset Parkinson point mutations," Cell 2011, 146(2):318-31.

Stern, P. et al., "A system for Cre-regulated RNA interference in vivo," Proc Natl Acad Sci USA 2008, 105:13895-13900.

Su, X. et al., "In vitro and in vivo mRNA delivery using lipid-enveloped pH-responsive polymer nanoparticles," Molecular Pharmaceutics 2011, 8(3):774-787.

Takahashi, G. et al., "GONAD: Genome-editing via Oviductal Nucleic Acids Delivery system: a novel microinjection independent genome engineering method in mice," Sci. Reports 2015, 5:11406.

Tatiana, A. et al., "Blast 2 sequences—a new tool for comparing protein and nucleotide sequences," FEMS Microbiol Lett. 1999, 174:247-250.

Thomson, J.G. et al., "Mutational analysis of loxP sites for efficient Cre-mediated insertion into genomic DNA," Genesis 2003, 36:162-167.

Torchilin, V.P. et al., "Recent advances with liposomes as pharmaceutical carriers," Nat. Rev. Drug Discov. 2005, 4:145-160.

Van Schendel, R. et al., "Polymerase Θ is a key driver of genome evolution and of CRISPR/Cas9-mediated mutagenesis," Nat Commun. 2015, 6:7394.

Xiong, X. et al., "Intracellular delivery of doxorubicin with RGD-modified sterically stabilized liposomes for an improved antitumor efficacy: In vitro and in vivo," J. Pharm. Sci. 2005, 94:1782-1793.

Yang, H. et al., "Generating genetically modified mice using CRISPR/Cas-mediated genome engineering," Nat Protoc 2014, 9:1956-1968.

Yang, D. et al., "Enrichment of G2/M cell cycle phase in human pluripotent stem cells enhances HDR-mediated gene repair with customizable endonucleases," Sci Rep. 2016, 6:21264.

Yoshimi, K. et al., "ssODN-mediated knock-in with CRISPR-Cas for large genomic regions in zygotes," Nat Commun. 2016, 7:10431.

Yuan, Y. et al., "Single-stranded DNA oligomers stimulate error-prone alternative repair of DNA double-strand breaks through hijacking Ku protein," Nucleic Acids Res. 2015, 43(21):10264-10276.

International Search Report and Written Opinion for PCT/US2016/035660, dated Sep. 19, 2016.

\* cited by examiner

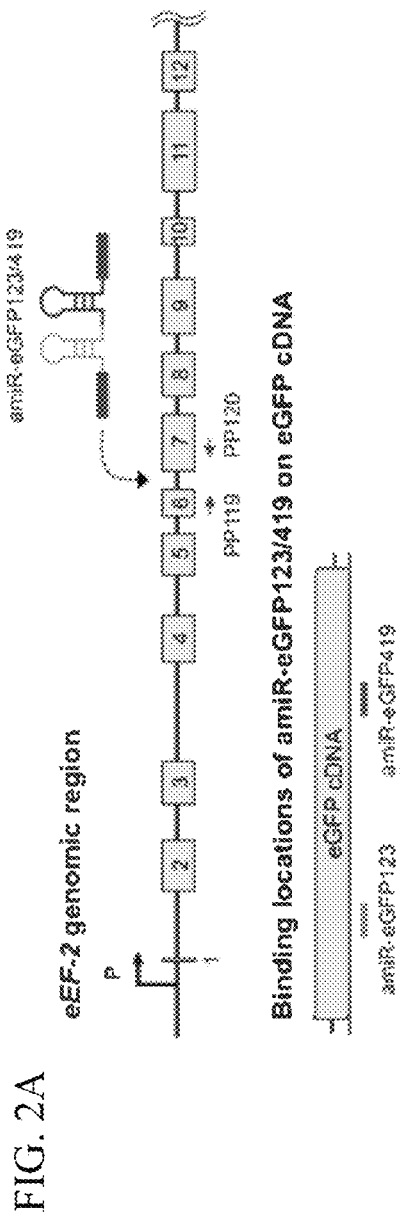
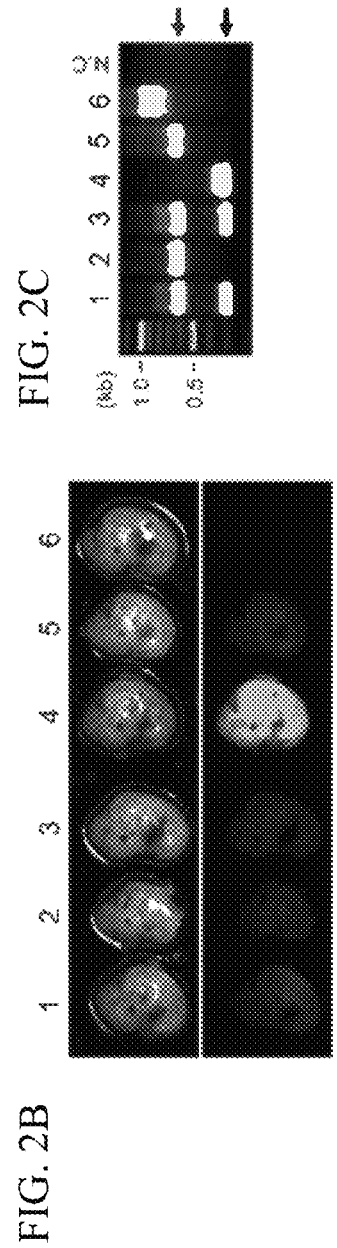
FIG. 2A
FIG. 2B
FIG. 2C
FIG. 2D

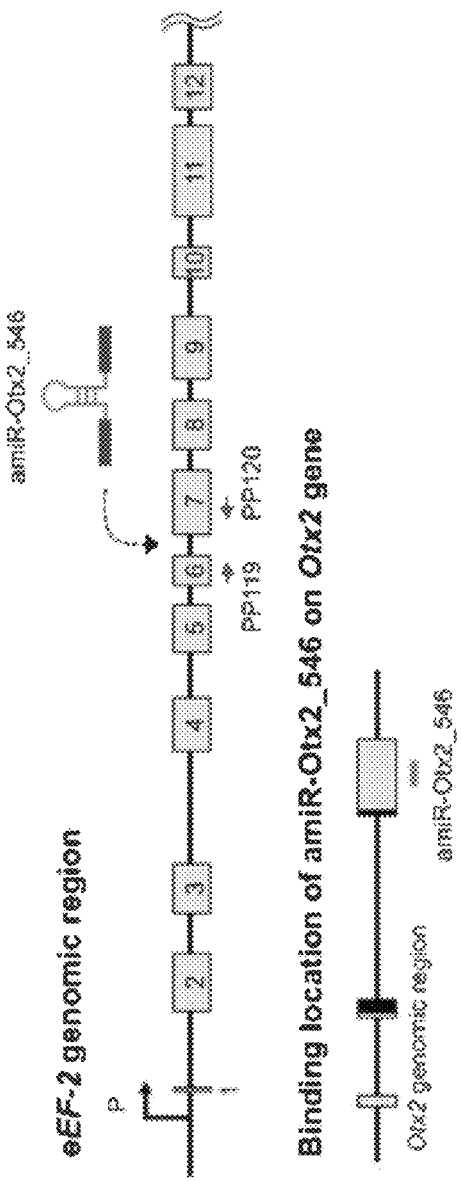
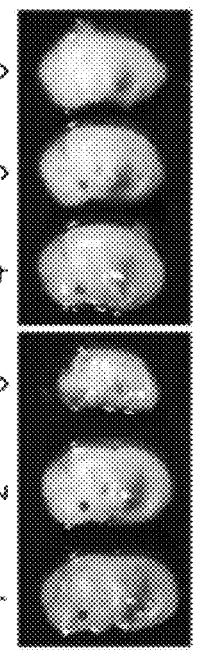
FIG. 3A
FIG. 3B
FIG. 3C
FIG. 3D

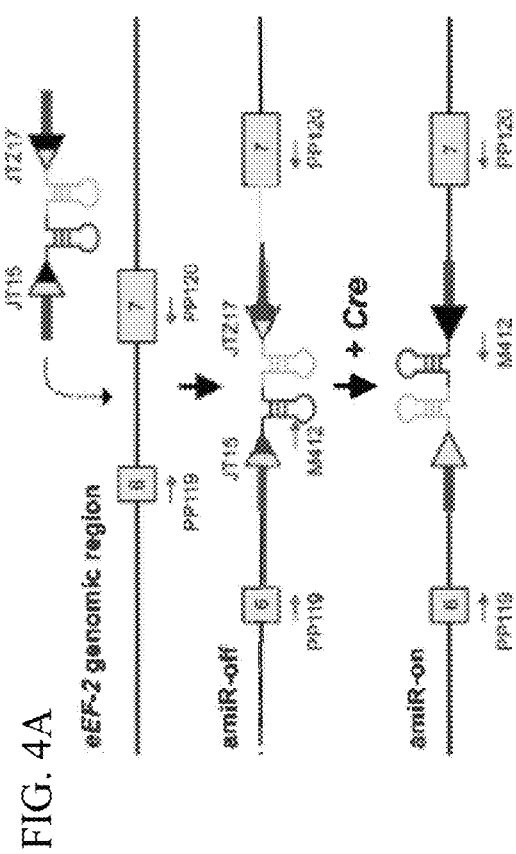
FIG. 4A
FIG. 4B
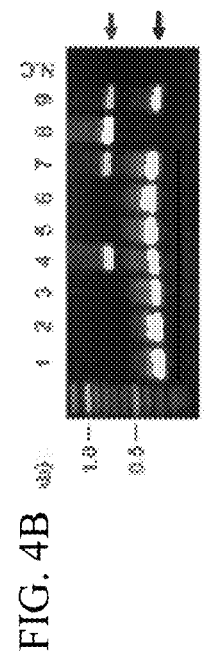
FIG. 4C
| Exp. No. | CRISPR target site | Target for knockdown | Embryos injected | Embryos recovered | Embryos with targeted insertion (%) |
|---|---|---|---|---|---|
| 5 | 6th intron of eEF-2 (TS2) | eGFP | 80 | 9 | 4 (44.4%) |

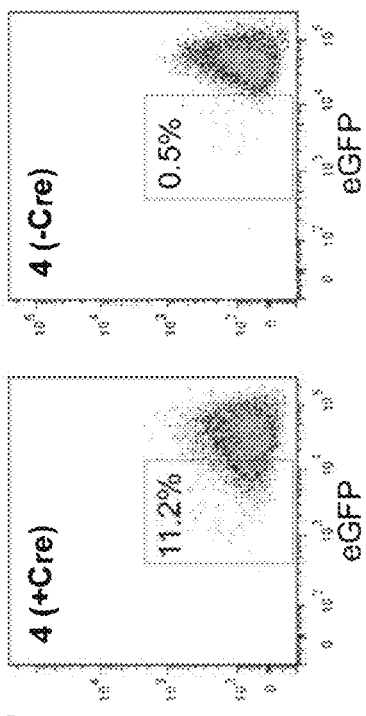
FIG. 4D
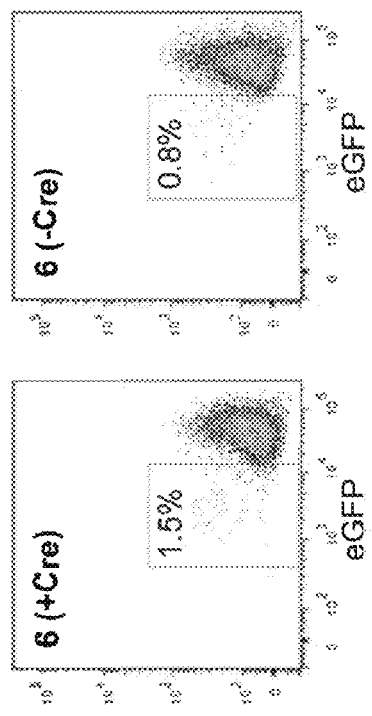
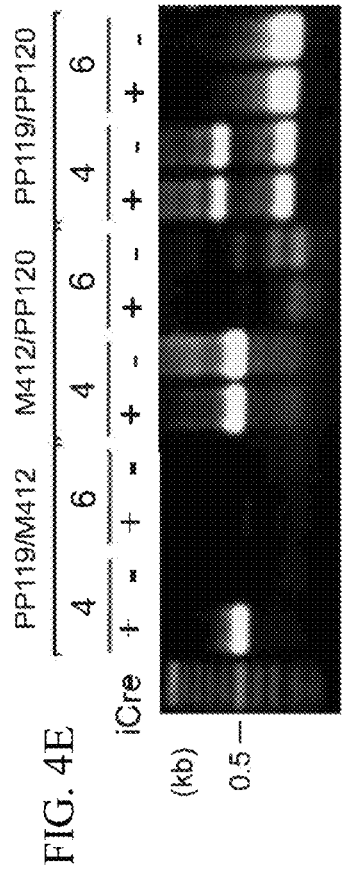
FIG. 4E

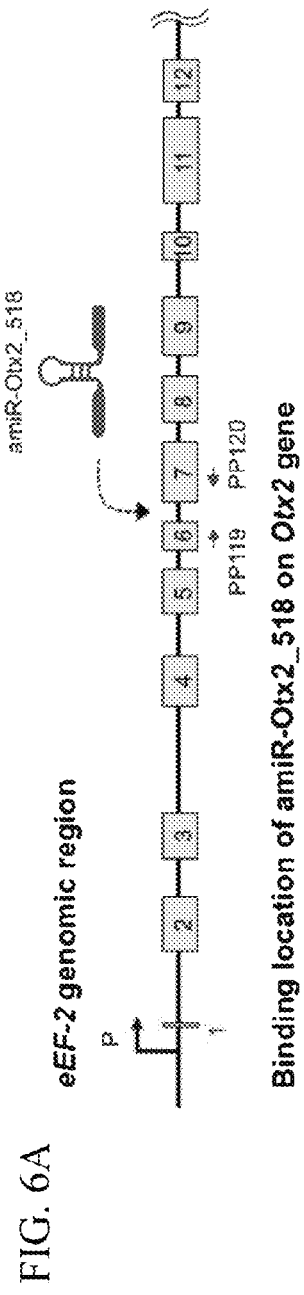
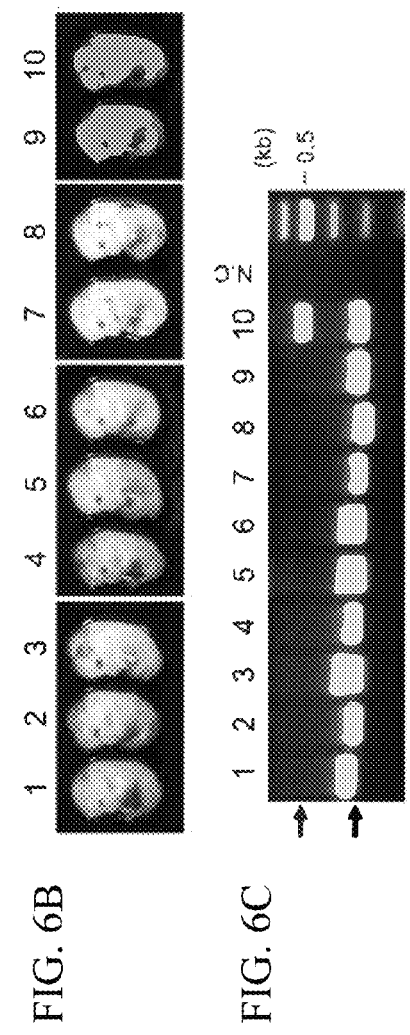
FIG. 6A
FIG. 6B
FIG. 6C
FIG. 6D

FIG. 7A
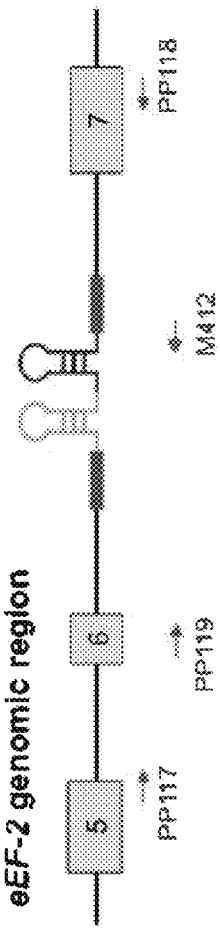
FIG. 7B
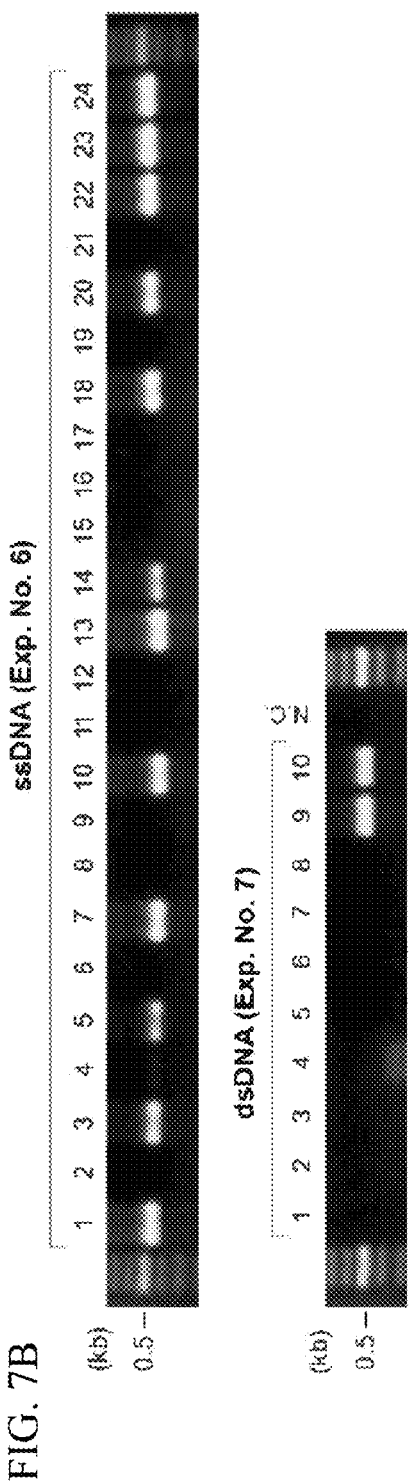
FIG. 7C

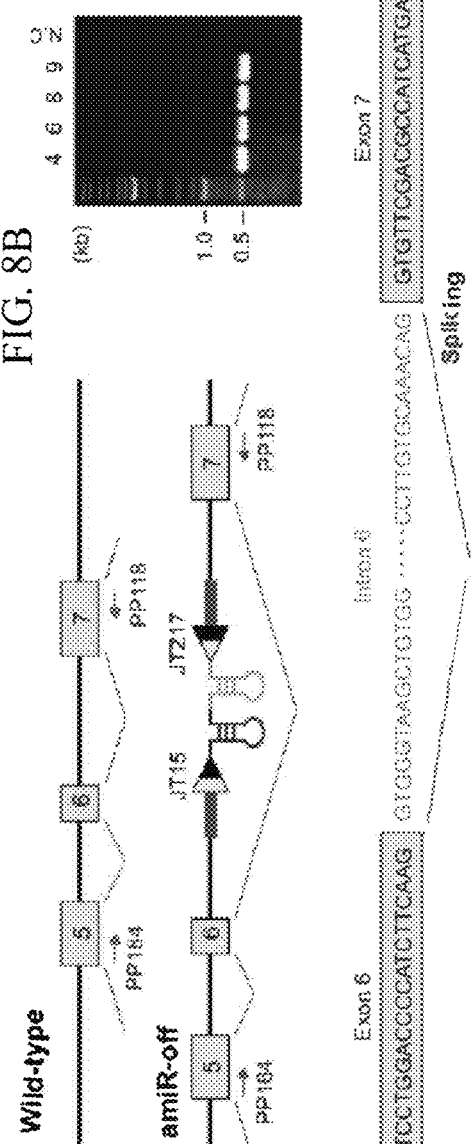

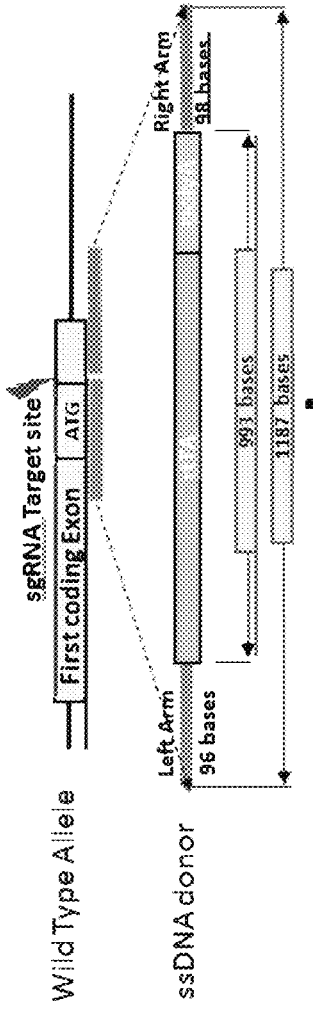
FIG. 11A
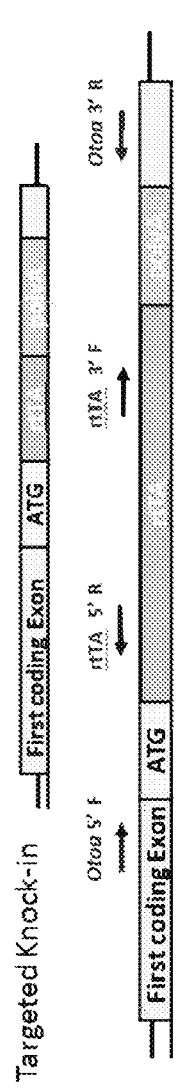
FIG. 11C
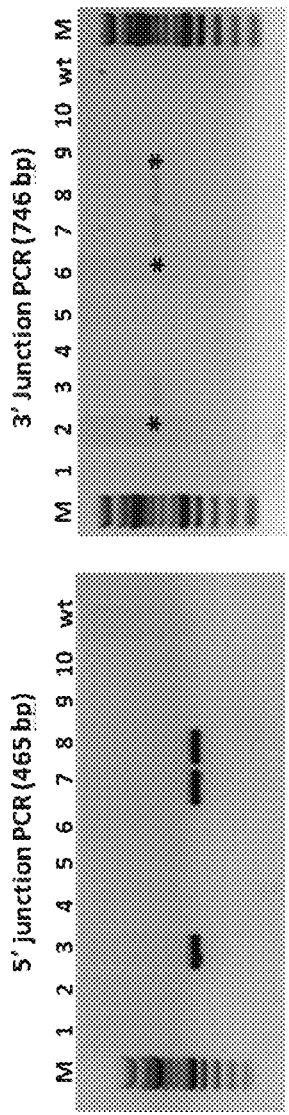
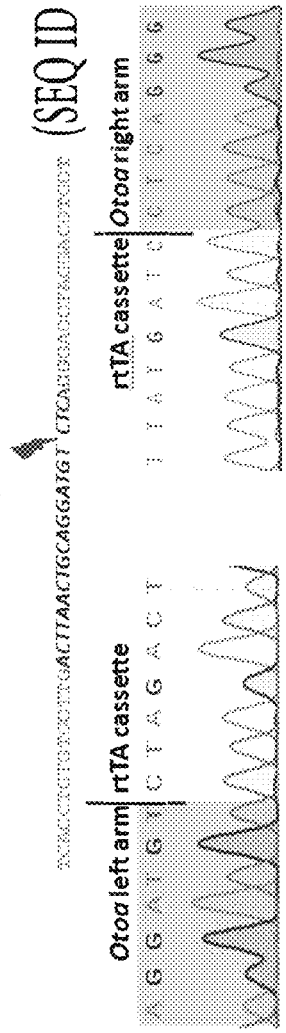
FIG. 11E

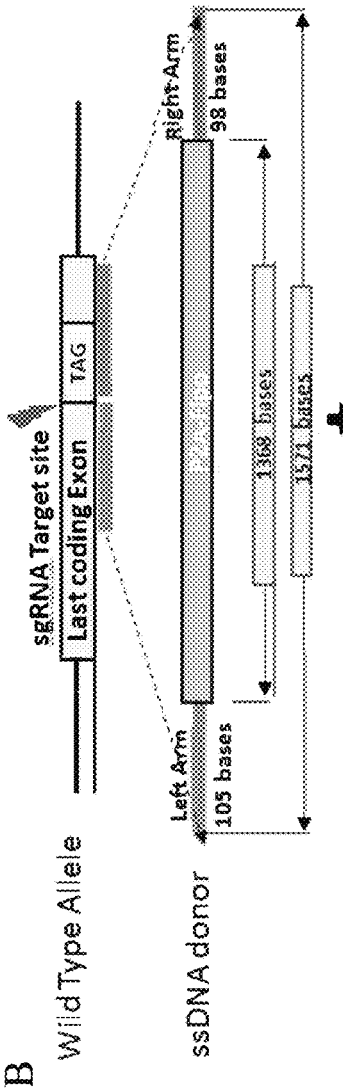
FIG. 11B
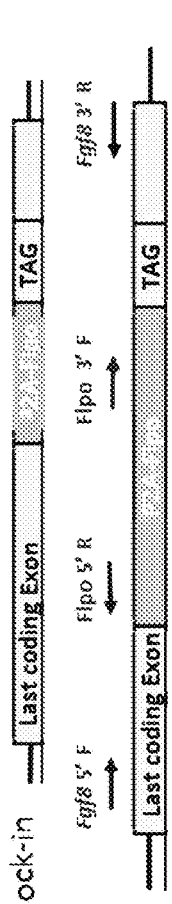
FIG. 11D
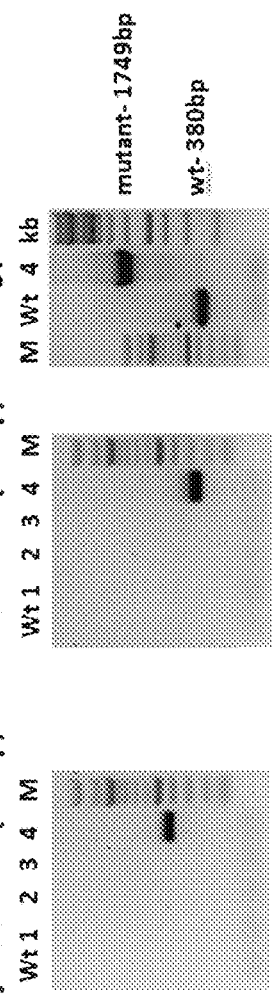
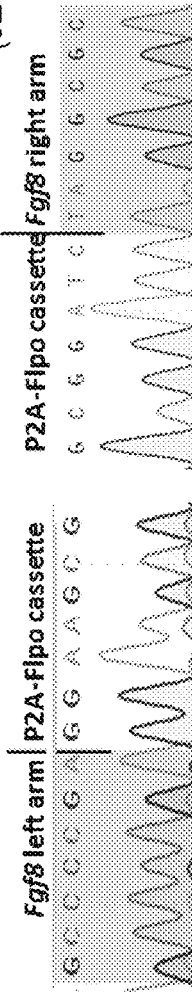
FIG. 11F

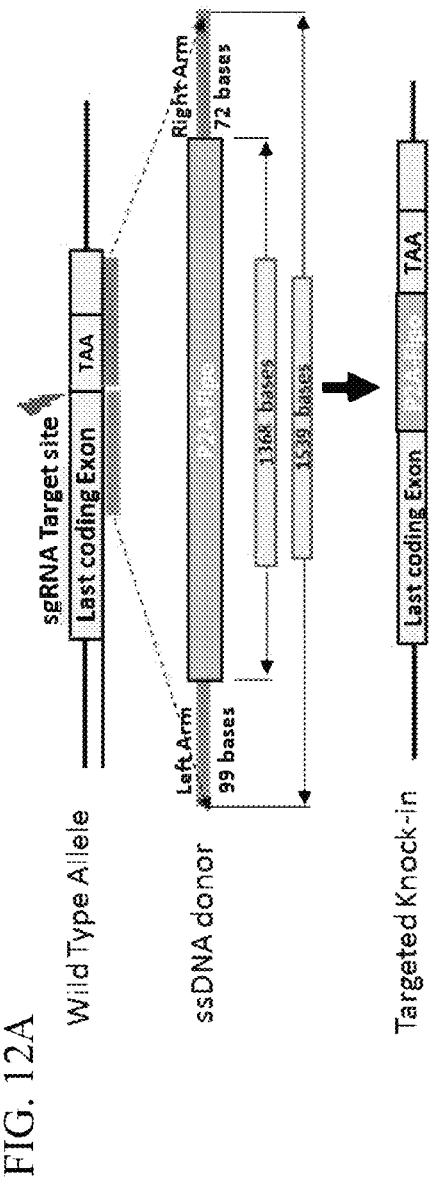
FIG. 12A
FIG. 12C
FIG. 12E

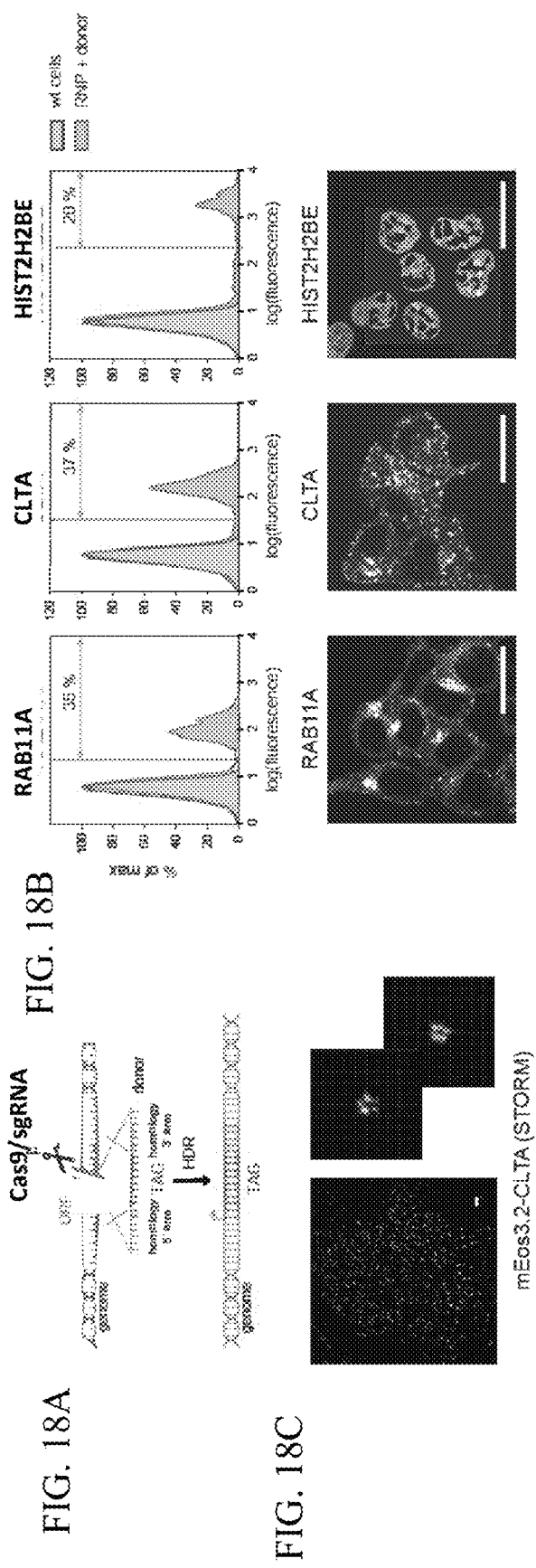

FIG. 19A  Exonuclease ssDNA production  FIG. 19B  IVT-RT ssDNA production

TREATMENT METHODS USING DNA EDITING WITH SINGLE-STRANDED DNA

CROSS-REFERENCE TO RELATED PATENT APPLICATIONS

The present application is a continuation-in-part application under 35 U.S.C. § 365(c), of International Application No. PCT/US2016/035660, filed on Jun. 3, 2016, which claims the benefit of priority to U.S. Provisional Patent Application No. 62/170,306, filed on Jun. 3, 2015, the contents of which are incorporated herein by reference in their entireties.

SEQUENCE LISTING

This application includes an electronically submitted sequence listing in .txt format. The .txt file contains a sequence listing entitled "2018-01-18_6278-00003_Sequence_Listing_ST25.txt" created on Jan. 17, 2018 and is 1,460 bytes in size. The Sequence Listing contained in this .txt file is part of the specification and is hereby incorporated by reference herein in its entirety. The Substitute Sequence Listing does not introduce new matter and otherwise is proper.

BACKGROUND

The field of the invention relates to compositions, methods, and kits for modifying DNA within cells as well as compositions and methods for modifying gene expression in a cell. In particular, the field of the invention relates to compositions, methods, and kits for DNA editing using single-stranded DNA (ssDNA). Compositions and methods for modifying gene expression using artificial microRNAs (amiRNA) are also contemplated.

To ensure overall genome stability and viability, cells have evolved complex mechanisms for the accurate and efficient repair of DNA damage. In eukaryotic cells, the repair of double-strand breaks (DSBs) occurs primarily by two pathways: Non-Homologous End-Joining (NHEJ) and Homology Directed Repair (HDR). In the NHEJ pathway, several factors act to re-ligate the two DNA ends created by the DSB. In the HDR pathway, a homologous DNA template is used to repair the DSB.

Exploiting the HDR pathway has become a powerful means of DNA editing, including the editing of genomes. Currently, there are several widely used systems to introduce targeted cuts such as DSBs into the genomes of cells including Zinc Finger Nucleases (ZFNs), Transcription activator-like effector nucleases (TALENs), CRISPR-Cas systems (Clustered, regularly interspaced short palindromic repeat (CRISPR)-CRISPR-associated proteins (Cas)), and Argonaute nuclease systems. See, e.g., Gaj et al., *Trends in Biotechnology* 31(7): 397-405 (2013); Gao et al., *Nature Biotechnology*, published online May 2, 2016. ZFNs and TALENs are generally chimeric nucleases composed of programmable sequence-specific DNA-binding sequences linked to nonspecific DNA cleavage domains. The sequence specificity of CRISPR-Cas and Argonaute nuclease systems, on the other hand, derive from guide polynucleotides (e.g., RNA or DNA) that direct the nuclease activity of Cas or Argonaute proteins to particular sequences. By introducing one of these targeted nuclease systems into a cell along with a repair template DNA encoding sequences or "arms" homologous to the upstream and downstream sequences near the nuclease cut site, the HDR pathway can be used to insert a DNA of interest (DOI) at nearly any location in the genome.

The repair-template DNA may be single-stranded DNA (ssDNA) or double-stranded DNA (dsDNA). Single-stranded DNA repair templates have been typically about 100-200 bases long, consisting of a few bases of altered sequence (e.g., point mutations, recombinase recognition sequences, short deletions or insertions of a few bases) flanked by homology arms of about 40-80 bases. Double-stranded DNA repair-templates generally require long homology arms and typically are inserted with much lower efficiency than ssDNA repair templates. See Singh et al., *Genetics* 199:1-15 (2015); Yang et al., *Nat Protoc* 9:1956-1968 (2014); and Ran et al., *Nat Protoc* 8:2281-2308 (2013). Currently, ssDNA repair templates have not been used to insert long DOIs due to limitations in the overall length of ssDNA that can be synthesized and uncertainties of whether ssDNA repair templates harboring long DOIs would be properly incorporated into a target sequence using a cell's endogenous HDR machinery. Insertion of large DOIs (>100 bases) generally relies on the use of dsDNA with long homology arms, which are laborious to create and have poor insertion efficiencies. Thus, there is a need in the art for simpler, more efficient methods of inserting large DOIs (>100 bases) into target DNA sequences within a cell.

SUMMARY

Disclosed are compositions, methods, and kits for DNA editing using single-stranded DNA (ssDNA) as well as compositions and methods for modifying gene expression. The disclosed composition, methods, and kits may be used for modifying genomic DNA.

In one aspect, compositions for modifying a target DNA sequence in a cell are provided. The compositions may include single-stranded DNA (ssDNA). The compositions may also include (a) single-stranded DNA (ssDNA) and (b) a nuclease system capable of cutting the target DNA sequence. The ssDNA may include a 5' homology arm having substantial sequence identity to the target DNA sequence, an exogenous sequence, and a 3' homology arm having substantial sequence identity to the target DNA sequence. Also contemplated are delivery particles including such compositions for use in pharmaceutical compositions. Such delivery particles may include polymeric nanoparticles, liposomal nanoparticles, or nanoparticles including lipids and at least one type of polymer.

In a further aspect, methods for modifying a target DNA sequence in a cell are provided. The methods may include: (a) introducing a single-stranded DNA (ssDNA) in the cell and (b) introducing or expressing a nuclease system in the cell, wherein the nuclease system cuts the target DNA sequence.

In a still further aspect, the methods of the present invention may be performed to modify a target DNA sequence in a cell and may include contacting the cell with any one of the delivery particles described herein in an amount effective to allow delivery of the composition into the cell and modification of the target DNA sequence. The contacting may occur in vitro, in vivo, in situ, or ex vivo.

In another aspect, kits or systems for modifying a target DNA sequence in a cell also are contemplated. The kits or systems include components which may include one or more of an RNA polymerase, a reverse transcriptase, an RNA-degrading enzyme, and a nuclease system. Optionally, the kits or systems may include a DNA vector comprising from 5' to 3' a promoter, a cloning site, and a restriction enzyme site.

In still another aspect, the kits or systems of the present invention may include (a) single-stranded DNA (ssDNA) and (b) a nuclease system capable of cutting a target DNA sequence. The ssDNA of the kits may be relatively long (e.g., >100 bases).

In a further aspect, engineered eukaryotic cells including amiRNAs are also provided. The engineered eukaryotic cells may include an exogenous DNA construct encoding an amiRNA. The DNA construct may be inserted into an intron of a gene. In some embodiments, the DNA construct lacks a promoter, reporter sequence, and/or a polyA tail.

BRIEF DESCRIPTION OF THE DRAWINGS

FIG. 2(a), FIG. 2(b), FIG. 2(c) and FIG. 2(d) show targeted insertion of ssDNA encoding anti-eGFP amiRNA by CRISPR/Cas9 system (Exp. 2). FIG. 2(a) shows schematics of targeted integration of amiR-eGFP123/419 sequences into the intron 6 of eEF-2 gene (upper panel) and location of amiR-eGFP123 and -eGFP419 target sites on eGFP cDNA (lower panel). From the correctly targeted eEF-2 locus, amiRNAs get transcribed and subsequently bind to the target sites (amiR-eGFP123=pink line and amiR-eGFP419=purple line) on eGFP mRNA, leading to eGFP knockdown. Red arrows indicate the location of primer set (PP119/PP120) used for detection of fetuses with targeted insertion. FIG. 2(b) shows eGFP fluorescence among E13.5 day fetuses observed under a fluorescent stereomicroscope showing successful knockdown in some fetuses. FIG. 2(c) shows genotyping of fetuses by PCR using primer set shown in FIG. 2(a). The embryo numbers in FIG. 2(b) and FIG. 2(c) correspond with each other. Expected fragment sizes: wild-type=301-bp (black lower arrow), targeted insertion=625-bp (blue upper arrow). FIG. 2(d) shows targeted insertion efficiency. Fetuses containing functional amiRNA sequence were considered as 'embryos with targeted insertions' even though insertions were not fully accurate.

FIG. 3(a), FIG. 3(b), FIG. 3(c), and FIG. 3(d) show targeted insertion of ssDNA encoding anti-Otx2 amiRNA by CRISPR/Cas9 system (Exp. 4). FIG. 3(a) shows schematics of targeted integration of amiR-Otx2_546 into intron 6 of eEF-2 gene (upper panel) and Otx2 genomic region showing amiR-Otx2_546 binding site (lower panel). The exons of Otx2 are shown as boxes and the boxes with homeodomain region are shaded black. Red arrows indicate the location of primer set (PP119/PP120) used for detection of fetuses with targeted insertion. FIG. 3(b) shows the resultant fetuses photographed at E14.5. FIG. 3(c) shows genotyping of fetuses by PCR using primer set shown in FIG. 3(a). The embryo numbers in FIG. 3(b) and FIG. 3(c) correspond with each other. Expected fragment sizes: wild-type=301-bp (black upper arrow), targeted insertion=487-bp (blue lower arrow). FIG. 3(d) shows targeted insertion efficiency.

Fetuses containing functional amiRNA sequence were considered as 'embryos with targeted insertions' even though insertions were not fully accurate.

FIG. 4(a), FIG. 4(b), FIG. 4(c), and FIG. 4(d) show targeted insertion of ssDNA encoding Cre-activatable anti-eGFP amiRNA by CRISPR/Cas9 system (Exp. 5). FIG. 4(a) shows schematics of targeted integration of reverse orientated amiR-eGFP123/419' and mutant loxP sites (JT15 and JTZ17) into the intron 6 of eEF-2 gene and subsequent Cre-loxP recombination to switch the amiRNA cassette to the right orientation. Functional amiRNAs do not get produced from the targeted 'amiRNA-off' allele because of the opposite orientation of amiRNA with respect to the eEF-2 gene. After Cre recombination, the allele gets converted to 'amiRNA-on' that produces functional amiRNA. Red arrows indicate the primers (PP119, PP120 and M412) used for genotyping. FIG. 4(b) shows genotyping of fetuses by PCR using primer set (PP119/PP120). Expected fragment sizes: wild-type=301-bp (black arrow), targeted insertion=705-bp (blue arrow). FIG. 4(c) shows targeted insertion efficiency. FIG. 4(d) shows dotplot of embryonic feeder cells, derived from Exp. 5 samples #4 (upper) and #6 (lower), nine days after transfection with (left) or without (right) the iCre plasmid. The cells showing weak eGFP fluorescence are partitioned within the box in each plot. FIG. 4(e) shows genotyping of embryonic feeder cells used in the experiment FIG. 4(d) by PCR with primer sets shown in FIG. 4(a).

Figure 5A:
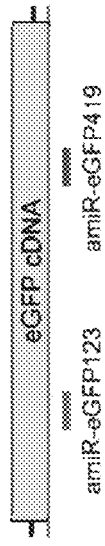
Figure 5B:
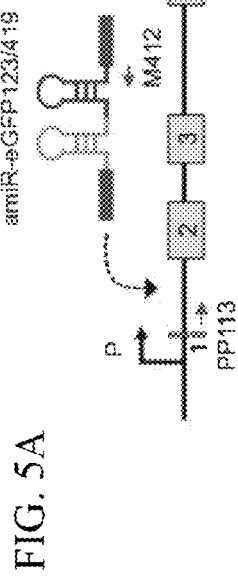
Figure 5C:
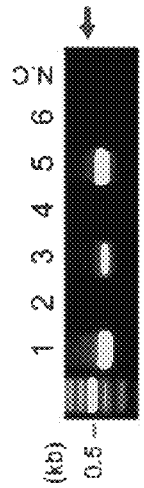
Figure 5D:
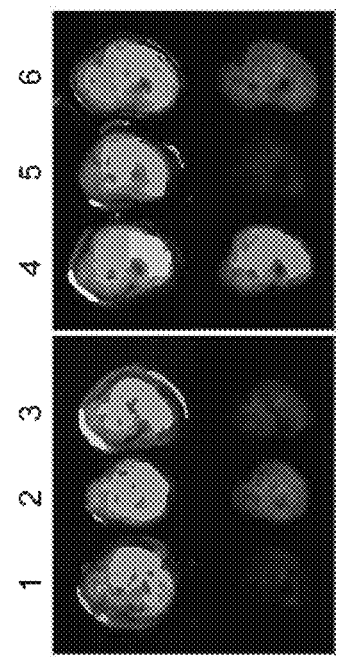

FIG. 5(a), FIG. 5(b), FIG. 5(c), and FIG. 5(d) show targeted insertion of ssDNA encoding anti-eGFP amiRNA by CRISPR/Cas9 system (Exp. 1). FIG. 5(a) shows schematics of targeted integration of amiRNA-eGFP123/419 into the intron 1 of eEF-2 gene (upper panel) and location of amiRNA-eGFP123 and -eGFP419 target sites on eGFP cDNA (lower panel). From the correctly targeted eEF-2 locus, amiRNAs get transcribed and subsequently bind to the target sites (amiR-eGFP123=pink line and amiR-eGFP419=purple line) on eGFP mRNA, leading to eGFP knockdown. Red arrows indicate the location of primer set (PP113/M412) used for detection of fetuses with targeted insertion. FIG. 5(b) shows eGFP fluorescence among E13.5 fetuses observed under a fluorescent stereomicroscope showing successful knockdown in some fetuses. FIG. 5(c) shows genotyping of fetuses by PCR using primer set shown in FIG. 5(a). The embryo numbers in FIG. 5(b) and FIG. 5(c) correspond with each other. Expected fragment sizes: targeted insertion=562-bp (blue arrow). FIG. 5(d) shows targeted insertion efficiency. Fetuses containing functional amiRNA sequence were considered as 'embryos with targeted insertions' even though insertions were not fully accurate.

FIG. 6(a), FIG. 6(b), FIG. 6(c), and FIG. 6(d) show targeted insertion of ssDNA encoding anti-Otx2 amiRNA by CRISPR/Cas9 system (Exp. 3). FIG. 6(a) shows schematics of targeted integration of amiR-Otx2_518 into the intron 6 of eEF-2 gene (upper) and Otx2 genomic region showing amiRNA-Otx2_518 binding site (lower panel). The exons of Otx2 are shown as boxes and the boxes with homeodomain region are shaded black. Red arrows indicate the location of primer set (PP119/PP120) used for detection of fetuses with targeted insertion. FIG. 6(b) shows the resultant fetuses photographed at E14.5. FIG. 6(c) shows genotyping of fetuses by PCR using primer set shown in FIG. 6(a). The embryo numbers in FIG. 6(b) and FIG. 6(c) correspond with each other. Expected fragment sizes: wild-type=301-bp (black lower arrow), targeted insertion=487-bp (blue upper arrow). FIG. 6(d) shows targeted insertion efficiency.

FIG. 7(a), FIG. 7(b), and FIG. 7(c) show comparison of insertion efficiencies of ssDNA or dsDNA repair templates (encoding anti-eGFP amiRNA) by the CRISPR/Cas9 system (Exp. 6 and 7). FIG. 7(a) shows the genomic structure of eEF-2 locus with targeted integration of amiRNA-eGFP123/ 419. Red arrows indicate the location of primer sets (PP117/ PP118 and PP119/M412) used for detection of blastocysts with targeted insertion by nested PCR. ssDNA (in Exp. 6) or dsDNA (in Exp. 7) containing amiR-eGFP123/419 and homology arms with 55-bases long on each side were prepared and used as repair DNAs. Each of the repair DNA (20 ng/µl) was subjected to micro-injections together with Cas9 mRNA (10 ng/µl) and sgRNAs for TS2 (10 ng/µl). FIG. 7(b) shows the genotyping of blastocysts by nested PCR using primer set shown in FIG. 7(a). Expected fragment size: 459-bp. FIG. 7(c) shows targeted insertion efficiency.

FIG. 8(a), FIG. 8(b), and FIG. 8(c) show insertion of sequences in the eEF-2 intron 6 does not affect its mRNA splicing. FIG. 8(a) shows the genomic structure and expected splicing pattern of wild-type and 'amiRNA-off' alleles (containing reverse orientated 'amiRNA-eGFP123/ 419' and mutant loxP sites) of eEF-2 gene. Red arrows indicate the location of primer set (PP164/PP118) used for reverse transcription PCR (RT-PCR). FIG. 8(b) shows RT-PCR results using cDNAs prepared from embryonic feeder cells derived from the fetuses in Exp. 5 (see FIG. 4). The sample numbers in FIG. 8(b) correspond with those in FIG. 4(b). Sample No. 6; wild-type allele, No. 4 and 9; heterozygotes for 'amiRNA-off' allele, No. 8; homozygote for 'amiRNA-off' allele. Expected fragment size: 500-bp (from cDNA). FIG. 8(c) shows junctional regions between exon 6 and 7.

Figure 9:
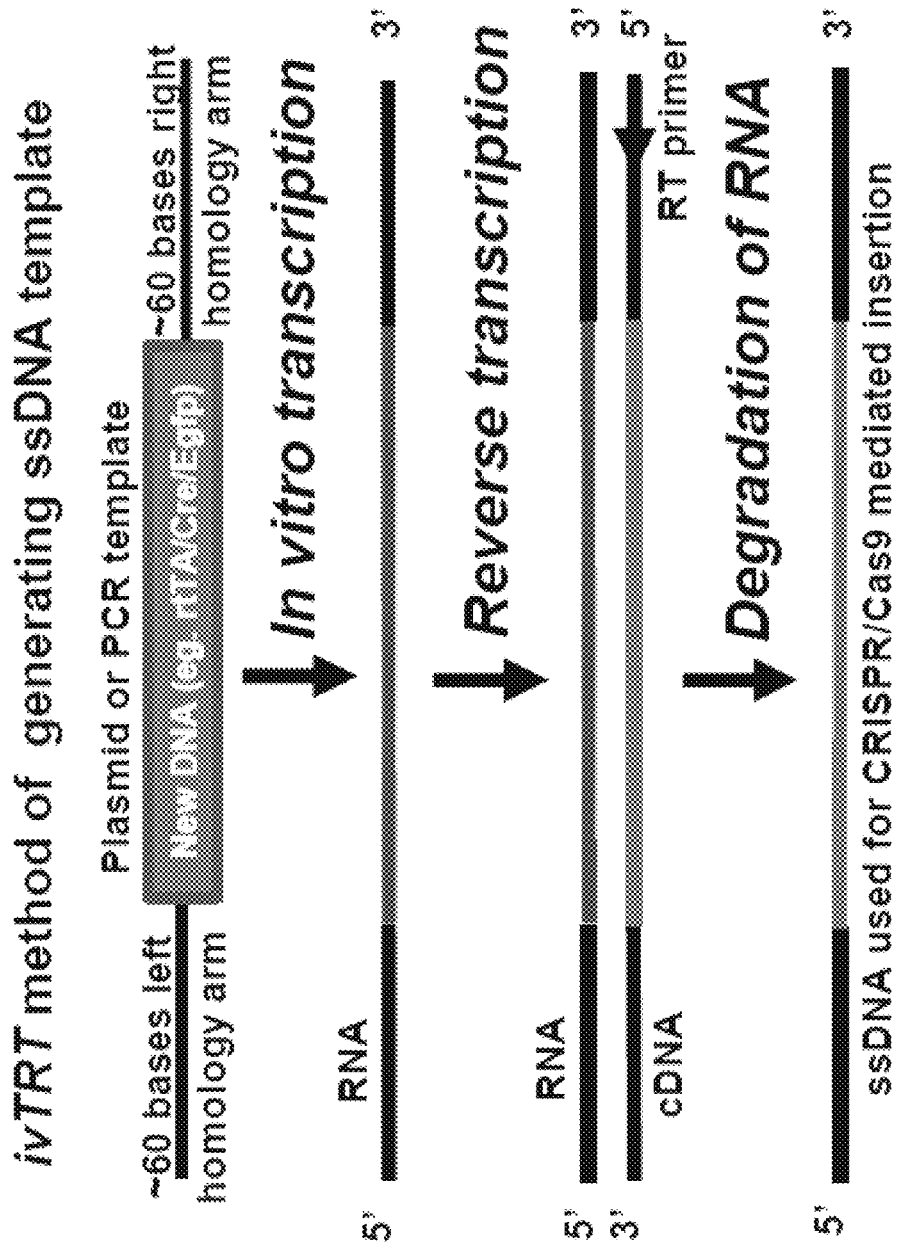

FIG. 9 shows ssDNA synthesis by ivTRT strategy. Schematic of plasmid or PCR product templates showing elements such as rtTA/Cre/Egfp inserts (green) flanked by 3' and 5' homologous sequences to the target (~60 bp each), used for in vitro transcription of RNA.

Figure 10:
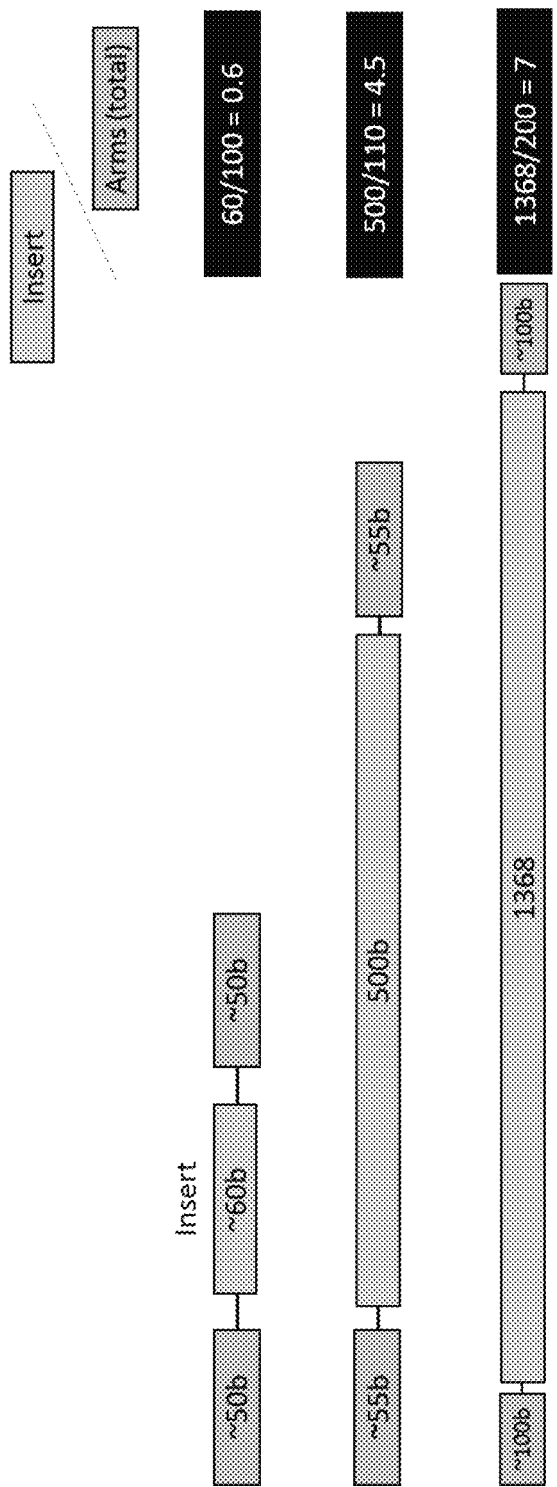

FIG. 10 shows a schematic illustrating that the ssDNA repair templates disclosed herein include significantly greater ratios between the length of the exogenous or insert sequence (Insert) and the sum of the length of the 5' homology arm and the 3' homology arm (Arms (total)) as compared to ssDNA repair templates previously used.

FIG. 11(a), FIG. 11(b), FIG. 11(c), FIG. 11(d), FIG. 11(e), and FIG. 11(f) show insertion of over 1 kb ssDNA at Otoancorin and Fgf8 loci. FIG. 11(a, b) Schematic showing Otoancorin FIG. 11(a) and Fgf8 FIG. 11(b) loci, ssDNA donor templates and targeted Knock-in alleles. The lengths of ssDNA, homology arms and the rtTA-polyA FIG. 11(a) or P2A-FlpO FIG. 11(b) cassettes are indicated. FIG. 11(c, d) Genotyping G0 animals for detection of cassette insertion. Schematic of primer locations for 5' and 3' junction PCRs is shown along with the expected amplicon sizes. FIG. 11(c) Samples Otoa G0 pups 3, 7 and 8 are positive for the rtTA cassette insertion as seen by both the 5' and 3' junction PCRs. Note that the amplicons for the 3' PCR are weak and are indicated by asterisks. FIG. 11(d) Founder 4 is positive for the FlpO cassette insertion by both 5' and 3' PCRs. The gel on the right shows that this founder has a bi-allelic insertion of the cassette. Wt: wild type, M; 100 bp marker, kb: 1 kb Marker. FIG. 11(e, f) Sequencing of Otoancorin founder 3 and Fgf8 founder 4. The guide RNA sequences (italics), along with the cut sites, PAM sequences (in red) and a few bases of flanking sequences are shown above. Sequence chromatograms showing correct insertion of cassette junctions.

Figure 12B:
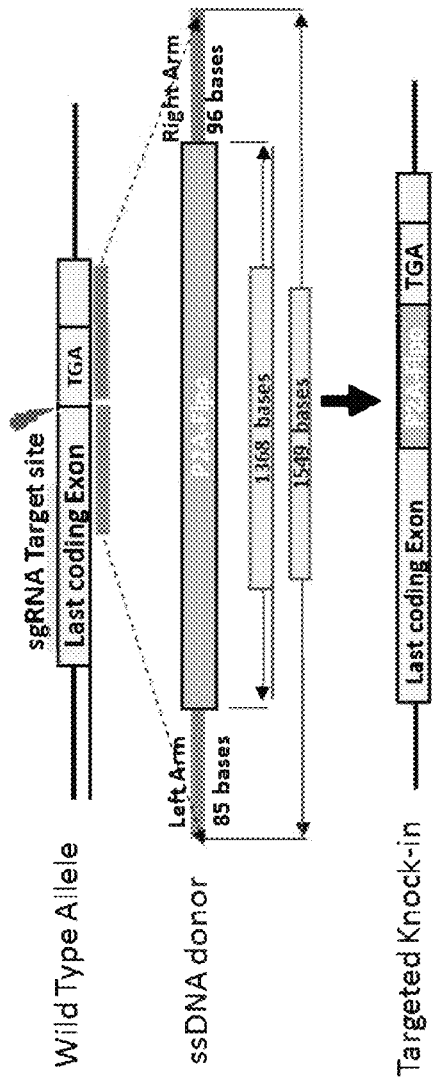
Figure 12D:
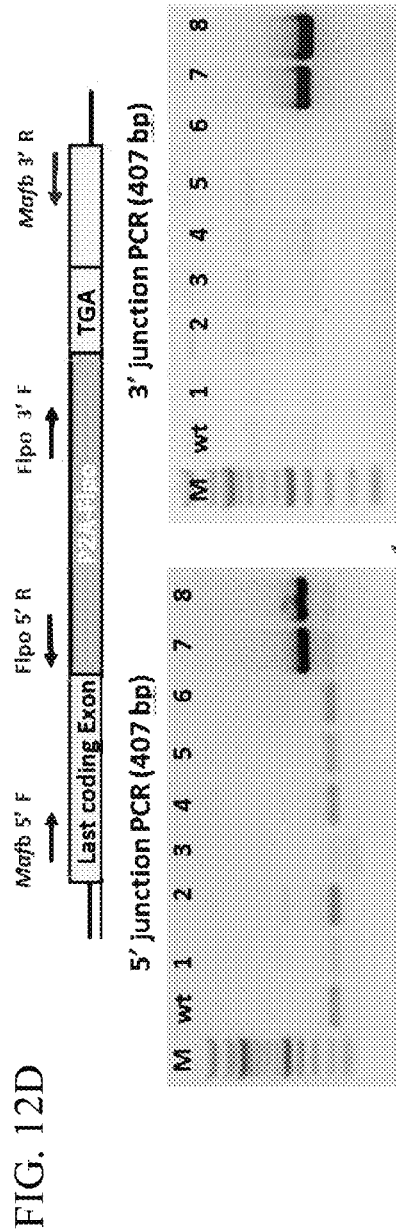
Figure 12F:
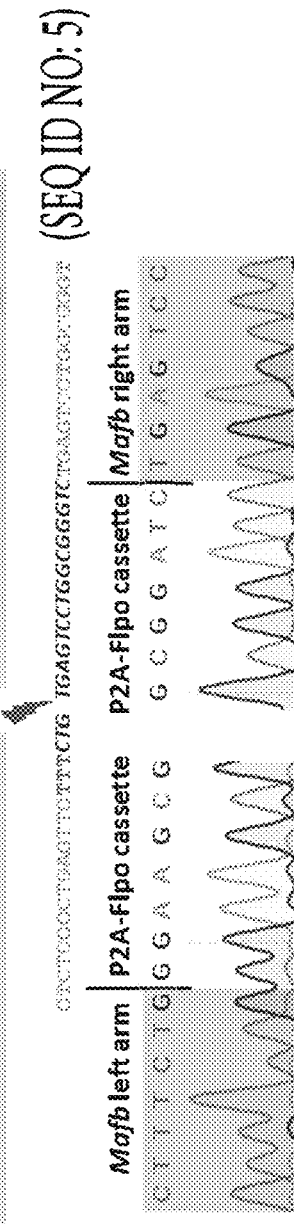

FIG. 12(a), FIG. 12(b), FIG. 12(c), FIG. 12(d), FIG. 12(e), and FIG. 12(f) show insertion of over 1 kb ssDNA into Slc26a5 and MafB. FIG. 12(a, b) Schematic showing Slc26a5 FIG. 12(a) and MafB FIG. 12(b), ssDNA donor templates and targeted knock-in alleles. The lengths of ssDNA, homology arms and the P2A-FlpO cassettes are indicated. FIGS. 12(b, d) Genotyping G0 animals for detection of cassette insertion. Schematic of primer locations for 5' and 3' junction PCRs is shown along with the expected amplicon sizes. FIG. 12(c) Founders 1 and 3 are positive for the P2A-FlpO cassette insertion using both 5' and 3' PCRs. Note that the 3' junction PCR for founder #1 is bigger than the expected size and it contains genomic DNA duplications (data not shown) FIG. 12(d) Founder 4 is positive for the FlpO cassette insertion by both 5' and 3' PCRs. Wt: wild type, M; 100 bp marker. FIGS. 12(e, f) Sequencing of Slc26a5 founder #1 and Mafb founder #7. The guide RNA sequences (italics), along with the cut sites, PAM sequences (in red) and a few bases of flanking sequences are shown above. Sequence chromatograms showing cassettes insertions junctions.

Figure 13:
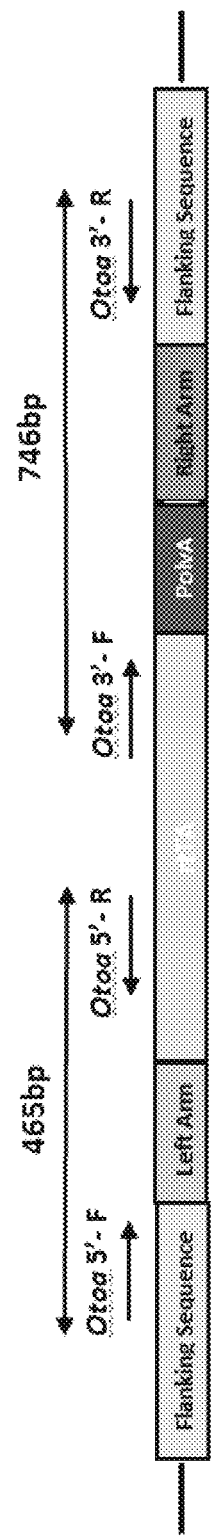

FIG. 13 shows a schematic of the Otoa-rtTA ssDNA. Various sequence elements are color coded. The primers used for 5' and 3' junction PCR and the amplicon sizes are shown above the schematic.

Figure 14:
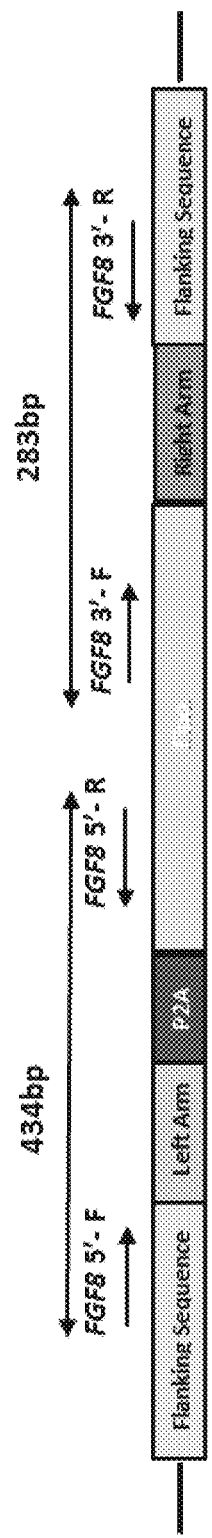

FIG. 14 shows a schematic of the Fgf8-P2A-Flpo-ssDNA. Various sequence elements are color coded. The primers used for 5' and 3' junction PCR and the amplicon sizes are shown above the schematic.

Figure 15:
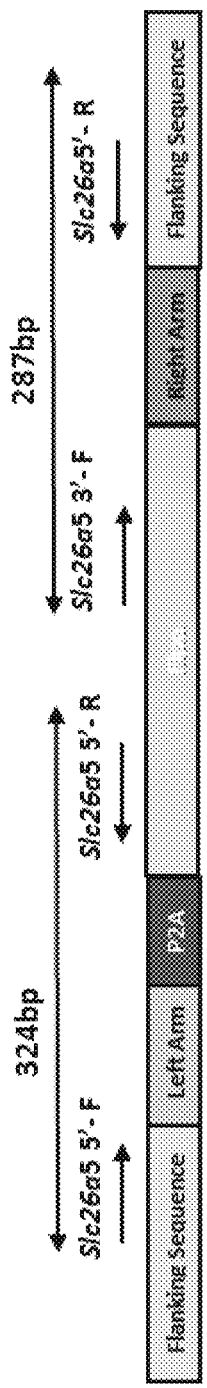

FIG. 15 shows a schematic of the slc26a5-Flpo-ssDNA. Various sequence elements are color coded. The primers used for 5' and 3' junction PCR and the amplicon sizes are shown above the schematic.

Figure 16:
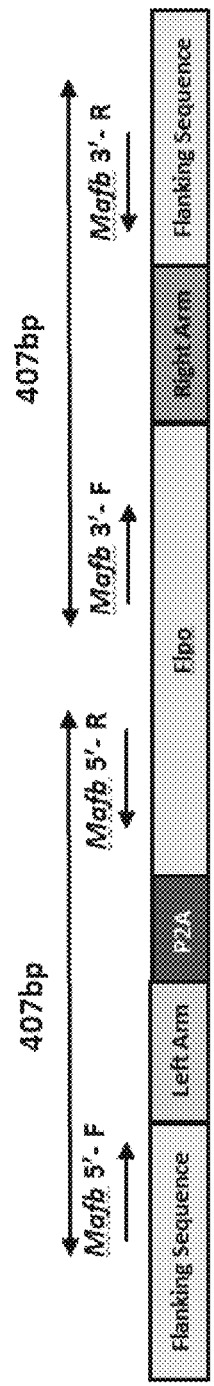

FIG. 16 shows a schematic and the sequence of the Mafb-Flpo-ssDNA. Various sequence elements are color coded. The primers used for 5' and 3' junction PCR and the amplicon sizes are shown above the schematic.

Figure 17A:
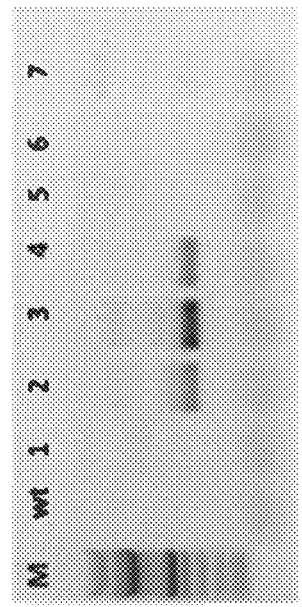
Figure 17B:
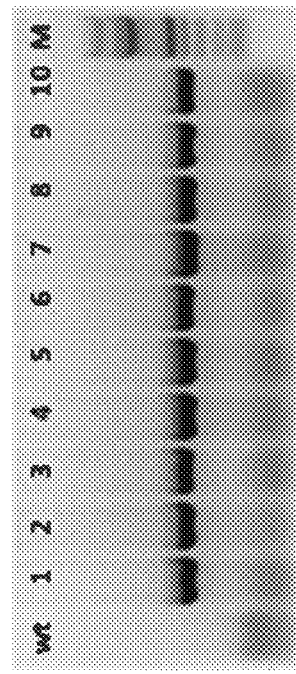

FIG. 17(a), and FIG. 17(b) show shows germ line transmission of Easi-CRISPR knock-in mouse models. FIG. 17(a) Genotyping of F1 pups derived from mating of the Fgf8-P2A-FlpO founder 4. Note that this founder is a homozygote and mating to a wild type mouse resulted in all pups heterozygous for the FlpO insertion. FIG. 17(b) Genotyping of F1 pups from Slc25a5-P2A-FlpO founder #3 showing that F1 pups 2,3 and 4 contain the knock-in cassette.

FIG. 18(A), FIG. 18(B), and FIG. 18(C) show endogenous gene tagging with ssDNA donors. FIG. 18(A) Functional tagging at endogenous genomic loci. Tag (e.g. GFP) is introduced in an endogenous open-reading-frame (ORF) and the resulting fusion protein expressed from the endogenous ORF promoter. FIG. 18(B) Endogenous GFP tagging of RAB11A (endosomal Rab protein), CLTA (clathrin light chain) and HISTH2BE (histone) in HEK293T using long ssDNA donors. Knock-in efficiency was measured by flow cytometry analysis ~7 days after Cas9/sgRNA and donor electroporation. Confocal microscopy of GFP-sorted cells is shown (scale bars: 10 µm). FIG. 18(C) STORM super-resolution imaging of mEos3.2-CLTA in HEK293T cells. Scale bar: 1 µm; grid size in insert: 100 nm.

Figures 19C, 19D:
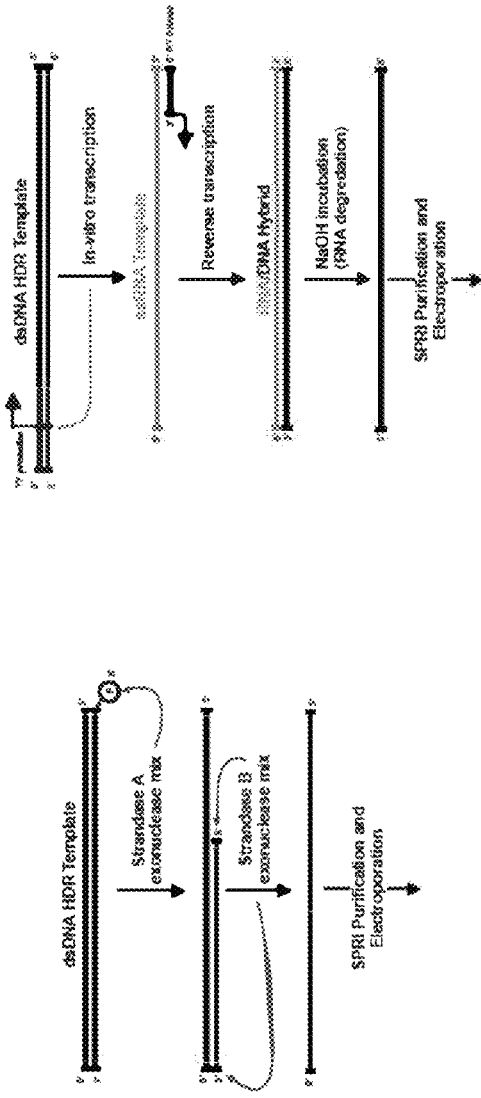

FIG. 19(A), FIG. 19(B), FIG. 19(C), and FIG. 19(D) show multiple methods to produce long ssDNA HDR templates. FIG. 19(A) If a large enough amount of long single stranded DNA sequence could be produced for electroporation, off-target integrations could be reduced without overly compromising on-target efficiency. One method we developed involves a two step selective exonuclease digestion that specifically degrades one strand of a PCR product that has been labeled by 5' phosphorylation, easily added onto a PCR primer prior to amplification. FIG. 19(B) We also applied a second ssDNA production method based on sequential in-vitro transcription (IVT) and reverse transcription (RT) reaction. A PCR product with a short T7 promoter appended serves as an IVT template to produce a ssRNA product. Following annealing of an RT primer and reverse transcription, an RNA/DNA hybrid is formed which can be easily transformed into a long ssDNA template by incubation in sodium hydroxide (selectively degrades RNA strand). FIG. 19(C) At 2 days post-electroporation, viability in CD3+T cells electroporated with only a ssDNA template was higher than those electroporated with only a dsDNA template. FIG. 19(D) A ssDNA RAB11A-GFP HDR template showed high efficiency GFP integration similar to dsDNA templates, and maintained high efficiency integrations at higher molar amounts of template, potentially due to increased viability as well as less mass per mole of DNA template. Individual points represent at least two healthy donors.

DESCRIPTION

Disclosed are compositions, methods, and kits for editing DNA, such as genomic DNA, using single-stranded DNA (ssDNA) as well as compositions and methods for modifying gene expression. The disclosed composition, methods, and kits may be further described as follows.

Unless otherwise specified or indicated by context, the terms "a", "an", and "the" mean "one or more." In addition, singular nouns such as "ssDNA" and "amiRNA," should be interpreted to mean "one or more ssDNAs" and "one or more amiRNAs," respectively, unless otherwise specified or indicated by context.

As used herein, "about" and "approximately" will be understood by persons of ordinary skill in the art and will vary to some extent on the context in which they are used. If there are uses of the term which are not clear to persons of ordinary skill in the art given the context in which it is used, "about" and "approximately" will mean plus or minus 510% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion of additional components other than the components recited in the claims. The term "consisting essentially of" should be interpreted to be partially closed and allowing the inclusion only of additional components that do not fundamentally alter the nature of the claimed subject matter.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure. Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like. All percentages referring to amounts are by weight unless indicated otherwise.

Nuclease Editing Systems for DNA

Several nuclease systems, including the CRISPR/Cas system, have emerged as popular DNA and genome editing methods. These methods can be used not only for gene disruption, but also for targeted modification using a DNA repair template. Single-stranded DNA (ssDNA) repair templates, up to 200-bases long, are used as donors for insertion of short stretches. See, e.g., Harms et al., *Curr Protoc Hum Genet* 83:15(17) 11-15 (2014). However, because longer ssDNAs (>200-bases long) are not generally commercially available, longer insertions require the use of inefficient dsDNAs (plasmid-based constructs), which can be more laborious to create and generally have poor insertion efficiencies.

To overcome these limitations, the present inventors have, in part, developed a technique that can be used to synthesize ssDNA donors having more than 200 nucleotides. In one aspect, the present invention generally relates to the inventors' discovery that ssDNA having lengths above 200 nucleotides can serve as efficient donors for targeted modification in cells. Furthermore, the inventors discovered that relatively short homology arms are needed to insert longer DNA sequences of interest when ssDNAs having lengths over 200 nucleotides are used as repair templates. In another aspect, the present invention generally relates to the inventors' demonstration that amiRNAs targeted to introns can efficiently modify gene expression.

In the Examples, the inventors synthesized ssDNA donors greater than 200 nucleotides in length and then used them in CRISPR/Cas9-mediated targeted insertion experiments. The inventors observed up to 100% overall insertion efficiency, and up to 50% insertion efficiency in both alleles. Notably, the homology arm lengths in these samples ranged from approximately 55 bases-112 bases on each side demonstrating that ssDNA-based insertion is efficient even though the length of donors was greater than 200 nucleotides in length and that the DNA sequence of interest was significantly longer than the length of the homology arms.

In one aspect, the present invention comprises compositions, methods, and kits for DNA editing using single-stranded DNA (ssDNA). The disclosed compositions, methods, and kits may be utilized for DNA editing in vitro, in vivo, or ex vivo and may be used to insert DNA sequences of interest such as large expression cassettes and transgenes encoding, without limitation, artificial microRNA (amiRNA) constructs, reporters (e.g., EGFP/LacZ etc.), sequence tags (e.g., immune-affinity tags), and genes such as rtTA/tTA, Cre, Flpo and the like. The compositions, methods, and kits may also be used, for example, to introduce multiple point mutations into a genomic sequence, to generate conditional and nonconditional knock-in and knock-out constructs, to alter the expression of targeted genes, to generate transgenic animals and plants, and to develop human therapeutics.

Methods for Modifying a Target DNA Sequence

Methods for modifying a target DNA sequence in a cell are provided. The methods may include: (a) introducing a single-stranded DNA (ssDNA) in the cell and (b) introducing or expressing a nuclease system in the cell, wherein the nuclease system cuts the target DNA sequence. The ssDNA may include a 5' homology arm having substantial sequence identity to the target DNA sequence, an exogenous sequence, and a 3' homology arm having substantial sequence identity to the target DNA sequence.

The term "target DNA sequence" as used herein refers to any DNA nucleic acid residing in a cell. The target DNA sequence may be endogenous to the cell (e.g., genome or other self-replicating form of DNA such as a plasmid endogenously found in the cell) or exogenous to the cell (e.g., transgenes or plasmids introduced in the cell). The target DNA sequence may be within or around a gene.

In some embodiments, the target DNA sequence is in an intron of a gene. The gene may be constitutively expressed or may be expressed in a tissue-specific manner. As used herein, "constitutively expressed" refers to genes that are expressed in all cells of an organism. Common constitutively expressed genes include housekeeping genes that are required for the maintenance of basic cellular function. In the non-limiting Examples, the inventors target introns within the eEF2 housekeeping gene but other housekeeping genes may be used in accordance with the present invention.

As used herein, "introducing" describes a process by which exogenous polynucleotides (e.g., DNA or RNA) or protein is introduced into a recipient cell. Methods of introducing nucleic acids and proteins into a cell are known in the art and may include, without limitation, microinjection, transformation, and transfection methods. Transformation or transfection may occur under natural or artificial conditions according to various methods well known in the art, and may rely on any known method for the insertion of foreign nucleic acid sequences into a prokaryotic or eukaryotic host cell. The method for transformation or transfection is selected based on the type of host cell being transformed and may include, but is not limited to, bacteriophage or viral infection, electroporation, heat shock, lipofection, and particle bombardment. Microinjection of nucleic acids and/or proteins may also be used to introduce nucleic acids and/or proteins into cells as used, for example, with embryos when making transgenic animals.

Conventional viral and non-viral based gene transfer methods can be used to introduce nucleic acids into cells or target tissues. Non-viral vector delivery systems may include DNA plasmids or nucleic acid complexed with a delivery vehicle, such as a liposome. Delivery can be to cells (e.g. in vitro or ex vivo administration) or target tissues (e.g. in vivo administration).

Single-stranded DNA (ssDNA) of the present invention may be a single-stranded DNA polynucleotide. The terms "polynucleotide," "polynucleotide sequence," "nucleic acid" and "nucleic acid sequence" refer to a nucleotide, oligonucleotide, polynucleotide (which terms may be used interchangeably), or any fragment thereof. These phrases also refer to DNA or RNA of genomic, natural, or synthetic origin (which may be single-stranded or double-stranded and may represent the sense or the antisense strand).

Regarding polynucleotide sequences, the terms "percent identity" and "% identity" and "sequence identity" refer to the percentage of residue matches between at least two polynucleotide sequences aligned using a standardized algorithm. Such an algorithm may insert, in a standardized and reproducible way, gaps in the sequences being compared in order to optimize alignment between two sequences, and therefore achieve a more meaningful comparison of the two sequences. Percent identity for a nucleic acid sequence may be determined as understood in the art. (See, e.g., U.S. Pat. No. 7,396,664). A suite of commonly used and freely available sequence comparison algorithms is provided by the National Center for Biotechnology Information (NCBI) Basic Local Alignment Search Tool (BLAST), which is available from several sources, including the NCBI, Bethesda, Md., at its website. The BLAST software suite includes various sequence analysis programs including "blastn," that is used to align a known polynucleotide sequence with other polynucleotide sequences from a variety of databases. Also available is a tool called "BLAST 2 Sequences" that is used for direct pairwise comparison of two nucleotide sequences. "BLAST 2 Sequences" can be accessed and used interactively at the NCBI website. The "BLAST 2 Sequences" tool can be used for both blastn and blastp (discussed above).

Regarding polynucleotide sequences, percent identity may be measured over the length of an entire defined polynucleotide sequence, for example, as defined by a particular SEQ ID number, or may be measured over a shorter length, for example, over the length of a fragment taken from a larger, defined sequence, for instance, a fragment of at least 20, at least 30, at least 40, at least 50, at least 70, at least 100, or at least 200 contiguous nucleotides. Such lengths are exemplary only, and it is understood that any fragment length supported by the sequences shown herein, in the tables, figures, or Sequence Listing, may be used to describe a length over which percentage identity may be measured.

Regarding polynucleotide sequences, "variant," "mutant," or "derivative" may be defined as a nucleic acid sequence having at least 50% sequence identity to the particular nucleic acid sequence over a certain length of one of the nucleic acid sequences using blastn with the "BLAST 2 Sequences" tool available at the National Center for Biotechnology Information's website. (See Tatiana A. Tatusova, Thomas L. Madden (1999), "Blast 2 sequences—a new tool for comparing protein and nucleotide sequences", FEMS Microbiol Lett. 174:247-250). Such a pair of nucleic acids may show, for example, at least 60%, at least 70%, at least 80%, at least 85%, at least 90%, at least 91%, at least 92%, at least 93%, at least 94%, at least 95%, at least 96%, at least 97%, at least 98%, or at least 99% or greater sequence identity over a certain defined length.

Single-stranded DNA (ssDNA) of the present invention is relatively long. In some embodiments, the ssDNA may have a length of at least about 200, 250, 300, 350, 400, 450, 500 and 1,500, 2,000, 5,000, 10,000, 15,000, 20,000, 30,000, or the ssDNA may have a length within a range bounded by any of these nucleotide lengths (e.g., a length of 200-1000 nucleotides). The ssDNA may be contain modified nucleotides well known in the art.

The ssDNA may include a 5' homology arm having substantial sequence identity to the target DNA sequence, an exogenous sequence, and a 3' homology arm having substantial sequence identity to a target DNA sequence. Preferably, the ssDNA is arranged in the 5' to 3' direction to include a 5' homology arm having substantial sequence identity to a target DNA sequence, an exogenous sequence, and a 3' homology arm having substantial sequence identity to a target DNA sequence.

In some embodiments, the 5' homology arm and/or the 3' homology arm of the ssDNA are substantially identical to at least about 15, 25, 30, 35, 40, 45, 50, 55, 60, 65, 70, 75, 80, 85, 90, 95, 100, 105, or 110 nucleotides of the target DNA sequence. In some embodiments, the 5' homology arm and 3' homology arm of the ssDNA are substantially identical to no more than about 40, 50, 60, 70, 80, 90, 100, 110, 120, 130, 140, 150, 160, 170, 180, 190, 200, 210, 220, 230, 240, or 250 nucleotides of the target DNA sequence. Preferably, the 5' homology arm and 3' homology arm of the ssDNA are substantially identical to between 35 to 120 nucleotides of the target DNA sequence. In some embodiments, the 5' homology arm is substantially identical to the target DNA sequence on one side of the cut created by a nuclease system and the 3' homology arm is substantially identical to the target DNA sequence on the other side of the cut created by a nuclease system.

As used herein "substantially identical to" or "substantial identity" when referring to polynucleotide sequences of the 5' homology arm and 3' homology arm of the ssDNA of the present invention means polynucleotide sequence identity of at least 40%. Suitable polynucleotide identity can be any value between 40% and 100%. Preferably, polynucleotide identity of the 5' homology arm and 3' homology arm of the ssDNA is 100%.

Within the ssDNA of the present invention, the total length of the 5' and 3' homology arms may be significantly less than the length of the exogenous sequence. Prior to the work of the inventors, ssDNA repair templates were typically about 100-200 bases long. Such repair templates generally included exogenous sequences containing a few bases of altered sequence (e.g., point mutations, recombinase recognition sequences, short deletions or insertions of a few bases) which were flanked by homology arms of about 40-80 bases. See, e.g., FIG. 10. The homology arms, therefore, made up a significant portion of the ssDNA repair template. The inventors, on the other hand, have discovered that ssDNA repair templates that include exogenous sequences over 200 bp could be inserted at high efficiencies even though the ssDNA repair templates only included relatively short 5' and 3' homology arms. See, e.g., FIG. 10.

In view of this discovery, the ssDNA of the present invention may include certain ratios between the length of the exogenous sequence (ES) and the sum of the length of the 5' homology arm (L5') and the 3' homology arm (L3'). The ratio (R) between the length of the exogenous sequence and the total lengths of the 5' homology arm and the 3' homology arm is determined by dividing the length of the exogenous sequence in nucleotides by the combined lengths of both the 5' and 3' homology arms in nucleotides as represented by the formula R=ES/(L5'+L3'). For example, if the ssDNA includes a 5' homology arm that is 99 nucleotides in length, an exogenous sequence that is 1,368 nucleotides in length, and a 3' homology arm this is 72 nucleotides in length, the ratio between the length of the exogenous sequence and the total lengths of the 5' homology arm and the 3' homology arm would be 1368/(99+72)=8:1. In some embodiments of ssDNA comtemplated herein, the ratio (R) of the length of the exogenous sequence to the total length of the 5' homology arm and the 3' homology arm (exogenous sequence length:homology arm length) may be about 1:1, 1.5:1, 2:1, 3:1, 4:1, 5:1, 6:1, 7:1, 8:1, 9:1, 10:1, 15:1, 20:1, 30:1, 40:1, 50:1, 60:1, 70:1, 80:1, 90:1, 100:1 or within a ratio range bounded by any two of these values (i.e., a ratio within a range of 5:1-50:1). In some embodiments, the ratio (R) of the length of the exogenous sequence to the total length of the 5' homology arm and the 3' homology arm (exogenous sequence length:homology arm length) may be between about 1.5:1 and 20:1.

The ssDNA may be synthesized using in vitro methods. In vitro methods contemplated for synthesizing ssDNA include a method including transcribing a DNA template encoding a promoter operably linked to nucleotide sequence including, preferably in the 5' to 3' direction, a 5' homology arm having substantial sequence identity to the target DNA sequence, an exogenous sequence, and a 3' homology arm having substantial sequence identity to the target DNA sequence to produce a RNA transcript, synthesizing a ssDNA/RNA duplex by reverse transcription of the RNA transcript, and degrading the RNA from the ssDNA/RNA duplex using an RNA-degrading enzyme to produce ssDNA. Optionally, the method may further comprise purifying the ssDNA. Purification of the ssDNA may be by gel purification or other DNA purification protocols well known in the art. Promoters appropriate for transcribing a DNA template in vitro are known in the art. Examples of suitable promoters include, without limitation, T7, T3, and SP6 promoters. Preferably, the promoter comprises a T7 promoter and transcription is performed using a T7 RNA polymerase.

Synthesis of the ssDNA/RNA duplex may be performed using a RNA-dependent DNA polymerase such as a reverse transcriptase. Suitable reverse transcriptase proteins for the present invention may be obtained from various retroviruses including, without limitation, Moloney Murine Leukemia virus, Human Immunodeficiency Virus (HIV), Simian Immunodeficiency Virus (SIV), and retrons isolated from various yeast and bacterial species. Preferably, the reverse transcriptase is from Moloney Murine Leukemia virus.

It will be appreciated by those skilled in the art that reverse transcriptases typically contain a domain conferring RNase H activity. In accordance with the present invention, the reverse transcriptase may or may not possess such RNase H activity. Thus, the RNA-degrading enzyme used in the present methods and kits may be an RNase H activity associated with the reverse transcriptase or may be a separate RNA-degrading enzyme known in the art to degrade RNA in a DNA/RNA duplex to produce ssDNA including, but not limited to, RNase H.

Additional in vitro methods may also be used to produce the ssDNA of the present invention. Suitable methods include: asymmetric PCR (See, e.g., U.S. Pat. No. 8,735,067), PCR using two oligonucleotide primers, one present in limiting concentration (See, e.g., U.S. Pat. No. 5,066,584), and use of "nickase" and/or restriction endonucleases enzymes to produce ssDNA from dsDNA molecules (See, e.g., LsODN Preparation Kit—Biodynamics Laboratory Inc., Tokyo, Japan).

The efficiency of ssDNA-based insertion may also be affected by the secondary structure of the ssDNA. Such secondary structure may be prevented or minimized by using strategies that reduce the secondary structure present in ssDNA repair templates. Thus, the compositions, methods, and kits of the present invention may further include, without limitation, buffers (or use of buffers) that minimize secondary structure, proteins (or use of proteins) that reduce secondary structure such as ssDNA binding proteins, or modified nucleotides (or use of modified nucleotides) such as N4-ethyldeoxycytidine (d° C.).

The ssDNA of the present invention may include an exogenous sequence. As used herein, an "exogenous sequence" or "exogenous polynucleotide" refers to polynucleotides that are introduced into a cell.

The exogenous sequence may have a length of at least about 200, 250, 300, 350, 400, 450, 500 and 1,500, 2,000, 5,000, 10,000, 15,000, 20,000, or 30,000, or the exogenous sequence may have a length within a range bounded by any of these nucleotide lengths (e.g., a length of 200-1000 nucleotides).

The exogenous sequence may include any given sequences including those that may be artificially designed or modified. The exogenous sequence may encode a protein product, an RNA product, a DNA regulatory element, a variant DNA sequence, or any combinations thereof.

Protein products may be full-length proteins, fragments of proteins such as exons, fusion proteins, polypeptides, or peptides. The protein products may be expressed (e.g., exogenous sequence is transcribed and translated to produce protein product) when the exogenous sequence is introduced into the cell and/or introduced into the target DNA sequence. The protein products may become part of a fusion protein that becomes expressed in the cell when the exogenous sequence is introduced into the target DNA sequence or may be expressed as individual proteins. Exemplary protein products include, without limitation, fluorescent proteins such as eGFP, Cre proteins, Flp proteins, reverse tetracycline-controlled transactivator (rtTA) proteins, tetracycline-controlled transactivator (tTA) proteins, or epitope tag proteins such as CBP, FLAG, GST, HA, HBH, MBP, Myc, poly His, S-tag, SUMO, TAP, TRX, or V5 tags.

As used herein, the terms "protein" or "polypeptide" or "peptide" may be used interchangeably to refer to a polymer of amino acids. A "polypeptide" as contemplated herein typically comprises a polymer of naturally occurring amino acids (e.g., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine). The proteins contemplated herein may be further modified in vitro or in vivo to include non-amino acid moieties. These modifications may include but are not limited to acylation (e.g., O-acylation (esters), N-acylation (amides), S-acylation (thioesters)), acetylation (e.g., the addition of an acetyl group, either at the N-terminus of the protein or at lysine residues), formylation, lipoylation (e.g., attachment of a lipoate, a C8 functional group), myristoylation (e.g., attachment of myristate, a C14 saturated acid), palmitoylation (e.g., attachment of palmitate, a C16 saturated acid), alkylation (e.g., the addition of an alkyl group, such as an methyl at a lysine or arginine residue), isoprenylation or prenylation (e.g., the addition of an isoprenoid group such as farnesol or geranylgeraniol), amidation at C-terminus, glycosylation (e.g., the addition of a glycosyl group to either asparagine, hydroxylysine, serine, or threonine, resulting in a glycoprotein). Distinct from glycation, which is regarded as a non-enzymatic attachment of sugars, polysialylation (e.g., the addition of polysialic acid), glypiation (e.g., glycosylphosphatidylinositol (GPI) anchor formation, hydroxylation, iodination (e.g., of thyroid hormones), and phosphorylation (e.g., the addition of a phosphate group, usually to serine, tyrosine, threonine or histidine).

The exogenous sequence may encode an RNA product. RNA products may be expressed (i.e., when the exogenous sequence is transcribed to produce RNA product) when the exogenous sequence is introduced into the cell and/or introduced into the target DNA sequence. The RNA products may include RNAs involved in protein synthesis, RNAs involved in post-transcriptional modification or DNA replication, or regulatory RNAs. RNAs involved in protein synthesis may include, without limitation, mRNAs, rRNAs, tRNAs, or SRP RNAs. RNAs involved in post-transcriptional modification may include, without limitation, snRNAs, snoRNAs, or Y RNAs. Regulatory RNAs may include, without limitation, antisense RNAs, CRISPR RNAs, guide RNAs, long noncoding RNAs, microRNAs, siRNAs, piRNAs, tasiRNAs, 5'UTR sequences, 3'UTR sequences, RNA splicing regulatory sequences, IRES sequences, or polyA signal sequences.

The exogenous sequence may encode DNA regulatory elements. DNA regulatory elements may be non-coding DNA sequences that regulate the transcription of genes or serve as recognition sequences for protein products or RNA products. Exemplary DNA regulatory elements may include, without limitation, promoters, enhancers, silencers, insulators, tissue-specific regulatory elements, or recognition sequences for protein products or RNA products. Recognition sequences for protein products or RNA products may include, without limitation, recognition sequences for site-specific recombinases or integrases such as FRT, loxP, rox, and attB/attP sequences. Promoters useful in the practice of the present invention include, without limitation, constitutive, inducible, temporally-regulated, developmentally regulated, chemically regulated, physically regulated (e.g., light regulated or temperature-regulated), tissue-preferred, and tissue-specific promoters. Promoters may include pol I, pol II, or pol III promoters. Suitable promoters for expression in plants include, without limitation, the 35S promoter of the cauliflower mosaic virus, ubiquitine, tCUP cryptic constitutive promoter, the Rsyn7 promoter, pathogen-inducible promoters, the maize In2-2 promoter, the tobacco PR-1a promoter, glucocorticoid-inducible promoters, estrogen-inducible promoters and tetracycline-inducible and tetracycline-repressible promoters. Other promoters include the T3, T7 and SP6 promoter sequences. In mammalian cells, typical promoters include, without limitation, promoters for Rous sarcoma virus (RSV), human immunodeficiency virus (HIV-1), cytomegalovirus (CMV), SV40 virus, and the like as well as the translational elongation factor EF-1α promoter or ubiquitin promoter. Those of skill in the art are familiar with a wide variety of additional promoters for use in various cell types.

The exogenous sequence may encode a "variant DNA sequence." As used herein, a "variant DNA sequence" refers to a DNA molecule having a sequence that differs from a reference DNA sequence. A variant DNA sequence may include one or more copies of a DNA sequence that creates a repetitive (repeat) sequence or copy number variegation when the variant DNA sequence is inserted at a target DNA sequence. A variant DNA sequence may have 1, 2, 3, 4, 5, 6, 7, 8, 9, 10, or more insertions, deletions, or substitutions of a nucleotide base(s) relative to a reference molecule such as a target DNA sequence. For example, a variant DNA sequence may have one or more insertions, deletions, or substitutions of at least one nucleotide base(s) relative to the DNA sequence that is sought to be modified by introducing the exogenous sequence into the target DNA sequence of the cell.

The exogenous sequence may encode any combination of protein products, RNA products, or DNA regulatory elements described herein. For example, in creating conditional knockout organisms, a person of ordinary skill would appreciate that it may be preferable to create exogenous sequences that encode protein products such as exons and DNA regulatory elements such as recognition sequences for site-specific recombinases.

In some embodiments, the exogenous sequence of the ssDNA of the present invention may encode a microRNA. As known in the art, microRNAs are small non-coding RNA molecules that function in RNA silencing and post-transcriptional regulation of gene expression that may be derived from pri-miRNA and pre-miRNA precursors. MicroRNAs may be naturally-occurring or artificial. Artificial microRNAs (amiRNA) are microRNAs that have been genetically engineered to specifically modify the expression of a single or multiple genes of interest. As used herein, "modifying" gene expression may include increasing or decreasing gene expression. In some embodiments, the amiRNA decreases (e.g., "knocks-down") expression of a single or multiple genes of interest. Methods for designing amiRNAs are known in the art. See, e.g., BLOCK-iT RNAi designer (Invitrogen, Carlsbad, Calif.).

In some embodiments, the exogenous sequence of the ssDNA of the present invention may encode an amiRNA. Optionally, the encoded amiRNA may be flanked by two site-specific recombinase target sequences. Suitable site-specific recombinase target sequences include, without limitation, FRT and loxP sequences. In some embodiments, the two site-specific recombinase target sequences are inversely-oriented. In some embodiments of the present methods, the methods may further include expressing or introducing a site-specific recombinase that recognizes the site-specific recombinase target sequences into the cell. Suitable site-specific recombinases include, without limitation, FLP and Cre. Preferably, the two site-specific recombinase target sequences are loxP sites and the site-specific recombinase is a Cre protein.

The nuclease system of the present invention includes any rare-cutting endonuclease system capable of cutting a target DNA sequence in a genome or other DNA within a cell. The nuclease system includes a rare-cutting endonuclease that generally can be distinguished from other endonucleases (e.g., restriction enzymes) that may cut at several locations in a genome. The nuclease system may also include a guide polynucleotide that directs the endonuclease to a specific polynucleotide sequence. The nuclease system may produce a double strand break at the target DNA sequence or may nick the target DNA sequence. Nuclease systems such as engineered meganucleases, zinc finger nucleases (ZFN), transcription activator-like effector nucleases (TALEN), Argonaute nuclease systems, and CRISPR/Cas systems, are known in the art. The nuclease system of the present invention is preferably selected from the group consisting of zinc finger nucleases (ZFN), transcription activator-like effector nucleases (TALEN), Argonaute nuclease systems, and CRISPR/Cas systems. ZFNs and TALENs are artificial endonuclease proteins that can bind and cut DNA at specific sequences. The structure and functionality of ZFNs and TALENs are known in the art. See, e.g., Carlson et al., *Molecular Therapy Nucleic Acids* 1(1):e3 (2012).

CRISPR stands for "Clustered Regularly Interspaced Short Palindromic Repeats." A Cas protein, such as Cas9, is a nuclease discovered in bacteria that can bind and cut DNA at specific sequences by means of a single-guide RNA (sgRNA). Several CRISPR/Cas systems are known in the art (See, e.g., US Patent Publication No. 20140170753, 20140234972; Mali et al., *Science* 339(6121): 823-826 (2013); Cong et al., *Science* 339(6121):819-823; Shmakov et al., *Molecular Cell* 60:1-13 (2015)). Preferably, the nuclease system of the present invention includes a CRISPR/Cas system. In some preferred embodiments, the CRISPR/Cas system comprises a CRISPR/Cas9 system.

Argonaute nuclease systems include an endonuclease from the Argonaute protein family and a single-stranded guide DNAs that targets the endonuclease to a specific DNA sequence resulting in sequence-specific DNA cleavage. See, e.g., Gao et al., DNA-guided genome editing using the *Natronobacterium gregoryi* Argonaute *Nature Biotechnology*, published online May 2, 2016.

The endonuclease of the nuclease system may be a protein or encoded by a polynucleotide (e.g., DNA or RNA). The guide polynucleotide of the nuclease system may be a polynucleotide (e.g., DNA or RNA).

In embodiments that include CRISPR-Cas nuclease systems, the Cas endonuclease may be a protein or encoded in polynucleotide (e.g., DNA or RNA). The guide RNA may be composed of single-stranded RNA or encoded in a DNA polynucleotide. The guide RNA may include a single guide RNA or an annealed 2-part synthetic crRNA and tracrRNA molecule (See, e.g., Alt-R™ CRISPR guide RNAs, Integrated DNA Technologies).

In embodiments that include Argonaute nuclease systems, the Argonaute endonuclease may be a protein or encoded in a polynucleotide (e.g., DNA or RNA). The guide DNA may be single-stranded DNA and may be phosphorylated at its 5' terminus.

As used herein, "expressing" a nuclease system in a cell refers to transcribing or translating a polynucleotide encoding the nuclease system in the cell. The polynucleotide may be present in an expression construct, an expression vector for propagating the polynucleotide, or may integrated into the genome of the cell.

The compositions, methods, and kits disclosed herein may be used to modify a target DNA sequence in a cell. Suitable cells include prokaryotic cells and eukaryotic cells. Eukaryotic cells may include protist cells, fungi cells, plant cells, and animal cells. Suitable eukaryotic cells include cells from popular model organisms including, but not limited to, *Saccharomyces cerevisiae, Caenorhabditis elegans, Drosophila melanogaster, Danio rerio, Mus musculus*, and *Rattus norvegicus*.

The cell may exist in an organism or a subject or may exist outside an organism or subject such as in a cell culture. Suitable organisms include fungi, plants, or other eukaryotic organisms such as animals. In some embodiments, the organism may be a mammal including, but not limited to, a mouse, rat, or human. In some embodiments, the organism may be a popular model organism including, but not limited to, *Saccharomyces cerevisiae, Caenorhabditis elegans, Drosophila melanogaster, Danio rerio, Mus musculus*, and *Rattus norvegicus*.

The cell may be a mammalian cell such as, without limitation, a mouse cell, a rat cell, or a human cell. The cell may be a stem cell (e.g., an embryonic stem cell, an induced pluripotent stem cell, or a non-human embryo containing one or more cells). In some embodiments, the cell is a mouse embryo transplanted into the oviducts of pseudo-pregnant female mouse following modification. In some embodiments, the cell was removed from a subject prior to modification.

As used herein, the term "subject" and "patient" are used interchangeably herein and refer to both human and nonhuman animals. The term "nonhuman animals" of the disclosure includes all vertebrates, e.g., mammals and non-mammals, such as nonhuman primates, sheep, dog, cat, horse, cow, pig, mice, rats, chickens, amphibians, reptiles, and the like. In some embodiments, the subject is a human patient. The subject may be a human patient in need of genetically-modified cells.

Compositions for Modifying a Target DNA Sequence

Compositions for modifying a target DNA sequence in a cell are provided. The compositions may include single-stranded DNA (ssDNA). The compositions may also include (a) single-stranded DNA (ssDNA) and (b) a nuclease system capable of cutting the target DNA sequence. The ssDNA may include a 5' homology arm having substantial sequence identity to the target DNA sequence, an exogenous sequence, and a 3' homology arm having substantial sequence identity to the target DNA sequence.

Delivery particles comprising ssDNA compositions are also contemplated. The delivery particles may include any one of the compositions disclosed herein. Delivery particles suitable for delivering polynucleotides and/or proteins are known in the art and may include, without limitation, polymeric particles, liposomal particles, and particles including lipids and at least one type of polymer. In some embodiments, the delivery particles may be formed using common Lipofectamine reagents such as, without limitation, the Lipofectamine RNAiMAX™ Transfection Reagent (Thermo Fisher Scientific).

The delivery particles may include nanoscale particles and/or microscale particles, for example, as delivery vehicles of components to a cell for genome editing. The particles may have an effective average diameter less than about 500 μm, 100 μm, 50 μm, 20 μm, 10 μm, 5 μm, 2 μm, 1 μm, 0.5 μm, 0.2 μm, 0.1 μm, 0.05 μm, 0.02 μm, 0.01 μm, or have an effective average diameter within a range bounded by any of 500 μm, 100 μm, 50 μm, 20 μm, 10 μm, 5 μm, 2 μm, 1 μm, 0.5 μm, 0.2 μm, 0.1 μm, 0.05 μm, 0.02 μm, 0.01 μm (e.g., 0.01-5 μm). The nanoscale particles and microscale particles may be referred to as "nanoparticles" and "microparticles," respectively.

Polymeric particles have been described in the art. (See, e.g., Reis et al., Nanomedicine 2 (1) (2006) 8-21; Kumari et al., Colloids and Surfaces B: Biointerfaces 75 (2010) 1-18; and U.S. Patent Publication 20140066388). Polymeric particles may include or may be formed from biodegradable polymeric molecules, which in some embodiments may include dendrimers. Suitable dendrimers may include, but are not limited to, polyamidoamine (PAMAM) dendrimers. Polyamidoamine dendrimers have been used in the art as vehicles for intracellular delivery of therapeutics. (See Esfand et al., Drug Discov. Today (2001) 6(8):427-436; and Bharali, International Journal of Nanomedicine (2009) 4:1-7). Polyamidoamine dendrimers suitable for preparing the presently disclosed nanoparticles may include 3rd-, 4th-, 5th-, or preferably at least 6th-generation dendrimers.

Polymeric particles may also include or may be formed from other biodegradable polymeric molecules which may include, without limitation, polylactic acid (PLA), polygycolic acid (PGA), co-polymers of PLA and PGA (e.g., polyactic-co-glycolic acid (PLGA)), poly-ε-caprolactone (PCL), polyethylene glycol (PEG), poly(3-hydroxybutyrate), poly(p-dioxanone), polypropylene fumarate, poly (orthoesters), polyol/diketene acetals addition polymers, poly-alkyl-cyano-acrylates (PAC), poly(sebacic anhydride) (PSA), poly(carboxybiscarboxyphenoxyphenoxy hexone (PCPP) poly[bis (p-carboxypheonoxy)methane](PCPM), copolymers of PSA, PCPP and PCPM, poly(amino acids), poly(pseudo amino acids), polyphosphazenes, derivatives of poly[(dichloro)phosphazenes] and poly[(organo)phosphazenes], poly-hydroxybutyric acid, or S-caproic acid, elastin, gelatin, and chitosan. (See, e.g., Kumari et al., Colloids and Surfaces B: Biointerfaces 75 (2010) 1-18: and U.S. Pat. Nos. 6,913,767; 6,884,435; 6,565,777; 6,534,092; 6,528,087; 6,379,704; 6,309,569; 6,264,987; 6,210,707; 6,090,925; 6,022,564; 5,981,719; 5,871,747; 5,723,269; 5,603,960; and 5,578,709; and U.S. Published Application No. 2007/0081972; and International Application Publication Nos. WO 2012/115806; and WO 2012/054425). In some embodiments, the particles may include a mixture of PLGA and PAMAM.

Polymeric particles may be prepared by methods known in the art. (See. e.g., Nagavarma et al., Asian J. of Pharma. And Clin. Res., Vol 5, Suppl 3, 2012, pages 16-23; Cismaru et al., Rev. Roum. Chim., 2010, 55(8). 433-442; and International Application Publication Nos. WO 2012/115806; and WO 2012/054425). Suitable methods for preparing the nanoparticles may include methods that utilize a dispersion of a preformed polymer, which may include but are not limited to solvent evaporation, nanoprecipitation, emulsification/solvent diffusion, salting out, dialysis, and supercritical fluid technology. In some embodiments, the nanoparticles may be prepared by forming a double emulsion (e.g., water-in-oil-in-water) and subsequently performing solvent-evaporation. The nanoparticles obtained by the disclosed methods may be subjected to further processing steps such as washing and lyophilization, as desired. Optionally, the nanoparticles may be combined with a preservative (e.g., trehalose).

Micelle and liposomal-based particles may also serve as suitable delivery particles. See, e.g., U.S. Pat. No. 8,252,324. Micelles are self-assembling spherical colloidal nanoparticles formed by amphiphilic molecules. Micelles are also described as aggregate surfactant molecules disbursed in a liquid colloid. The core of the micelle, which is segregated in an aqueous milieu, is capable of encapsulating polynucleotides and/or proteins protecting them from destruction and biological surroundings while improving their pharmacokinetics and biodistribution. Micelles are generally in the order of 5-50 nm in diameter, and are therefore capable of accumulating in pathological areas with leaky vasculature, such as infarct zones and tumors due to the enhanced permeability and retention effect. Micelles are also capable of evading a major obstacle in drug targeting by particulate systems: non-specific uptake by the reticuloendothelial systems and renal secretion.

Micelles may be formed by any of commonly known surfactants, such as sodium dodecylsulfate or phospholipids, but the performance of such surfactants as drug delivery systems is low compared to micelles composed of specially designed block copolymers, as described in Kataoka et al., supra and Torchilin et al., supra (2003). The flexible hydrophilic polymers, which are used as shell-forming segments for the polymer micelles, assemble into a dense palisade shell, which is cross-linked by numerous water molecules to achieve effective stabilization of the vesicle. Accordingly, the polymer micelles dissociate much more slowly than unmodified surfactant micelles, retain the loaded drugs for a longer period of time and accumulate the drug at the target site more efficiently. Further, polymer micelles are readily engineered to have sizes in the range of several tens of nanometers with a narrow size distribution which is a great advantage in regulating biodistribution.

In contrast to micelles, liposomes are bilayered phospholipid vesicles approximately 50 to 1,000 nm in diameter. Liposomes are biologically inert and completely biocompatible; they cause practically no toxic or antigenic reactions. Polynucleotides and/or proteins included in liposomes are protected from the destructive action of the external media by the liposomes. Thus, liposomes are able to deliver their content inside cells and even inside different cell compartments. Generally, liposomes are considered a promising carrier with significant therapeutic potential, as demonstrated in numerous laboratory tests and clinical trials, e.g., Torchilin, Nat. Rev. Drug discov. 4, 145-160 (2005).

It is known that liposomes and micelles can be stabilized by enhancing the outermost hydrophobic shell with water soluble polymers, such as polyethyleneglycol (PEG). The presence of hydrophilic polymers on the hydrophobic surface of these carrier particles attracts a water shell, resulting in reduced adsorption of opsonins to the carrier particles. This, in turn, results in a decrease in both the rate and extent of uptake of carrier particles by mononuclear phagocytes. Long circulating liposomes improved the therapeutic index of drugs and encapsulated therein. Currently, several preparations based on long circulating liposomes are commercially available, for example, Doxil®, a doxorubicin containing polyethyleneglycolated (PEGylated) liposomes, Sharp et al., Drugs 62 2089-2126 (2002). Doxil is manufactured by ortho biotech products, LP of bridgewater, N.J., USA. O'Shaughnessy, Clin. Breast cancer 4, 318-328. (2003), demonstrated selective delivery of doxorubicin into solid tumors in patients with breast carcinoma metastases was achieved by capsulation of the drug into PEGylated liposomes, which resulted in subsequent improvement of survival. Efficacy was also demonstrated by combining liposomal doxorubicin with paclitaxel (available as Taxol®, Bristol-Meyers Squibb Company, New York, N.Y., USA) caelyx (Schering-Plough corporation, Kenilworth, N.J., USA) and carboplatin (available as Paraplatin® from Bristol-Meyers Squibb company). Several preparations of liposomes have been approved for clinical application or undergoing clinical evaluation, Torchilin, supra. (2005).

Exemplary delivery particles for delivery of components of the CRISPR/Cas system have also been disclosed in, for example, U.S. Patent Publication No. 20150232883 and WO Patent Publication Nos. 2014/093635 and 2015/089351. In some embodiments, the delivery particles comprise 1,2-dioleoyl-3-trimethylammonium-propane (DOTAP), 1,2-ditetradecanoyl-sn-glycero-3-phosphocholine (DMPC), polyethylene glycol (PEG), cholesterol, or any combination thereof.

Delivery particles may also include particles including lipids and polymer components. For example, particles including a phospholipid bilayer and poly(beta-amino ester) (PBAE) have been developed for the in vivo delivery of polynucleotides. See, e.g., Su et al., *Molecular Pharmaceutics,* 8(3):774-787 (2011).

The delivery particles may include a surfactant which may include a cationic surfactant. Suitable cationic surfactants may include but are not limited to quaternary ammonium compounds, for example, quaternary ammonium compounds or salts thereof having a formula $(X)_3N+(CH_2)(CH_3)$ where X is $C_{1-6}$ alkyl or aryl, and n=(9, 11, 13, 15, or 17). Suitable salts of the quaternary ammonium compounds may include halide salts (e.g., Cl⁻ or Br⁻ salts) such as cetyltrimethylammonium bromide (CTAB).

The delivery particles preferably have physical properties that facilitate uptake by a targeted cell. For example, preferably the particles have a size and a charge that that facilitate uptake by a targeted cell. Typically, the particles have a mean effective diameter of less than 1 micron, and preferably the particles have a mean effective diameter of between about 25 nm and about 500 nm, and more preferably between about 50 nm and about 250 nm, and most preferably about 100 nm to about 150 nm. The size of the particles (e.g., mean effective diameter) may be assessed by known methods in the art, which may include but are not limited to transmission electron microscopy (TEM), scanning electron microscopy (SEM), Atomic Force Microscopy (AFM), Photon Correlation Spectroscopy (PCS), Nanoparticle Surface Area Monitor (NSAM). Condensation Particle Counter (CPC), Differential Mobility Analyzer (DMA), Scanning Mobility Particle Sizer (SMPS), Nanoparticle Tracking Analysis (NTA), X-Ray Diffraction (XRD), Aerosol Time of Flight Mass Spectroscopy (ATFMS), and Aerosol Particle Mass Analyzer (APM).

The disclosed delivery particles preferably have a zeta-potential that facilitates uptake by a target cell. Typically, the particles have a zeta-potential greater than 0. In some embodiments, the nanoparticles have a zeta-potential between about 5 mV to about 45 mV, between about 15 mV to about 35 mV, or between about 20 mV and about 30 mV. Zeta-potential may be experimental determined via characteristics that include electrophoretic mobility or dynamic electrophoretic mobility. Electrokinetic phenomena and electroacoustic phenomena may be utilized to calculate zeta-potential.

Delivery particles will be taken up by cells non-specifically even if the particles do not include a specific ligand on their surface. However, the disclosed delivery particles may be configured to also include a ligand that specifically targets a particular cell type. In order to achieve more specific targeting of delivery particles, such particles may be modified with various ligands using advance conjugation procedures. For example, antibodies and small peptides have been attached to the water exposed tips of polyethyleneglycol chains, Blume, et al. Biomembranes 1149, 180-184 (1993). Antibodies and small peptides have also been conjugated via reactive p-nitrophenylcarbonyl, N-benzotrazole carbonyl or maleimide terminated PEG-phosphatidylethanolamine, Moreira. Pharm. Res. 19, 265-269 (2002); Torchilin et al., supra (2001); xiong, et al., J. Pharm. Sci. 94, 1782-1793 (2005).

Delivery Particle Methods

One aspect of the present invention provides a method of modifying a target DNA sequence in a cell including contacting the cell with any one of the delivery particles disclosed herein in an amount effective to allow delivery of the disclosed compositions into the cell and modification of the target DNA sequence. In such methods, the cells may be contacted with the delivery particles directly or indirectly in vivo, in vitro, in situ, or ex vivo. On an in vivo basis, the contact with the cells of the subject takes place within the body of the individual in accordance with the procedures which are most typically employed.

The term "amount effective" or "therapeutically effective amount" refers to an amount sufficient to effect beneficial or desirable biological and/or clinical results. The therapeutically effective amount will vary depending on the compound, formulation or composition, the disease and its severity and the age, weight, physical condition and responsiveness of the subject to be treated. The present compositions are preferably comprised within delivery particle for administration to a human or non-human mammalian patient. Suitable delivery particles may be readily selected by one of skill in the art and may depend on the route of administration chosen.

The ssDNA and nuclease system may be delivered in the same delivery particle or in separate delivery particles. Likewise, the components of the nuclease system may be delivered in the same delivery particle or separate delivery particles. For example, with regards to a CRISPR/Cas system, the Cas enzyme (e.g., Cas9) (protein, RNA, or DNA) and guide RNA may be delivered in the same delivery particle or may be delivered in separate delivery particles.

The nuclease system and the ssDNA may be administered together. Alternatively, the nuclease system can be delivered prior to the ssDNA to give time for nuclease system to be expressed. In some embodiments, the nuclease system might be administered 1-12 hours (preferably around 2-6 hours) prior to the administration of the ssDNA. Furthermore, additional administrations of ssDNA and/or nuclease system might be useful to achieve sufficient levels of DNA modification or genome modification.

The delivery particles may also be present in pharmaceutical compositions that may contain pharmaceutically acceptable components, such as excipients, carriers and/or stabilizers. Such components include any pharmaceutical agent that does not itself induce an immune response harmful to the individual receiving the composition, and which may be administered without undue toxicity. Pharmaceutically acceptable components include, but are not limited to, liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. Other exemplary components include lactose, sucrose, calcium phosphate, gelatin, dextran, agar, pectin, peanut oil, sesame oil, and water. The selection of the carrier is not a limitation of the present invention. Optionally, the compositions of the present disclosure may comprise, in addition to ssDNA and a nuclease system, other conventional pharmaceutical ingredients, such as preservatives, chemical stabilizers and the like. Suitable exemplary ingredients include microcrystalline cellulose, carboxymethylcellulose sodium, polysorbate 80, phenylethyl alcohol, chlorobutanol, potassium sorbate, sorbic acid, sulfur dioxide, propyl gallate, the parabens, ethyl vanillin, glycerin, phenol, parachlorophenol, gelatin and albumin. A thorough discussion of pharmaceutically acceptable excipients is available in REMINGTON'S PHARMACEUTICAL SCIENCES (Mack Pub. Co., N.J. 1991).

Appropriate doses will depend, among other factors, on the specifics of the delivery particle compositions chosen, on the route of administration, on the mammal being treated (e.g., human or non-human primate or other mammal), age, weight, sex, and general condition of the subject to be treated and the mode of administration. Thus, the appropriate dosage may vary from patient to patient. An appropriate effective amount can be readily determined by one of skill in the art. Dosage treatment may be a single dose schedule or a multiple dose schedule. Moreover, the subject may be administered as many doses as appropriate. One of skill in the art can readily determine an appropriate number of doses. However, the dosage may need to be adjusted to take into consideration an alternative route of administration, or balance the therapeutic benefit against any side effects. Such dosages may vary depending upon the therapeutic application for which the present compositions are employed.

The present delivery particles are administered in sufficient amounts to enter the desired cells and to guarantee sufficient levels of functionality of the transferred nucleic acid composition to provide a therapeutic benefit without undue adverse, or with medically acceptable, physiological effects which can be determined by those skilled in the medical arts.

The disclosed delivery particles may be administered in any suitable manner. However, in some embodiments, the delivery particles are present in a pharmaceutical composition that is administered via injection (e.g., intravenous injection, peritoneal injection, or subcutaneous injection). For example, the delivery particles may be combined with pharmaceutically acceptable carriers, diluents, or excipients that are suitable for injection such as saline, Ringer's solution, dextrose solution, and the like. The particular dosage regimen, i.e., dose, timing and repetition, will depend on the particular individual and that individual's medical history.

The pharmaceutical compositions disclosed herein may be manufactured by means that include, but are not limited to, mixing, granulating, dissolving, or lyophilizing processes.

Pharmaceutical compositions to be used for in vivo administration in the disclosed methods typically are sterile. Sterile compositions may be prepared, for example, by filtration through sterile filtration membranes.

Kits and Systems

Kits or Systems for modifying a target DNA sequence in a cell are also provided. The kits or systems may be used for performing any of the methods described herein. The kits or systems may include an RNA polymerase, a reverse tranzscriptase, an RNA-degrading enzyme, and a nuclease system. The kits or systems may further include instructions for performing any of the methods described herein. Optionally, the kits or systems may include a DNA vector comprising from 5' to 3' a promoter, a cloning site, and a restriction enzyme site. In some embodiments, the promoter is a T7, T3, or SP6 promoter. It will be appreciated that the reverse transcriptase and RNA-degrading enzyme may be part of the same enzyme as it is known that reverse transcriptases may have RNase activity.

In still another aspect, the kits or systems of the present invention include (a) single-stranded DNA (ssDNA) and (b) a nuclease system capable of cutting the target DNA sequence.

Engineered Eukaryotic Cells

Also disclosed herein are engineered or recombinant eukaryotic cells including DNA modified by the methods disclosed herein. In some embodiments, the engineered eukaryotic cells include amiRNAs. The engineered eukaryotic cells may include an exogenous DNA construct encoding an amiRNA. The DNA construct may be inserted into an intron of a gene. Preferably, the DNA construct is inserted into an evolutionarily non-conserved region of the intron. Such non-conserved regions are less likely to contain regulatory sequences and may be determined by comparing the intronic sequences among related species. In the Examples, the inventors compared the intronic regions of the mouse and human eEF-2 genes. Likewise, mouse intronic sequences could be compared to other mammals including, without limitation, rats. In some embodiments, the targeted mouse intronic DNA sequence shares no more than 80%, 70%, 60%, 50%, 40%, or 30% sequence identity with the comparable human intronic DNA sequence.

The gene may be endogenous to the cell (e.g., genome or other self-replicating form of DNA such as a plasmid endogenously found in the cell) or exogenous to the cell (e.g., transgenes or plasmids introduced in the cell). The gene may also be constitutively expressed or may be expressed in a tissue-specific manner. In some embodiments, the DNA construct is inserted into an intron of an endogenous eEF-2 gene. Suitably, the intron is intron 1 or intron 6 of the endogenous eEF-2 gene.

In some embodiments, the DNA construct lacks a promoter, reporter sequence, and/or a polyA tail. Such components are typically required in transgenic constructs made with conventional techniques. In the Examples, however, the inventors surprisingly demonstrate that these components are not required to knock down expression of particular genes when the amiRNA is specifically targeted to an intron.

Optionally, the encoded amiRNA in the engineered eukaryotic cells may be flanked by two site-specific recombinase target sequences. Suitable site-specific recombinase target sequences include, without limitation, FRT and loxP sequences. In some embodiments, the two site-specific recombinase target sequences are inversely-oriented. In some embodiments, the engineered eukaryotic cells may further include a site-specific recombinase that recognizes the site-specific recombinase target sequences in the cell.

Suitable site-specific recombinases include, without limitation, FLP and Cre. Preferably, the two site-specific recombinase target sequences are loxP sites and the site-specific recombinase is a Cre protein.

Suitable engineered eukaryotic cells include cells from popular model organisms including, but not limited to, *Saccharomyces cerevisiae, Caenorhabditis elegans, Drosophila melanogaster, Danio rerio, Mus musculus*, and *Rattus norvegicus*. In some embodiments, the engineered eukaryotic cell is a mammalian cell such as, without limitation, a mouse cell, a rat cell, or a human cell. In some embodiments, the engineered eukaryotic cell is a stem cell (e.g., an embryonic stem cell, an induced pluripotent stem cell, or a non-human embryo containing one or more cells). In some embodiments, the engineered eukaryotic cell is a mouse embryo transplanted into the oviducts of pseudo-pregnant female mouse following modification. In some embodiments, the engineered eukaryotic cell was removed from a subject prior to modification.

Eukaryotic organisms including any one of the disclosed engineered eukaryotic cells are also provided. Suitable eukaryotic organisms include fungi, plants, or other eukaryotic organisms. In some embodiments, the eukaryotic organism is a mammal including, but not limited to, a mouse, rat, or human. In some embodiments, the eukaryotic organism is a popular model organism including, but not limited to, *Saccharomyces cerevisiae, Caenorhabditis elegans, Drosophila melanogaster, Danio rerio, Mus musculus*, and *Rattus norvegicus*.

ILLUSTRATIVE EMBODIMENTS

The following embodiments are illustrative and should not be interpreted to limit the scope of the claimed subject matter.

Embodiment 1

A method for modifying a target DNA sequence in a cell, the method comprising: (a) introducing a single-stranded DNA (ssDNA) in the cell, the ssDNA comprising a 5' homology arm having substantial sequence identity to the target DNA sequence, an exogenous sequence, and a 3' homology arm having substantial sequence identity to the target DNA sequence, wherein the ssDNA is between 200 and 10,000 nucleotides in length, and (b) introducing or expressing a nuclease system in the cell, wherein the nuclease system cuts the target DNA sequence.

Embodiment 2

The method of embodiment 1, wherein the ratio of the length of the exogenous sequence to the total length of the 5' homology arm and the 3' homology arm (exogenous sequence length:homology arm length) is between 1.5:1 and 20:1.

Embodiment 3

The method of embodiment 2, wherein the exogenous sequence encodes a protein product, an RNA product, a DNA regulatory element, or a variant DNA sequence.

Embodiment 4

The method of any of the preceding embodiments, wherein the ssDNA is produced by a method comprising: (a) transcribing a DNA template encoding a promoter operably linked to nucleotide sequence comprising a 5' homology arm having substantial sequence identity to the target DNA sequence, an exogenous sequence, and a 3' homology arm having substantial sequence identity to the target DNA sequence to produce a RNA transcript, (b) synthesizing a ssDNA/RNA duplex by reverse transcription of the RNA transcript, and (c) degrading the RNA from the ssDNA/RNA duplex using an RNA-degrading enzyme to produce ssDNA.

Embodiment 5

The method of embodiment 5, further comprising purifying the ssDNA.

Embodiment 6

The method of any one of embodiments 4-5, wherein the promoter comprises a T7 promoter and the transcribing is performed using a T7 RNA polymerase.

Embodiment 7

The method of any one of embodiments 4-6, wherein the ssDNA/RNA duplex is synthesized using a reverse transcriptase and a primer.

Embodiment 8

The method of any one of embodiments 4-7, wherein the RNA-degrading enzyme comprises RNase H.

Embodiment 9

The method of any one of the preceding embodiments, wherein the 5' homology arm and the 3' homology arm are substantially identical to no more than 110 nucleotides of the target DNA sequence.

Embodiment 10

The method of any one of the preceding embodiments, wherein introducing a nuclease system in the cell comprises introducing into the cell a polynucleotide that encodes the nuclease system.

Embodiment 11

The method of any one of the preceding embodiments, wherein the nuclease system produces a double strand break at the target DNA sequence.

Embodiment 12

The method of embodiment 11, wherein the 5' homology arm is substantially identical to the target DNA sequence on one side of the double strand break and the 3' homology arm is substantially identical to the target DNA sequence on the other side of the double strand break.

Embodiment 13

The method of any one of the preceding embodiments, wherein the nuclease system is selected from the group consisting of a meganuclease, a zinc finger nuclease (ZFN), a transcription activator-like effector nuclease (TALEN), an Argonaute nuclease system, and a CRISPR/Cas system.

Embodiment 14

The method of any one of the preceding embodiments, wherein the nuclease system comprises a CRISPR/Cas system.

Embodiment 15

The method of any one of the preceding embodiments, wherein the CRISPR/Cas system comprises a CRISPR/Cas9 system.

Embodiment 16

The method of any one of the preceding embodiments, wherein the cell is a prokaryotic cell.

Embodiment 17

The method of any one of embodiments 1-15, wherein the cell is a eukaryotic cell.

Embodiment 18

The method of embodiment 17, wherein the cell is a mammalian cell.

Embodiment 19

The method of embodiment 18, wherein the cell is a mouse cell.

Embodiment 20

The method of embodiment 18, wherein the cell is a human cell.

Embodiment 21

The method of any one of embodiments 17-19, wherein the cell is a non-human one-cell embryo.

Embodiment 22

The method of embodiment 20, wherein the human cell was removed from a subject prior to modification.

Embodiment 23

The method of embodiment 21, wherein the one-cell embryo is a mouse embryo that is transplanted into the oviducts of a pseudo-pregnant female mouse following modification.

Embodiment 24

The method of any one of embodiments 17-22, wherein the cell is a stem cell.

Embodiment 25

The method of embodiment 24, wherein the cell is an embryonic stem cell.

Embodiment 26

The method of embodiment 24, wherein the cell is an induced pluripotent stem cell.

Embodiment 27

The method of any one of the preceding embodiments, wherein the exogenous sequence encodes an artificial microRNA (amiRNA).

Embodiment 28

The method of embodiment 27, wherein the amiRNA is flanked by two site-specific recombinase target sequences.

Embodiment 29

The method of embodiment 28, wherein the two site-specific recombinase target sequences are inversely-oriented.

Embodiment 30

The method of any one of embodiments 28-29, further comprising expressing or transfecting a site-specific recombinase that recognizes the site-specific recombinase target sequences in the cell.

Embodiment 31

The method of any one of embodiments 28-30, wherein the two site-specific recombinase target sequences comprise loxP sites.

Embodiment 32

The method of any one of embodiments 28-31, wherein the site-specific recombinase comprises a Cre protein.

Embodiment 33

The method of any one of the preceding embodiments, wherein the target DNA sequence is in an intron of a gene.

Embodiment 34

The method of embodiment 33, wherein the gene is constitutively expressed.

Embodiment 35

The method of any one of the preceding embodiments, wherein the target DNA sequence is endogenous to the cell and in the genome of the cell.

Embodiment 36

A composition for modifying a target DNA sequence in a cell, the composition comprising: (a) single-stranded DNA (ssDNA), the ssDNA comprising a 5' homology arm having substantial sequence identity to the target DNA sequence, an exogenous sequence, and a 3' homology arm having substantial sequence identity to the target DNA sequence, wherein the ssDNA is between 200 and 10,000 nucleotides in length, and (b) a nuclease system capable of cutting the target DNA sequence.

Embodiment 37

The composition of embodiment 36, wherein the ratio of the length of the exogenous sequence to the total length of the 5' homology arm and the 3' homology arm (exogenous sequence length:homology arm length) is between 1.5:1 and 20:1.

Embodiment 38

The composition of any one of embodiments 36-37, wherein the exogenous sequence encodes a protein product, an RNA product, a DNA regulatory element, or a variant DNA sequence.

Embodiment 39

The composition of any one of embodiments 36-38, wherein the 5' homology arm and the 3' homology arm are substantially identical to no more than 110 nucleotides of the target DNA sequence.

Embodiment 40

The composition of any one of embodiments 36-39, wherein the nuclease system comprises a polynucleotide that encodes the nuclease system.

Embodiment 41

The composition of any one of embodiments 36-40, wherein the nuclease system produces a double strand break at the target DNA sequence.

Embodiment 42

The composition of embodiment 41, wherein the 5' homology arm is substantially identical to the target DNA sequence on one side of the double strand break and the 3' homology arm is substantially identical to the target DNA sequence on the other side of the double strand break.

Embodiment 43

The composition of any one of embodiments 36-42, wherein the nuclease system is selected from the group consisting of a meganuclease, a zinc finger nuclease (ZFN), a transcription activator-like effector nuclease (TALEN), an Argonaute nuclease system, and a CRISPR/Cas system.

Embodiment 44

The composition of any one of embodiments 36-43, wherein the nuclease system comprises a CRISPR/Cas system.

Embodiment 45

The composition of any one of embodiments 36-44, wherein the CRISPR/Cas system comprises a CRISPR/Cas9 system.

Embodiment 46

The composition of any one of embodiments 36-45, wherein the exogenous sequence comprises an artificial microRNA (amiRNA).

Embodiment 47

The composition of embodiment 46, wherein the amiRNA is flanked by two site-specific recombinase target sequences.

Embodiment 48

The composition of embodiment 47, wherein the two site-specific recombinase target sequences are inversely-oriented.

Embodiment 49

The composition of any one of embodiments 47-48, wherein the two site-specific recombinase target sequences comprise loxP sites.

Embodiment 50

A delivery particle comprising the composition of any one of embodiments 36-49 or 88-89.

Embodiment 51

The delivery particle of embodiment 50, wherein the delivery particle is selected from the group consisting of polymeric particles, liposomal particles, and particles including lipids and at least one type of polymer.

Embodiment 52

A method of modifying a target DNA sequence in a cell comprising contacting the cell with the delivery particle of any one of embodiments 50-51 in an amount effective to allow delivery of the composition into the cell and modification of the target DNA sequence.

Embodiment 53

The method of embodiment 52, wherein the contacting occurs in vitro.

Embodiment 54

The method of embodiment 52, wherein the contacting occurs in vivo.

Embodiment 55

A kit for performing any one of the methods of embodiments 1-35.

Embodiment 56

A kit for modifying a target DNA sequence in a cell, the kit comprising an RNA polymerase, a reverse transcriptase, an RNA-degrading enzyme, and a nuclease system.

Embodiment 57

The kit of embodiment 56, further comprising a DNA vector comprising from 5' to 3' a T7 promoter, a cloning site, and a restriction enzyme site.

Embodiment 58

The kit of any one of embodiments 56-57, wherein the nuclease system is comprised of at least one polynucleotide encoding the nuclease system.

Embodiment 59

The kit of embodiment 58, wherein the nuclease system comprises DNA.

Embodiment 60

The kit of any one of embodiments 56-59, wherein the nuclease system comprises a CRISPR/Cas system.

Embodiment 61

The kit of embodiment 60, wherein the CRISPR/Cas system comprises a CRISPR/Cas9 system.

Embodiment 62

The kit of any one of embodiments 56-61, wherein the RNA polymerase comprises T7 RNA polymerase.

Embodiment 63

The kit of any one of embodiments 56-62, wherein the RNA-degrading enzyme comprises RNase H.

Embodiment 64

A kit for modifying a target DNA sequence in a cell, the kit comprising: (a) single-stranded DNA (ssDNA), the ssDNA comprising a 5' homology arm having substantial sequence identity to the target DNA sequence, an exogenous sequence, and a 3' homology arm having substantial sequence identity to the target DNA sequence, wherein the ssDNA is between 200 and 10,000 nucleotides in length, and (b) a nuclease system capable of cutting the target DNA sequence.

Embodiment 65

The kit of embodiment 64, wherein the ratio of the length of the exogenous sequence to the total length of the 5' homology arm and the 3' homology arm (exogenous sequence length:homology arm length) is between 1.5:1 and 20:1.

Embodiment 66

The kit of any one of embodiments 64-65, wherein the exogenous sequence encodes a protein product, an RNA product, a DNA regulatory element, or a variant DNA sequence.

Embodiment 67

The kit of any one of embodiments 64-66, wherein the 5' homology arm and the 3' homology arm are substantially identical to no more than 110 nucleotides of the target DNA sequence.

Embodiment 68

The kit of any one of embodiments 64-67, wherein the nuclease system produces a double strand break at the target DNA sequence.

Embodiment 69

The kit of any one of embodiments 64-68, wherein the nuclease system is selected from the group consisting of a meganuclease, a zinc finger nuclease (ZFN), a transcription activator-like effector nuclease (TALEN), an Argonaute nuclease system, and a CRISPR/Cas system.

Embodiment 70

The kit of any one of embodiments 64-69, wherein the nuclease system comprises a CRISPR/Cas system.

Embodiment 71

The kit of embodiment 70, wherein the CRISPR/Cas system comprises a CRISPR/Cas9 system.

Embodiment 72

An engineered eukaryotic cell comprising an exogenous DNA construct comprising an artificial microRNA (amiRNA), the exogenous DNA construct inserted into an intron of a gene.

Embodiment 73

The eukaryotic cell of embodiment 72, wherein the gene is constitutively expressed.

Embodiment 74

The eukaryotic cell of any one of embodiments 72-73, wherein the exogenous DNA construct lacks a promoter.

Embodiment 75

The eukaryotic cell of any one of embodiments 72-74, wherein the exogenous DNA construct lacks a reporter sequence.

Embodiment 76

The eukaryotic cell of any one of embodiments 72-75, wherein the exogenous DNA construct lacks a polyA tail.

Embodiment 77

The eukaryotic cell of any one of embodiments 72-76, wherein the gene is endogenous to the cell and in the genome of the cell.

Embodiment 78

The eukaryotic cell of any one of embodiments 72-77, wherein the amiRNA is flanked by two site-specific recombinase target sequences.

Embodiment 79

The eukaryotic cell of embodiment 78, wherein the two site-specific recombinase target sequences are inversely-oriented.

Embodiment 80

The eukaryotic cell of any one of embodiments 78-79, further comprising a site-specific recombinase that recognizes the site-specific recombinase target sequences in the cell.

Embodiment 81

The eukaryotic cell of any one of embodiments 78-80, wherein the two site-specific recombinase target sequences comprise loxP sites.

Embodiment 82

The eukaryotic cell of any one of embodiments 78-81, wherein the site-specific recombinase comprises a Cre protein.

Embodiment 83

The eukaryotic cell of any one of embodiments 72-82, wherein the eukaryotic cell is a mammalian cell.

Embodiment 84

The eukaryotic cell of embodiment 83, wherein the mammalian cell is a mouse cell.

Embodiment 85

The eukaryotic cell of any one of embodiments 72-84, wherein the DNA construct is inserted into an intron of an endogenous eEF-2 gene.

Embodiment 86

The eukaryotic cell of embodiment 85, wherein the intron is intron 6 of the endogenous eEF-2 gene.

Embodiment 87

A mammal comprising any one of the eukaryotic cells of embodiments 72-86.

Embodiment 88

A ssDNA comprising a 5' homology arm having substantial sequence identity to a target DNA sequence in a cell, an exogenous sequence, and a 3' homology arm having substantial sequence identity to the target DNA sequence, wherein the ssDNA is between 200 and 10,000 nucleotides in length, and wherein the ratio of the length of the exogenous sequence to the total length of the 5' homology arm and the 3' homology arm (exogenous sequence length: homology arm length) is between 1.5:1 and 20:1.

Embodiment 89

The ssDNA of embodiment 88, wherein the exogenous sequence encodes a protein product, an RNA product, a DNA regulatory element, or a variant DNA sequence.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. The applicants reserve the right to challenge the accuracy and pertinence of any of the documents cited herein.

EXAMPLES

The following Examples are illustrative and are not intended to limit the scope of the claimed subject matter.

Example 1

Reference is made to Miura et al., "CRISPR/Cas9-based generation of knockdown mice by intronic insertion of artificial microRNA using longer single-stranded DNA" *Scientific Reports* 5, Article number: 12799, doi:10.1038/srep12799 (2015) pages 1-11, Aug. 5, 2015 including supplemental information, the contents of which are incorporated herein by reference.

Abstract

Knockdown mouse models, where gene dosages can be modulated, provide valuable insights into gene function. Typically, such models are generated by embryonic stem (ES) cell-based targeted insertion, or pronuclear injection, of the knockdown expression cassette. However, these methods are associated with laborious and time-consuming steps, such as the generation of large constructs with elements needed for expression of a functional RNAi-cassette, ES-cell handling, or screening for mice with the desired knockdown effect. Here, we demonstrate that reliable knockdown models can be generated by targeted insertion of artificial microRNA (amiRNA) sequences into a specific locus in the genome [such as intronic regions of endogenous eukaryotic translation elongation factor 2 (eEF-2) gene] using the Clustered Regularly Interspaced Short Palindromic Repeats/Crispr associated 9 (CRISPR/Cas9) system. We used in vitro synthesized single-stranded DNAs (about 0.5-kb long) that code for amiRNA sequences as repair templates in CRISPR/Cas9 mutagenesis. Using this approach we demonstrate that amiRNA cassettes against exogenous (eGFP) or endogenous [orthodenticle homeobox 2 (Otx2)] genes can be efficiently targeted to a predetermined locus in the genome and result in knockdown of gene expression. We also provide a strategy to establish conditional knockdown models with this method.

Introduction

The study of gene functions in mice is generally achieved by disrupting the gene to generate a knockout model, and the animal is subjected to phenotypic analysis to understand the effects of complete loss of a given protein. Studying the effects of intermediate levels of protein loss can also provide valuable insights into gene function during development and disease, especially for those genes where complete protein loss results in embryonic lethality. Over the past decade, several transgenic knockdown models have been generated by expressing short hairpin RNA (shRNA), or artificial microRNA (amiRNA) to undertake gene dose effect studies[1,2,3]. In such knockdown models, the target sequences against RNA interference (RNAi) are designed as complementary strands so that they bind to mRNA for its degradation or inhibit translation.

Knockdown mice expressing shRNA or amiRNA are generated by injection of a transgenic cassette into the pronucleus of zygotes[4,5,6], which then gets inserted into the genome randomly, or by embryonic stem (ES) cell-based methods that target the transgene of a specific locus in the genome[7,8]. The former method often causes variegated transgene expression due to reasons such as local effects of the integration site, transgene silencing, adverse effects due to multiple integration sites, and/or multiple tandem transgene insertions. Although the ES cell-targeting approach can overcome such pitfalls, this method is laborious, time-consuming, and cost-prohibitive. Additionally, in both the strategies, a typical transgenic construct constitutes several kilobase pair (kbp) sequence of various elements such as, a suitable promoter, amiRNA sequence often coupled with a reporter gene and a polyA signal.

Endogenous miRNAs are often contained within the introns of protein-coding genes. The intronic miRNAs are co-expressed along with the host genes. The presence of miRNA in an intron does not seem to affect the expression of the host gene, unlike those situated in the 3' untranslated regions (3' UTRs) of genes[9]. Thus, we anticipate that knockdown mice can be obtained by insertion of amiRNA sequence into the intronic regions of an endogenous gene, without affecting expression of the host gene. If such a strategy (of inserting amiRNA into intronic regions) indeed results in reliable knockdown, it could provide numerous intronic sites in the genome to serve as choices for targeted insertion of amiRNA sequences.

The CRISPR/Cas9 system has emerged as a method of choice to rapidly edit the genomes of cells and organisms using the Non-Homologous End-Joining (NHEJ) pathway or the Homology-Directed Repair (HDR) pathway[10,11]. The HDR pathway is used for inserting DNA of interest (DOI) at the cut site by co-introducing repair-template DNA either as single-stranded DNA (ssDNA) or double-stranded DNA (dsDNA). While the ssDNA repair template requires shorter homology arms and is inserted at a very high efficiency, the dsDNA repair template requires long homology arms and is inserted with much lower efficiency[12,13,14]. Due to limitations in the overall length of ssDNA that can be synthesized, the ssDNA repair approach cannot be used to insert longer sequences. The current length limit of commercially synthesizable ssDNA oligonucleotides is up to 200-bases. Further, based on the literature, there are no reports that have used ssDNA longer than 200-bases for targeted modification of the genome.

Here, we utilized a two-step method to synthesize longer ssDNA molecules and demonstrate that they efficiently serve as repair templates for CRISPR/Cas9-mediated knocking-in of sequences. In the first step, RNA was synthesized from a DNA template. In the second step, reverse transcription of the RNA was performed to generate ssDNA. We synthesized ssDNA coding for amiRNA sequences against exogenous (eGFP) and endogenous [orthodenticle homeobox 2 (Otx2)] genes and used them as repair templates in CRISPR/Cas9-mediated knocking-in experiments. We demonstrate that ssDNA templates encoding amiRNA sequences were inserted at high efficiency into intron 6 of eukaryotic translation elongation factor 2 (eEF-2), which resulted in successful knockdown of the genes. By combining the Cre-loxP system with this approach, we also demonstrate that the inserted amiRNA sequences can be conditionally expressed. Furthermore, unlike the complex designs essential in random- or the ES cell-based targeted transgenesis approaches, this system enables the use of shorter, less complex amiRNA knockdown transgenic cassettes. The lengths of ssDNA sequences ranged from 296 to 514-bases. Thus, sequences up to 514-bases can be readily synthesized by the method we described here and they can serve as HDR templates to create knock-in mutations using the CRISPR/Cas9 system.

Results

Preparation of ssDNA.

Figure 1:
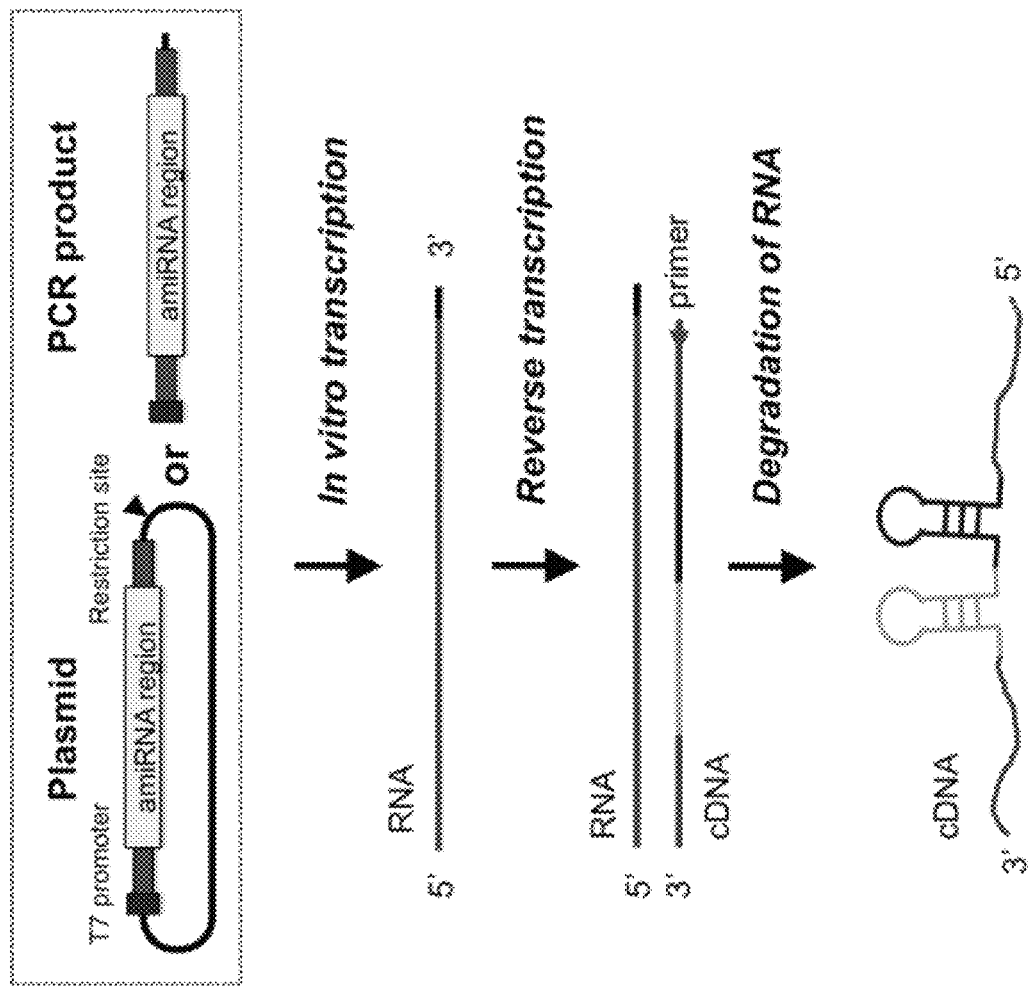
FIG. 1 shows ssDNA synthesis by the ivTRT ("in vitro Transcription and Reverse Transcription") strategy. Schematic of plasmid or PCR product templates showing elements such as T7 promoter (purple) and amiRNA fragment flanked by 3' and 5' homologous sequences to the target (55-bp each, green), used for in vitro transcription of RNA. Plasmid templates are linearized by digesting with a suitable restriction enzyme. In vitro transcription is performed using T7 promoter and T7 RNA polymerase. cDNA (ssDNA) is synthesized by reverse transcription and the RNA template is degraded by RNaseH.

We hypothesized that similar to single-stranded oligo-based short sequence insertions, longer ssDNA can insert at a higher efficiency if such longer ssDNA can be synthesized and supplied as repair templates in CRISPR/Cas9 experiments. Because commercially available ssDNA synthesis methods can generate oligonucleotides of only up to 200-bases, we employed an alternative strategy to synthesize longer ssDNA molecules to use them as repair templates. For this purpose, DNA templates transcribed into RNA were first created; then, the RNA was reverse transcribed back to generate ssDNA molecules. We termed this method "in vitro Transcription and Reverse Transcription (ivTRT)". The DNA templates were either PCR products or plasmids that contained a T7 promoter, an amiRNA region, and short homology arms for targeted insertion (FIG. 1). Approximately 100 to 500 ng (for PCR product) or 1,250 ng (for plasmid) of gel-purified linear DNA templates were used for RNA synthesis in an in vitro transcription reaction. Typical yields ranged from 8 to 18 µg of RNA. Then, 5 µg of RNAs were subjected to cDNA synthesis by reverse transcription reaction. After complete degradation of RNA by RNaseH treatment, resultant cDNA was gel-purified and eluted in microinjection buffer. The yield of cDNAs ranged from 310 to 807 ng that were sufficient for CRISPR/Cas9 injections as the final concentration used for microinjection was 14-20 ng/µl.

Targeted insertion of amiRNA sequence against eGFP into intronic regions of eEF-2 gene. We aimed to insert the amiRNA sequences at a genomic site that would readily allow transgene expression without inhibitory positional effects that occur in certain chromosomal locations. Introns of eukaryotic translation elongation factor 2 (eEF-2) gene were selected as candidates because eEF-2 is expressed at high levels ubiquitously and consistently both during developmental and adult stages[15]. The corresponding intronic regions of mouse and human eEF-2 genes were aligned and compared, which revealed that parts of mouse introns 1 and 6 were among the evolutionarily non-conserved regions. We reasoned that such non-conserved regions are less likely to contain regulatory sequences and therefore not have biological functions. The two less conserved intronic regions in eEF-2 gene were named Target Site 1 and 2 (TS1 and TS2) (FIG. 2a, FIG. 5a). The sgRNAs were designed against TS1 and TS2, as described in Methods section, to insert amiRNA cassettes into these sites. As a first model to test this, we inserted amiRNA to knockdown eGFP gene, using our previously generated eGFP Tg mouse model that shows highly stable eGFP expression[16,17]. The 434-base ssDNA copies for TS1 and TS2, containing amiR-eGFP123/419, were prepared and used as repair DNAs (20 ng/µl) in microinjections that contained Cas9 mRNA (10 ng/µl) and respective CRISPR sgRNAs (10 ng/µl). These injection experiments for TS1 and TS2 were designated as Exp. 1 and Exp. 2, respectively. The zygotes used for injection were obtained by in vitro fertilization of eggs collected from wild-type C57BL/6 mice using sperm collected from homozygous eGFP Tg mice. Injected zygotes were transferred to oviducts of pseudo-pregnant mice and allowed to develop until embryonic day 13.5 (E13.5), when they were collected and examined for eGFP fluorescence.

Embryos exhibiting low eGFP fluorescence were obtained from both Exp. 1 and Exp. 2, suggesting that the amiRNA sequences effectively knocked down eGFP expression (FIG. 2b, FIG. 5b). Genotyping analyses by PCR to detect insertion of amiRNA sequences at the target sites correlated well with the diminished eGFP expression (FIG. 2c, FIG. 5c). The insertion efficiency was 50.0% (3/6) and 83.3% (5/6) for Exp. 1 (into TS1) and Exp. 2 (into TS2), respectively (FIG. 2d, FIG. 5d). Surprisingly, amiR-eGFP were inserted at both the alleles in Exp. 2 (samples #2, #5 and #6), although the sizes of PCR fragments in Exp. 2 sample #6 were larger than expected (FIG. 2c). Sequencing revealed that Exp. 2 samples #1, #2, #3, and #5 showed correct insertions, whereas the Exp. 2 sample #6 showed anomalous insertions[18]. This sample had two different alleles; one allele (lower band in FIG. 2c) contained the amiRNA cassette (one copy each of amiR-eGFP123 and amiR-eGFP419) together with a part of the vector sequence. The other allele (upper band in FIG. 2c) contained one copy of the amiR-eGFP123, two copies of amiR-eGFP419, and a part of the vector sequence. Notably, this sample showed near complete loss of eGFP fluorescence, which suggests homozygosity of insertion of amiR-eGFP123-eGFP419 cassette and an extra copy of amiR-eGFP419 (in one of the alleles) may have contributed to more efficient knockdown. However, it is difficult to rule out effect of vector sequences on the expression of the amiRNA cassette. Of note, the PCR-amplified fragments of all the insertion alleles at TS1 region (Exp. 1) showed unexpected sizes (FIG. 5c), and sequencing revealed that all the alleles contained partial insertion of the ssDNA cassettes and/or deletions near the TS1 genomic region [e.g., 154-base pair (bp) deletion in the amiR-eGFP123 region was detected in Exp. 1 sample #3]. This suggests that either the TS1 site is unstable during ssDNA-mediated repair or that possible secondary structures in the homology arm regions of ssDNA repair template may have interfered with the correct insertion of the template.

Targeted insertion of amiRNA sequence against an endogenous gene. We next tested the above strategy to knockdown an endogenous gene, Otx2, which encodes for a homeobox-containing transcription factor involved in craniofacial development (e.g., parts of head, brain, and eye)[19,20]. Because decreased Otx2 levels are closely associated with malformation of the head or eye[21,22,23], identification of knockdown effects can be readily detected by the morphological phenotype.

Based on the results of eGFP knockdown, the TS2 site that showed a better rate of insertion of intact sequences was used as the target site for insertion of amiRNA sequences against Otx2 (FIG. 3a and FIG. 6a). Two different amiRNA target sequences against Otx2 were tested: amiR-Otx2_518 (Exp. 3) and amiR-Otx2_546 (Exp. 4). The ssDNAs for these amiRNA sequences were 296-bases long that were injected at 14 to 20 ng/µl concentration into C57BL/6 zygotes, together with 10 ng/µl of Cas9 mRNA and 10 ng/µl of sgRNA. Injected zygotes were transferred to oviducts of pseudo-pregnant mice. The fetuses were recovered at E14.5 and examined for knockdown phenotypes. We observed putative Otx2 knockdown phenotypes in two of the embryos derived from Exp. 4 that included amiR-Otx2_546 in the injection mix (FIG. 3b). One embryo (Exp. 4 sample #3) exhibited clear reduction in head, eye, and body size. This phenotype partially resembled Otx2 conditional knockout mouse reported by Fossat et al. (2006)[2]. The anophthalmia (lack of both eyes) phenotype was observed in the embryo #6 in Exp. 4. This is similar to the Otx2 hypomorphic ($Otx2^{AA/AA}$) phenotype reported by Bernard et al. (2014)[22]. However, no embryos showing putative Otx2 knockdown phenotypes were obtained from amiR-Otx2_518 injected fetuses (FIG. 6b).

The genotyping revealed that the insertion efficiency was 10.0% (1/10) and 66.7% (4/6) for Exp. 3 and Exp. 4, respectively (FIG. 3c and FIG. 6c). Consistent with the observed phenotypes, amiRNA sequence was inserted into both alleles of eEF-2 intron 6 in the Exp. 4 sample #3 fetus (FIGS. 3b,c). In addition, the Exp. 4 sample #6 embryo that exhibited anophthalmia also contained the expected amiR-Otx2_546 insertion in the genome (FIGS. 3b,c). However, Exp. 4 samples #4 and #5 and Exp. 3 sample #10 fetuses did not exhibit obvious knockdown phenotypes. Sequence analysis revealed that Exp. 4 sample #4 fetus lacked 23-bp nucleotides from the cassette, which included part of the 3' end of the amiRNA sequence that was not thought to be critical for amiRNA processing. On the other hand, Exp. 4 sample #5 and Exp. 3 sample #10 had intact amiR-Otx2. The observation that knockdown did not occur in these fetuses suggests that the amiRNA sequences are inefficient for knockdown and/or low proportion of inserted cells (mosaicism) in these embryos. Sequence analyses of multiple bands appeared in Exp. 4 samples #1 and #2 showed that these bands contained indel mutations and did not contain ssDNA-derived sequences. Taken together, these results indicate that insertion of amiRNA sequence into the eEF-2 intron 6 can cause knockdown of an endogenous gene and result in observable phenotypes.

Targeted insertion of conditional knockdown amiRNA sequences. The constitutive expression of certain amiRNA sequences that leads to embryonic lethality can eventually result in unavailability of a model for further studies[24,25]. A conditional expression strategy offers the best solution in such cases to generate a viable model. Hence, we next tested applicability of Cre-loxP system, a widely used conditional activation system, in our knockdown strategy. For this purpose, mutant loxP sequences JT15 and JIZ 7 were included to flank the amiRNA sequence, as shown in FIG. 4a, and the cassette was placed in the opposite direction to eEF-2 gene orientation. Because of the opposite orientation, the functional amiRNA will not be produced, and the allele will be in the 'off' state (e.g., 'amiRNA-off' allele). After Cre administration, Cre-loxP-mediated recombination occurred between inversely-oriented JT15 and J7Z17[26] that resulted in inversion of amiRNA region to convert the allele to 'on' state ('amiRNA-on' allele), which will allow for expression of functional amiRNA driven by the eEF-2 promoter. Because JT15 and J7Z17 contain mutations within their inverted-repeat regions, the inversion step will be unidirectional and the 'amiRNA-on' state will get locked after Cre recombination[27].

To test this concept, a 514-base long ssDNA was synthesized containing amiRNA against eGFP, along with flanking mutant loxPs and homology regions for targeted integration (FIG. 4a). This ssDNA (20 ng/µl) was injected into zygotes along with Cas9 mRNA (10 ng/pd) and sgRNA (10 ng/pd) (Exp. 5). The zygotes were obtained as described in Exp. 1 and Exp. 2. E14.5 fetuses derived from injected zygotes were recovered and analyzed by PCR to detect insertion of amiRNA sequences at the target sites. Four out of nine embryos that recovered (44.4%) had expected insertion, of which one showed insertion into both alleles (FIGS. 4b,c). Sequence analyses revealed that all four fetuses contained the correct insertion allele (e.g., Exp. 5 sample #8).

To test if the engineered knockdown cassette can undergo conversion from 'amiRNA-off' to 'amiRNA-on' state upon Cre recombination, the iCre expression vector (pAYC) was transfected into fibroblasts isolated from the embryos (Exp. 5 sample #4 as a test sample and sample #6 as negative control) and assessed eGFP expression. The eGFP fluorescence intensities were examined by fluorescence-activated cell sorting (FACS) after culturing transfected cells for nine days, which showed that a moderate reduction of eGFP florescence occurred only in the iCre-transfected cells derived from Exp. 5 sample #4 embryo. In contrast, no florescence reduction was noted in un-transfected control and amiRNA-negative embryo-derived cells (Exp. 5 sample #6; FIG. 4d). Consistent with this result, PCR genotyping using primer set PP119/M412 detected the presence of 'amiRNA-on' allele generated by Cre-loxP-mediated inversion only in the iCre-transfected sample (Exp. 5 sample #4; FIG. 4e).

Discussion

The CRISPR/Cas9 system has emerged as a popular genome editing method because of its technical simplicity. It is used not only for gene disruption, but also for targeted modification using HDR. The ssDNA donors, up to 200-bases long, are used as donors for insertion of short stretches[10]. Because longer ssDNAs (>200-bases long) cannot be commercially synthesized, longer insertions require the use of dsDNAs (plasmid-based constructs). In this study, we synthesized ssDNA donors of about 0.5-kb long, using a technique called ivTRT. The ssDNA donors were then used in CRISPR/Cas9-mediated targeted insertion experiments. We observed up to 83.3% overall insertion efficiency, and up to 50% insertion efficiency in both alleles. Notably, the homology arm lengths in these samples were only 55-bases on each side. These results suggest that ssDNA-based insertion is efficient even though the length of donors was about 0.5-kb. It would be interesting to evaluate this strategy for longer ssDNA molecules of kilobases longer. Considering that in vitro transcription reactions can typically generate over 4- to 5-kb long RNAs, and up to 10-kb long cDNA can be synthesized using certain reverse transcriptase, ivTRT could be used for synthesizing ssDNA of kilobases long.

If indeed our method can be applied for synthesis and insertion of longer ssDNA templates, the method will be very useful for inserting larger expression cassettes such as promoter.cDNAs:termination signals or fusing protein tags (e.g., GFP or Cre preceded by self-cleaving peptidases such as T2A to the 3' end of last codons of genes). See FIG. 9. It will be of interest to systematically assess the efficiencies of ssDNA donors of varying lengths. Longer ssDNAs may require longer homology arms for efficient targeting. However, this is not expected to be the case considering that successful HDR can occur with as few as 50 to 60-bases for ssDNA termini. See FIG. 9. We are currently testing insertion efficiencies of longer ssDNAs generated with ivTRT and also some of the applications described above. It is also likely that secondary structures in certain longer sequences result in lower insertion efficiency and/or inaccurate insertion. Future studies will be able to systematically evaluate such parameters.

Among the total of 14 samples that contained insertion at TS2 site (that includes both eGFP and Otx2 amiRNA cassette insertions), 12 samples (86%) had correctly inserted cassettes and only 2 samples (Exp. 2 sample #6 and Exp. 4 sample #4) contained inaccurate insertions. Exp. 2 sample #6 contained vector-derived sequences in addition to the intact or extra amiRNA sequences. The presence of vector-derived sequences is probably due to incomplete removal of template DNA by DNase treatment after the in vitro transcription reaction during the ssDNA preparation method and the residual dsDNA (that contained vector sequences) may have got inserted at the cut site. We also observed, a 23-bp deletion near the 3' end of amiRNA region in one sample (Exp. 4 sample #4). This could be due to insertion of partially degraded cDNA (lacking 3' downstream of amiRNA region) or loss of the terminal 23 nucleotides of the ssDNA template during insertion. It is likely that this deletion would not have occurred due to incomplete cDNA synthesis because this terminus originated from the primer end. The fact that about 86% (12 out of 14) of the offspring had correctly inserted donor sequences suggest that the ssDNA synthesized through ivTRT method can generate fairly high accuracy insertion of knock-in cassettes using CRISPR/Cas9.

The presence of vector-derived sequences in Exp. 2 sample #6 fetus indicated a possibility that the residual dsDNA (incompletely removed during ssDNA preparation step) could have served as a donor template for double-strand break (DSB) repair. In order to independently test this possibility, dsDNA (supplied as PCR product) was injected and the samples were analyzed for insertion efficiency of dsDNA template. A total of 20% (2/10) zygotes obtained from dsDNA injection showed targeted insertion, while 50% (12/24) of zygotes from ssDNA injection contained insertion allele (FIG. 7). It is noteworthy that dsDNA injection (at 20 ng/µl concentration) caused excessive damage to zygotes compared to ssDNA injection at least in these experimental conditions. We thus conclude that dsDNA-based targeted insertion with short homology arms is also possible, although ssDNA knock-in strategy seems to be more efficient than the dsDNA 20 knock-in strategy. It should be noted that linear dsDNA can readily get inserted at random sites (as a transgene). Therefore, dsDNA will not be an ideal repair template compared to using it as a circular dsDNA or as a linear ssDNA template.

We were skeptical about the suitability of the novel genetic locus (eEF-2), and the intronic targeting approach, for effectiveness of amiRNA-mediated knockdown because the successful expression of inserted amiRNA cassettes would depend on the normal expression of the host gene, and that the insertion event should also not affect the host gene expression. The efficiencies of knockdown of both endogenous (Otx2) and exogenous (eGFP) genes suggest that the eEF-2 locus that we selected is a good choice, and the inronic site insertion offers as a novel strategy. The knockdown effects in fetuses, however, seemed variegated in both the eGFP and Otx2 knockdown, which could be attributed to the insertions being mono-allelic or bi-allelic, and/or mosaic. Indeed, higher knockdown was observed in samples showing bi-allelic insertions of amiRNAs against eGFP as well as Otx2. Although variegations of knockdown effects can get stabilized once the mutations are established by germline transmission, phenotypic variations observed in F0 animals could often provide valuable information considering that there are human diseases that occur due to mosaic somatic mutations[28].

The insertion of cassettes into the intronic sites may affect correct transcription and splicing of the host gene. In order to rule out this possibility, we examined if TS2 site insertions affected splicing of eEF-2 gene in cultured cells. As shown in FIG. 8, the splicing of the eEF-2 gene was intact. Further, we recently 10 generated viable pups that contained conditional amiRNA against Otx2 gene, and these animals did not show any abnormalities (data not shown). Analysis using the GENSCAN Web Server at MIT (http://genes.miLedu/GEN-SCAN.html)[29] was performed to rule out whether intronic insertion of the cassette could affect prediction of splicing events. The results suggested that the modified eEF-2 genomes (obtained in Exp. No. 2, 4 and 5) predicted normal splicing patterns. These results indicate that insertion of amiRNA sequences into the eEF-2 introns did not have any effects on its transcription and splicing. It is likely that other introns (or introns of other genes) may not be similar to the one tested here in terms of their suitability to insert foreign sequences, particularly if they contain any regulatory sequences.

To overcome the limitations associated with constitutive knockdown, such as lack of tissue-specificity or lethality due to RNAi, conditional approaches using Cre-loxP or inducible RNAi using tetracycline have been utilized[24,25]. In a Cre-loxP-based conditional RNAi approach, to prevent generation of constitutively active shRNA, loxP-flanked stuffer sequences were inserted into the shRNA loop or between the promoter and the shRNA[24,25]. In this case, RNAi is induced after Cre-mediated excision of stuffer sequence from the cassette. As an alternative method, Stern et al. (2008) used irreversible inversion strategy with two pairs of mutant loxP sites (lox2272 and lox5171), by which RNAi is induced after inversion of amiRNA from antisense to sense orientation30. We were able to readily adopt the inversion strategy using mutant loxPs (JT15 and J7Z17) in our conditional knockdown approach unlike the floxed stuffer sequence strategy, which cannot be applied here, because the presence of stuffer sequence in the transcription unit may disrupt proper transcription of the host gene. AmiRNA-based knockdown was observed when the iCre-expression vector was introduced into embryonic fibroblast cells prepared from the knock-in fetuses, indicating that conditional activation of the knockdown cassettes inserted at the eEF-2 locus operate as expected. It should be noted that the inversion strategy may not be used in intronic regions that code for overlapping transcripts from the antisense strand.

In conclusion, this study successfully establishes a simple and efficient method of generation of knockdown mice using CRISPR/Cas9 system. To generate donor repair DNA encoding amiRNA sequences, we used ssDNAs synthesized by a simple strategy called ivTRT and achieved a high integration efficiency. We also demonstrate that amiRNA targeted to an intronic site (e.g., intron 6 of eEF-2 gene) confer knockdown effects in fetuses, indicating that this strategy is powerful for rapid and feasible analyses of developmentally important genes. We are currently investigating the heritability of the knockdown phenotype among the animal models generated by this approach. To our knowledge, this is the first report which demonstrates that successful knockdown models can be generated by targeted insertion of amiRNA sequences to intronic sequences. It will be interesting to examine introns of other genes as potential candidates for achieving desired levels of higher/lower expression or even tissue-specific expression of the inserted amiRNA cassette. The method described here does not require construction of complex vectors and can be accomplished through a direct microinjection method, without using the laborious ES cell-based steps. Our method offers a simple, fast, and efficient means to generate knockdown models that are useful for hypomorphic analysis of gene function. Further, this method can be used for insertion of longer stretches of knock-in sequences that cannot be accomplished using commercially synthesized single-stranded oligonucleotides.

Methods

Designing of amiRNA.

The amiRNA sequences for targeting eGFP (eGFP123 and eGFP419) or the Otx2 (Otx2_518 and Otx2_546) gene were designed using BLOCK-iT RNAi designer (Invitrogen, Carlsbad, Calif.). For amiRNA sequences against eGFP, two pre-miRNA sequences (eGFP123 and eGFP419) were assembled in tandem, whereas the amiRNAs against Otx2 were individually tested (either Otx2_518 or Otx2_546).

Synthesis of ssDNA by ivTRT.

The synthetic DNA oligonucleotides (top and bottom; FIG. 5) were heat denatured and annealed prior to cloning into a vector 5 supplied in the "BLOCK-iT Pol II miR RNAi Expression Vector Kit with EmGFP" (Invitrogen, Carlsbad, Calif.). The regions spanning pre-miRNA(s) were amplified by PCR with primer sets containing 55-bases of homology arms (PP109/PP110 for Exp. 1, PP111/PP112 for Exp. 2, Exp. 3 and Exp. 4) using KOD-Plus-Neo DNA polymerase (TOYOBO, Osaka, Japan), and were cloned into SmaI site of pUC119 vector. The regions containing the amiRNA and homology arm sequences were re-amplified from sequence-confirmed clones by PCR (with primer sets: PP123/M272 for Exp. 1, PP125/M322 for Exp. 2 and Exp. 4, PP125/M272 for Exp. 3; FIG. 5) using KOD-Plus-Neo DNA polymerase and the DNA fragments were gel-purified and used as templates for ivTRT. The template for in vitro transcription in Exp. 5 (pP170 containing "T7 promoter-5' homology arm-JT15-amiR-eGFP419-amiR-eGFP123-JTZ17-3' homology arm-NcoI site") was generated by gene synthesis (GENEWIZ, Inc., South Plainfield, N.J.) ligation-based cloning, and used in an in vitro transcription after digestion with NcoI. The RNAs complementary to the DNA fragments were in vitro synthesized with mMESSAGE mMACHINE T7 Ultra transcription kit (Ambion, Austin, Tex.) and purified using MEGAclear kit (Ambion) after DNase treatment as described previously[10]. The cDNAs were reverse transcribed from synthesized RNAs using SuperScriptII Reverse Transcriptase (Invitrogen) using primer (PP124 for TS1 and PP126 for TS2). The cDNAs were gel-purified and the concentrations were measured using a NanoDrop™ 2000. To avoid clogging during microinjection, ssDNAs were filtered by passing through an Ultrafree-MC filter (HV; 0.45 µm pore size; #UFC30HV00; Millipore, Billerica, Mass.).

Preparation of sgRNA and Cas9 mRNA.

sgRNAs against TS1 and TS2 in eEF-2 gene were designed using CRISPR design5,14 and CHOPCHOP31. The sgRNAs listed as highly potential targets in both the programs but not located in the putative branching site in the intron were picked. The templates for sgRNA synthesis were PCR amplified with primer sets (PP105/M939 for TS1, and PP106/M939 for TS2) using pUC57-sgRNA vector (addgene number: #51132)[32] as template. Four hundred ng of gel-purified PCR products were subjected to RNA synthesis with MEGAshortscript™ T7 Kit (Ambion) and DNase treatment followed by purification of mRNA using MEGAclear Kit. XbaI-digested pBGK10 was used as a template for synthesizing Cas9 mRNA. The synthesis and purification of Cas9 mRNA was performed as described for RNA synthesis steps of ssDNA synthesis.

Mice.

The C57BL/6 mice, used as embryo donors for both eGFP and Otx2 knockdown experiments, were obtained from CLEA Japan, Inc. (Tokyo, Japan). eGFP Tg mouse line (B6.Cg-Gt(ROSA)26Sor<tm2.1(CAG-EGFP)Maoh>), used as embryo donor for eGFP knockdown experiments that has a single copy eGFP transgene integrated at the Rosa26 locus, was previously generated in our facility[17]. All mice were maintained in the Center of Genetic Engineering for Human Diseases (CGEHD) animal facility at Tokai University School of Medicine in Japan. All the animal experiments were performed in accordance with institutional guidelines and were approved by The Institutional Animal Care and Use Committee at Tokai University (Permit Number: #143037).

Microinjection into One-Cell Mouse Embryos.

ssDNA, sgRNA and Cas9 mRNA were mixed (at concentrations of 14-20 ng/µl for ssDNA, 10 ng/µl for sgRNA and 10 ng/µl for Cas9 mRNA) and co-injected into both the pronuclei and cytoplasm of fertilized eggs obtained using in vitro fertilization. Fertilized eggs derived from eGFP Tg male and C57BL/6 female for eGFP knockdown and from C57BL/6 male and female for Otx2 knockdown were used. Injected eggs were cultured overnight in KSOM medium at 37° C. with 5% CO2, and resulting two-cell embryos were transferred into the oviducts of pseudo-pregnant ICR females.

Detection of Targeted Insertion of amiRNA Sequences.

The fetuses were isolated from pseudo-pregnant mice at E13.5 or E14.5 that were implanted with injected zygotes. Targeted ssDNA insertion was assessed by observing under a fluorescence microscope (only for eGFP knockdown), PCR-based genotyping, and sequencing. Expression of eGFP fluorescence in fetuses was checked using the Leica M165 FC (Leica, Wetzlar, Germany) with filter sets for GFP. The primer sets used for PCR-based genotyping were as follows: PP113/M412 in Exp. 1; PP119/PP120 in Exp. 2, Exp. 3, Exp. 4 and Exp. 5.

Direct sequencing for some samples was performed using the gel-purified or Exo-SAP-treated PCR products as templates. For some PCR-amplified bands, fragments were cloned into a pUC119 or a TA Cloning vector (TOPO® TA Cloning Kit, Life Technologies), and the insert sequences were determined.

Preparation of Primary Embryonic Fibroblast Cells.

E14.5 fetuses were isolated in sterile conditions and rinsed with phosphate buffered saline (PBS) containing antibiotics. The livers and heads were dissected out and the remaining parts were chopped into small pieces and were digested with 0.1% Trypsin/EDTA for 20 min at 37° C. Culture medium was then added to the samples and were filtered with nylon mesh to obtain well dispersed population of cells. The cells were centrifuged, re-suspended in culture medium, counted and plated on 6 cm culture plate, cultured until they became confluent, trypsinized, centrifuged, re-suspended in cell culture freezing medium with DMSO and frozen at −80° C. for future use.

Cre-loxP Recombination in Primary Fibroblast Cells and FACS Analysis.

The embryonic primary fibroblasts were plated onto 6 cm plates. The cells were electroporated, two days after plating, with a Neon™ transfection system (Invitrogen) according to the manufacturer's recommendation. In each electroporation, $5 \times 10^4$ cells were electroporated with 500 ng iCre-expression plasmid (pAYC) using the following electroporation conditions; 1350 V pulse voltage, 30 ms pulse width and one pulse. After the electroporation, each sample was plated onto a 24-well plate containing culture medium and cultured for 9 days and was subjected to FACS analysis to assess eGFP fluorescence.

Cells were washed twice with PBS and incubated with 0.05% trypsin-EDTA at 37° C. in 5% CO2 incubator for 5 min, culture medium was added to the plates to stop cell dissociation and then passed through a 35-µm mesh filter (BD Biosciences, Franklin Lakes, N.J., USA) for FACS analysis. The cells were subjected to flow cytometry using an LSRFortessa (BD Biosciences) to assess eGFP fluorescence. Data were analyzed using FlowJo software (Tree Star, Inc., Ashland, Oreg., USA) and % cells showing eGFP loss indicative of Cre-induced activation of knockdown was quantified.

The Cre-loxP recombination in the cells was further confirmed by PCR with primer sets: PP119/M412, M412/PP120 and PP119/PP120 using the genomic DNA isolated from them.

REFERENCES FOR EXAMPLE 1

1. Liu, D. et al. Dosage-dependent requirement of BMP type II receptor for maintenance of vascular integrity. *Blood* 110, 1502-1510 (2007).
2. Hickman-Davis, J. M. & Davis, I. C. Transgenic mice. *Paediatr Respir Rev* 7, 49-53 (2006).
3. Mutsaers, A. J. et al. Modeling distinct osteosarcoma subtypes in vivo using Cre:lox and lineage-restricted transgenic shRNA. *Bone* 55, 166-178 (2013).
4. Hasuwa, H., Kaseda, K., Einarsdottir, T. & Okabe, M. Small interfering RNA and gene silencing in transgenic mice and rats. *FEBS Lett* 532, 227-230 (2002).
5. Sarnova, L., Malik, R., Sedlacek, R. & Svoboda, P. Shortcomings of short hairpin RNA-based transgenic RNA interference in mouse oocytes. *J Negat Results Biomed* 9, 8 (2010).
6. Moreno-Maldonado, R. et al. RNAi-mediated knockdown of IKK1 in transgenic mice using a transgenic construct containing the human H1 promoter. *Scientific World Journal* 2014, 193803 (2014).
7. Premsrirut, P. K. et al. A rapid and scalable system for studying gene function in mice using conditional RNA interference. *Cell* 145, 145-158 (2011).
8. Seibler, J. et al. Single copy shRNA configuration for ubiquitous gene knockdown in mice. *Nucleic Acids Res* 33, e67 (2005).
9. Qiu, L., Wang, H., Xia, X., Zhou, H. & Xu, Z. A construct with fluorescent indicators for conditional expression of miRNA. *BMC Biotechnol* 8, 77 (2008).

10. Harms, D. W. et al. Mouse Genome Editing Using the CRISPR/Cas System. *Curr Protoc Hum Genet* 83, 15 17 11-15 17 27 (2014).
11. Seruggia, D. & Montoliu, L. The new CRISPR-Cas system: RNA-guided genome engineering to efficiently produce any desired genetic alteration in animals. *Transgenic Res* 23, 707-716 (2014).
12. Singh, P., Schimenti, J. C. & Bolcun-Filas, E. A Mouse Geneticist's Practical Guide to CRISPR Applications. *Genetics* 199, 1-15 (2015).
13. Yang, H., Wang, H. & Jaenisch, R. Generating genetically modified mice using CRISPR/Cas-mediated genome engineering. *Nat Protoc* 9, 1956-1968 (2014).
14. Ran, F. A. et al. Genome engineering using the CRISPR-Cas9 system. *Nat Protoc* 8, 2281-2308 (2013).
15. Kouadjo, K. E., Nishida, Y., Cadrin-Girard, J. F., Yoshioka, M. & St-Amand, J. Housekeeping and tissue-specific genes in mouse tissues. *BMC Genomics* 8, 127 (2007).
16. Ohtsuka, M. et al. Pronuclear injection-based mouse targeted transgenesis for reproducible and highly efficient transgene expression. *Nucleic Acids Res* 38, e198 (2010).
17. Ohtsuka, M. et al. Fluorescent transgenic mice suitable for multi-color aggregation chimera studies. *Cell Tissue Res* 350, 251-260 (2012).
18. Quadros, R. M., Harms, D. W., Ohtsuka, M. & Gurumurthy, C. B. Insertion of sequences at the original provirus integration site of mouse ROSA26 locus using the CRISPR/Cas9 system. *FEBS Open Bio* 5, 191-197 (2015).
19. Matsuo, I., Kuratani, S., Kimura, C., Takeda, N. & Aizawa, S. Mouse Otx2 functions in the formation and patterning of rostral head. *Genes Dev* 9, 2646-2658 (1995).
20. Beby, F. & Lamonerie, T. The homeobox gene Otx2 in development and disease. *Exp Eye Res* 111, 9-16 (2013).
21. Hide, T. et al. Genetic modifiers of otocephalic phenotypes in Otx2 heterozygous mutant mice. *Development* 129, 4347-4357 (2002).
22. Bernard, C. et al. Graded Otx2 activities demonstrate dose-sensitive eye and retina phenotypes. *Hum Mol Genet* 23, 1742-1753 (2014).
23. Fossat, N., Chatelain, G., Brun, G. & Lamonerie, T. Temporal and spatial delineation of mouse Otx2 functions by conditional self-knockout *EMBO Rep* 7, 824-830 (2006).
24. Podolska, K. & Svoboda, P. Targeting genes in living mammals by RNA interference. *Brief Funct Genomics* 10, 238-247 (2011).
25. Kleinhammer, A., Wurst, W. & Kuhn, R. Gene knockdown in the mouse through RNAi. *Methods Enzymol* 477, 387-414 (2010).
26. Thomson, J. G., Rucker, E. B., 3rd & Piedrahita, J. A. Mutational analysis of loxP sites for efficient Cre-mediated insertion into genomic DNA. *Genesis* 36, 162-167 (2003).
27. Oberdoerffer, P., Otipoby, K. L., Maruyama, M. & Rajewsky, K. Unidirectional Cre-mediated genetic inversion in mice using the mutant loxP pair lox66/lox71. *Nucleic Acids Res* 31, e140 (2003).
28. Fisher, E. M., Lana-Elola, E., Watson, S. D., Vassiliou, G. & Tybulewicz, V. L. New approaches for modelling sporadic genetic disease in the mouse. *Dis Model Mech* 2, 446-453 (2009).
29. Burge, C. & Karlin, S. Prediction of complete gene structures in human genomic DNA. *J Mol Biol* 268, 78-94 (1997).
30. Stern, P. et al. A system for Cre-regulated RNA interference in vivo. *Proc Natl Acad Sci USA* 105, 13895-13900 (2008).
31. Montague, T. G., Cruz, J. M., Gagnon, J. A., Church, G. M. & Valen, E. CHOPCHOP: a CRISPR/Cas9 and TALEN web tool for genome editing. *Nucleic Acids Res* 42, W401-407 (2014).
32. Shen, B. et al. Efficient genome modification by CRISPR-Cas9 nickase with minimal off-target effects. *Nat Methods* 11, 399-402 (2014).

Example 2

Easi-CRISPR; a method to efficiently knock-in long DNA inserts

Abstract

CRISPR/Cas9 technology efficiently produces short insertions or deletions (indels) and it can also achieve targeted insertion of short single-stranded oligonucleotides when they are included as repair templates. Targeting of long inserts using double-stranded DNA templates is, however, inefficient. To overcome this challenge, we developed Easi-CRISPR (Efficient additions with ssDNA inserts-CRISPR). This method uses in vitro synthesized long single-stranded DNAs as repair templates for highly efficient insertion at Cas9 cut sites.

Introduction

The CRISPR/Cas9 system is widely used in many fields of research to create genome-modified cells and organisms. It is routinely used to create short indels (insertions/deletions) via non-homologous end-joining (NHEJ) and also to insert sequence content from short single-stranded oligodeoxynucleotides (ssODNs) via homology directed repair (HDR) into genes of interest. The ssODN repair templates are typically about 100-200 bases long, consisting of a few bases of altered sequence (e.g., point mutations, recombinase recognition sequences, short deletions or insertions of a few bases) flanked by homology arms of about 40-80 bases (1,2). Targeted insertion of longer new sequences (>100 bases) typically employs cloned double-stranded DNA (dsDNA) as the repair template because ssODNs longer than 200 bases cannot be obtained commercially. However, the efficiency of dsDNA template insertion is poor (3). Furthermore, dsDNA templates require homology arms of at least 0.5 kb. The technical constraints of designing and building such custom targeting constructs for each project add limitations to this approach.

Some strategies for increasing the targeting efficiency of donor DNAs include inhibition of NHEJ or enhancing HDR through chemical treatments (4-8). However, such methods are based on perturbation of fundamental DNA repair processes in cells and may be toxic. Non-toxic approaches include the use of circular dsDNA donors with built-in artificial guide sequences that are linearized inside the cell/embryo (9-11). The linearized donor DNA is then inserted at the genomic cut site by cellular ligases. These designs include either micro-homology ends between the cut ends of the genomic DNA and donor DNA, or ssODNs that bind to the two cut ends so that a precise fusion occurs between the donor and genomic DNAs. While these strategies offer better alternatives to those that perturb DNA repair, they too, have limitations, including the need to design special donor plasmids to suit each target site, and the resulting integration of the vector backbone at the target site may occur depending on the experimental design, which leaves a footprint that can confound subsequent use of the allele.

Results

To develop a simpler method suitable for generating many common types of knock-in animal models, we tested a long ssDNA repair template strategy in mice. The rationale was as follows: short ssODN templates (up to 200 bases) are quite efficient in directing insertions at Cas9 cut sites and the same repair-mechanism might be exploited for delivering larger cargo if the length of the ssDNA could be extended. We recently demonstrated that ~500 base ssDNAs containing ~400 bases of new sequence flanked by ~55 base homology arms directed efficient targeting of the mouse genome. As analyzed during embryonic stages, 5 out of 6 offspring contained the desired insertion (83% efficiency) (12). In the present study, we tested the suitability of long ssDNA donor templates to direct insertions of up to ~1.6 kb into different loci. The method reported here, termed Easi-CRISPR (Efficient additions with ssDNA inserts-CRISPR; pronounced Easy-CRISPR) can be readily adapted to generate even longer insertions at Cas9 cut sites.

We developed four mouse models using Easi-CRISPR; a ~1 kb reverse tetracycline transactivator (rtTA)-polyA cassette was inserted in-frame immediately after the nitiation codon of Otoa and a ~1.4 kb cassette encoding P2A-Flpo recombinase was inserted immediately before the stop codons of Fgf8, Mafb and Slc26a5. The cassettes were flanked by 72 to 105 bases homologous to the target loci. Long ssDNA donor molecules were synthesized using the IvTRT (in vitro Transcription and Reverse Transcription) method described previously (12), or obtained from commercial sources (single-stranded gBlocks® gene fragments, Integrated DNA Technologies). Schematics of the ssDNA cassettes are shown in FIGS. 11(a), 11(b), FIGS. 12(a), 12(b) and FIGS. 13 to 16.

G0 pups were generated following standard CRISPR/Cas9 mouse genome engineering protocols (13) with some modifications described in the online methods. Details of the microinjections and the results are shown in Table 1. Genotyping of G0 pups using 5' and 3' primers indicated that the overall insertion efficiency at all four loci was 32% (8 out of 25 pups contained the respective insertion cassettes: Table 1). The individual insertion efficiencies, for different genes, ranged from 25% to 66%: Fgf8 and Mafb loci; 25%, Otoa locus; 33% and Slc26a5 locus; 66% (Table 1). Notably, the Fgf8 founder contained bi-allelic insertions of the knock-in cassette (FIG. 11(d)). The fidelity of the insertions, including the junctions, was confirmed by sequencing (FIGS. 11(e), 11(f) and FIGS. 12(e), 12(f)). All targeted animals contained precise insertions, except for one Slc26a5P2A-Flpo founder in which genomic DNA sequence duplications were present at the 3' end (FIG. 12(c)). Some of the founders produced F1 heterozgyous offspring at Mendelian ratios, suggesting that their germline is not mosaic (FIG. 17). Taken together, these results indicate that Easi-CRISPR can insert sequences of ~1 kb or longer at high efficiency and that the technique is reproducible at multiple genomic loci.

TABLE 1

Microinjection Data

| Gene-insertion cassette | ssDNA length Left Arm-Cassette-Right Arm (bases) | Ratio (Cassette Length: Total Length of Homology Arms) | Zygotes injected | Zygotes transferred | Newborn pups | Targeted pups (%) |
|---|---|---|---|---|---|---|
| Otoa-rtTA | 96 + 993 + 98 | 993/194 (5.1:1) | 44 | 38 | 10 | 3 (30%) |
| Fgf8-P2A-Flpo | 105 + 1368 + 98 | 1368/203 (6.7:1) | 22 | 13 | 4 | 1 (25%) |
| Slc26a5-P2A-Flpo | 99 + 1368 + 72 | 1368/171 (8:1) | 28 | 22 | 3 | 2 (66%) |
| Mafb-P2A-Flpo | 85 + 1368 + 96 | 1368/181 (7.5:1) | 58 | 53 | 8 | 2 (25%) |

Many types of knock-in animal models are routinely used in biomedical research. For example, several thousands of knock-in mice were designed to express commonly used protein-coding sequences such as EGFP, Cre, Flp, rtTA, tTA etc. Notably, the majority of such cassettes are about 1 to 1.5 kb long. The research community still depends on the lengthy embryonic stem cell-based approaches to develop these types of mouse models because the currently used CRISPR/Cas9-based strategies are inefficient for inserting long dsDNAs. Knocking-in such cassettes can now be rapidly accomplished in mouse embryos using the Easi-CRISPR method described here and similar techniques could be adapted to generate knock-ins in other species. Easi-CRISPR could also be adapted to replace long segments of genomic DNA by making two cuts in the genome. This would facilitate creation of multiple point mutations within an extended stretch of genomic sequence and generation of conditional knock-out (CKO) animals carrying two LoxP sites flanking a target exon (floxing). Given the simple design requirements for the donor DNA (addition of 50 to 100 base homology arms to a dsDNA cassette) and the high efficiency of Easi-CRISPR (25 to 66% efficiency as demonstrated at four different genomic loci), this method would be a simple and efficient method for developing many of the commonly used cell and animal models.

Lastly, whilst the mechanism by which ssDNA molecules are used as templates in DNA repair processes is not that well understood, ssDNA-mediated repair mechanisms (14) and the cellular proteins required for such repair processes (15,16) are emerging. In this context, Easi-CRISPR can serve as a tool to interrogate molecular mechanisms of DNA repair by ssDNA donors in embryos.

Methods

CRISPR Reagents

CRISPR guide RNAs were designed using CRISPR.mit.edu and were used as single guide RNAs (sgRNAs, for Otoa) or as annealed 2-part synthetic crRNA and tracrRNA molecules (for Fgf8, Sc26a5 and Mafb) (Alt-R™ CRISPR guide RNAs, Integrated DNA Technologies). The sgRNA was transcribed from a template generated by annealing two primers using the HiScribe™ T7 Quick High Yield RNA Synthesis Kit (New England Biolabs) following manufacturer's instructions. Cas9 mRNA was prepared using the pBGK plasmid as described in Harms et al., 2014. The plasmid was linearized with XbaI, gel purified and used as the template for in vitro transcription using the mMESSAGE mMACHINE T7 ULTRA kit (Ambion: AM 1345). Cas9 protein was obtained from IDT (Alt-R™ S.p. Cas9 Nuclease 3NLS). Single-stranded DNA Donors were prepared using the IvTRT method described previously (12) or obtained from Integrated DNA Technologies.

Microinjection of One-Cell Embryos

C57BL/6 mice at 3-4 weeks of age (Charles River Laboratories) were superovulated by intraperitoneal injection of 5 IU pregnant mare serum gonadotropin, followed 48 hours later by injection of 5 IU human chorionic gonadotropin (both hormones from National Hormone & Peptide Program, NIDDK). Mouse zygotes were obtained by mating C57Bl/6 stud males with superovulated C57BL/6 females. One-cell stage fertilized mouse embryos were injected with 20 ng/µl Cas9 protein (or, 10 ng/µl of Cas9 mRNA; for Otoa locus), 20 ng/µl of annealed crRNA and tracrRNA (or, 10 ng/µl of each sgRNA; for Otoa locus) and 5-10 ng/µl of ssDNA HDR templates. Both cytoplasmic and pronuclear injections were performed. The surviving embryos were surgically implanted into pseudo-pregnant CD-1 females.

Mouse Genomic DNA Extraction, Genotyping and Sequencing

Mouse genomic DNA was extracted from toe samples using the Qiagen Gentra Puregene Tissue Kit. Primers were designed to amplify the target region. Genomic DNA was subjected to flanking primer PCR and internal (donor oligo-specific) and external primer PCR. PCR reactions were performed using the Promega Hot start green mix. The assay products were analyzed on a 1% agarose gel. The gel purified PCR bands were subjected to sequencing using one of the PCR primers.

REFERENCES FOR EXAMPLE 2

1. Quadros R M, Harms D W, Ohtsuka M, Gurumurthy C B. Insertion of sequences at the original provirus integration site of mouse ROSA26 locus using the CRISPR/Cas9 system. FEBS Open Bio. 2015; 5:191-7.
2. Inui M, Miyado M, Igarashi M, Tamano M, Kubo A, Yamashita S, et al. Rapid generation of mouse models with defined point mutations by the CRISPR/Cas9 system. Sci Rep [Internet]. 2014 Jun. 23 [cited 2016 Apr. 28]; 4. Available from: http://www.nature.com/articles/srep05396
3. Horii T, Hatada I. Challenges to increasing targeting efficiency in genome engineering. J Reprod Dev. 2016; 62(1):7-9.
4. Maruyama T, Dougan S K, Truttmann M C, Bilate A M, Ingram J R, Ploegh H L. Increasing the efficiency of precise genome editing with CRISPR-Cas9 by inhibition of nonhomologous end joining. Nat Biotechnol. 2015 Mar. 23; 33(5):538-42.
5. Yang D, Scavuzzo M A, Chmielowiec J, Sharp R, Bajic A, Borowiak M. Enrichment of G2/M cell cycle phase in human pluripotent stem cells enhances HDR-mediated gene repair with customizable endonucleases. Sci Rep. 2016 Feb. 18; 6:21264.
6. Nakao H, Harada T, Nakao K, Kiyonari H, Inoue K, Furuta Y, et al. A possible aid in targeted insertion of large DNA elements by CRISPR/Cas in mouse zygotes. Genes N Y N 2000. 2016 February; 54(2):65-77.
7. Lin S, Staahl B T, Alla R K, Doudna J A. Enhanced homology-directed human genome engineering by controlled timing of CRISPR/Cas9 delivery. eLife [Internet]. 2014 Dec. 15 [cited 2016 Mar. 12]; 3. Available from: http://elifesciences.org/lookup/doi/10.7554/eLife.04766
8. Chu V T, Weber T, Wefers B, Wurst W, Sander S, Rajewsky K, et al. Increasing the efficiency of homology-directed repair for CRISPR-Cas9-induced precise gene editing in mammalian cells. Nat Biotechnol. 2015 Mar. 24; 33(5):543-8.
9. Yoshimi K, Kunihiro Y, Kaneko T, Nagahora H, Voigt B, Mashimo T. ssODN-mediated knock-in with CRISPR-Cas for large genomic regions in zygotes. Nat Commun. 2016; 7:10431.
10. Nakade S, Tsubota T, Sakane Y, Kume S, Sakamoto N, Obara M, et al. Microhomology-mediated end-joining-dependent integration of donor DNA in cells and animals using TALENs and CRISPR/Cas9. Nat Commun. 2014 Nov. 20; 5:5560.
11. Sakuma T, Nakade S, Sakane Y, Suzuki K-IT, Yamamoto T. MMEJ-assisted gene knock-in using TALENs and CRISPR-Cas9 with the PITCh systems. Nat Protoc. 2016 January; 11(1):118-33.
12. Miura H, Gurumurthy C B, Sato T, Sato M, Ohtsuka M. CRISPR/Cas9-based generation of knockdown mice by intronic insertion of artificial microRNA using longer single-stranded DNA. Sci Rep. 2015 Aug. 5; 5:12799.
13. Harms D W, Quadros R M, Seruggia D, Ohtsuka M, Takahashi G, Montoliu L, et al. Mouse Genome Editing Using the CRISPR/Cas System. Curr Protoc Hum Genet Editor Board Jonathan Haines Al. 2014; 83:15.7.1-15.7.27.
14. Richardson C D, Ray G J, DeWitt M A, Curie G L, Corn J E. Enhancing homology-directed genome editing by catalytically active and inactive CRISPR-Cas9 using asymmetric donor DNA. Nat Biotechnol. 2016 Jan. 20; 34(3):339-44.
15. Yuan Y, Britton S, Delteil C, Coates J, Jackson S P, Barboule N, et al. Single-stranded DNA oligomers stimulate error-prone alternative repair of DNA double-strand breaks through hijacking Ku protein. Nucleic Acids Res. 2015 Sep. 8; gkv894.
16. van Schendel R, Roerink S F, Portegijs V, van den Heuvel S, Tijsterman M. Polymerase Θ is a key driver of genome evolution and of CRISPR/Cas9-mediated mutagenesis. Nat Commun. 2015 Jun. 16; 6:7394.

Example 3

Generation of Conditional Knock-Out Mouse Models Using ssDNA

Table 2 displays microinjection data for generation of three conditional knockout animals using distinct ssDNA cassettes that ranged from 532 to 931 bases. Correct insertion of full length cassettes were observed in genes 1 and 3 (7 to 100% efficiency) whereas some of the gene 2 samples only contained partial cassette insertion and they were scored negative (for full length cassette insertion).

TABLE 2

Conditional Knockout Data

| Conditional KO | ssDNA length Left Arm-Cassette-Right Arm (bases) | Ratio (Cassette Length: Total Length of HomologyArms) | Zygotes injected | Zygotes Transferred | Newborn pups | Targeted pups (%) |
|---|---|---|---|---|---|---|
| Gene 1 | 74 + 372 + 86 (532) | 372/160 (2.3:1) | 91 | 81 | 3 | 3 (100%) |
| Gene 2 | 69 + 565 + 78 (712) | 565/147 (3.8:1) | 59 | 56 | 16 | 0% |
| Gene 3 | 112 + 724 + 95 (931) | 724/207 (3.5:1) | 38 | 33 | 14 | 1 (7%) |

Example 4: Transfection of Nuclease-Based DNA Editing Systems

This prophetic example describes the inventors planned experiments to modify DNA in mammalian cells in culture using the CRISPR/Cas9 system and long ssDNA repair templates. Similar protocols can be obtained from companies such as Integrated DNA Technologies (Coralville, Iowa).

The inventors plan to transfect cultured cells, such as common types of mammalian cells, with the CRISPR machinery and long ssDNA repair templates using conventional lipofection reagents. The inventors will deliver to the cells long ssDNA repair templates in addition to a gene-editing ribonuclear protein (RNP) complex that is comprised of the Cas9 protein and two synthetic RNA oligos: a CRISPR targeting RNA (crRNA) duplexed to a trans-activating crRNA (tracrRNA). Alternatively, the cells may already stably or transiently express the Cas9 protein or a single guide RNA may be used instead of the crRNA and tracrRNA.

The inventors will assemble the RNP complex (duplex the RNA oligos and mix with Cas9 protein) using the follow steps. First, each RNA oligo (crRNA and tracrRNA) will be resuspended in Nuclease-Free Buffer at a final concentration of, for example, 100 µM. The two RNA oligos will be mixed in equimolar concentrations in a sterile microcentrifuge tube. For example, the inventors will create a final duplex concentration of 3 µM by combining 3 µL of 100 µM crRNA; 3 µL of 100 µM tracrRNA; 94 µL Nuclease-Free Buffer to final volume of 100 µL. The duplex mixture will be heated at 95° C. for 5 min and then removed from heat and allowed to cool to room temperature (15-25° C.). If needed, the duplexed RNA may be diluted to a working concentration (for example, 3 µM) in Nuclease-Free Buffer.

To add Cas9 protein to the duplex mixture, the inventors will dilute Cas9 protein to a working concentration (for example, 5 µM) in Cas9 Buffer (20 mM HEPES, 150 mM KCl, 5% Glycerol, 1 mM DTI, pH 7.5). For each transfection, the inventors will combine 1.5 pmol of duplexed RNA oligos with 1.5 pmol of Cas9 protein in Opti-MEM™ Media (Thermo Fisher Scientific) to a final volume of 12.5 µL. The RNP mixture will then be incubated at room temperature for 5 min to assemble the RNP complexes.

To add ssDNA repair template, the inventors will add various concentrations of ssDNA repair template to the RNP complex mixture. 1×, 10×, 100×, 1000×, 10,000× or more fold excess of ssDNA repair template will be tested.

To form transfection complexes, the inventors will mix 12.5 uL of RNP+ssDNA repair template; 1.2 uL Lipofectamine RNAiMAX™ Transfection Reagent (Thermo Fisher Scientific); 11.3 uL OptiMEM™ Media to final volume of 25 uL.

The transfection complexes (25 µL) will then be added to cultured cells that have been diluted to 400,000 cells/mL using complete media without antibiotics. The cells will then be incubated in a tissue culture incubator (37° C., 5% CO2) for 48 hr.

The inventors expect that at least some of the cells in the culture will be modified at the target site using the long ssDNA repair template. The modifications will be detected using conventional molecular biology techniques for mutation detection.

Example 5

Engineering HEK293T Cells with Long ssDNA Donor Templates

To evaluate the integration efficiency of long ssDNA donor templates, N- or C-terminal GFP fusion reporters were created (FIG. 18A) using electroporation to deliver *S. pyogenes* Cas9/sgRNA ribonucleoproteins (RNP) and HDR donors into human culture cell lines. Donors containing ~400-600 nt homology arms lead to ~20-40% GFP knock-in in the RAB11A, CLTA and HIST2H2BE loci in HEK293T cells (FIG. 18B). GFP fluorescence matched the expected localization of the targeted proteins, indicating on-target integration (FIG. 18B, bottom panels). To illustrate another application of ssDNA-mediated fluorescent tagging for the study of protein function, we also introduced photoactivatable mEos3.2 into CLTA (clathrin light-chain A) and used STORM super-resolution microscopy to image clathrin-coated pits in endogenously-tagged cells (FIG. 18C).

Example 6

Engineering Immune Cells with Long ssDNA Donor Templates

RNPs and ssDNA templates were electroporated 2 days following initial T cell stimulation. T cells were harvested from their culture vessels and magnetic CD3/CD28 dynabeads were removed by placing cells on a magnet for 2 minutes. Immediately prior to electroporation, de-beaded cells were centrifuged for 10 minutes at 90 g, aspirated, and resuspended in the Lonza electroporation buffer P3 at 20 uL buffer per one million cells.

ssDNA donor templates were made using one of two methods—either a two step selective exonuclease digestion (FIG. 19A) or sequential in-vitro transcription (IVT) and reverse transcription (RT) reaction (FIG. 19B). At 2 days post-electroporation, viability in CD3+ T cells electroporated with only a ssDNA template was higher than those electroporated with only a dsDNA template (FIG. 19C). A ssDNA RAB11A-GFP ssDNA template also showed high efficiency GFP integration similar to dsDNA templates, and maintained high efficiency integrations at higher molar amounts of template, potentially due to increased viability as well as less mass per mole of DNA template (FIG. 19D.

We claim:

1. A method for treating a subject, the method comprising:
   (a) introducing a donor DNA sequence into a target cell to prepare a donor cell for the subject, wherein the donor DNA sequence comprises a single-stranded DNA (ssDNA) donor molecule and wherein the donor DNA sequence does not comprise a nucleic acid that is complementary to the ssDNA donor molecule, the ssDNA donor molecule comprising:
      (i) a 5' homology arm having 100% sequence identity to a target DNA sequence in the target cell;
      (ii) an exogenous sequence; and
      (iii) a 3' homology arm having 100% sequence identity to the target DNA sequence in the target cell,
      wherein the ssDNA donor molecule is between 200 and 2,000 nucleotides in length and
      wherein the ratio of the length of the exogenous sequence to the total length of the 5' homology arm and the 3' homology arm (exogenous sequence length:homology arm length) is between 2:1 and 5:1;
   (b) introducing or expressing a CRISPR/Cas9 nuclease system in the target cell, under conditions wherein the CRISPR/Cas9 nuclease system cuts the target DNA sequence and the ssDNA donor molecule is recombined with the target DNA sequence and replaces the target DNA sequence in the target cell to prepare the donor cell; and
   (c) transplanting the donor cell into the subject.

2. The method of claim 1, wherein the target cell that is utilized to prepare the donor cell is obtained from the subject.

3. The method of claim 1, wherein the target cell that is utilized to prepare the donor cell is exogenous to the subject.

4. The method of claim 1, wherein the donor DNA sequence is exogenous to the subject.

5. The method of claim 1, wherein the method comprises replacing multiple target DNA sequences in the target cell with multiple donor DNA sequences.

6. The method of claim 1, wherein the exogenous sequence encodes a protein product, an RNA product, a DNA regulatory element, or a variant DNA sequence.

7. The method of claim 1, wherein the ssDNA donor molecule is produced by a method comprising:
   (a) transcribing a DNA template encoding a promoter operably linked to nucleotide sequence comprising a 5' homology arm having substantial sequence identity to the target DNA sequence, an exogenous sequence, and a 3' homology arm having substantial sequence identity to the target DNA sequence to produce a RNA transcript,
   (b) synthesizing a ssDNA/RNA duplex by reverse transcription of the RNA transcript, and
   (c) degrading the RNA from the ssDNA/RNA duplex using an RNA-degrading enzyme to produce the ssDNA donor molecule.

8. The method of claim 7, further comprising purifying the ssDNA donor molecule prior to introducing the donor DNA sequence into the target cell.

9. The method of claim 1, wherein introducing a CRISPR/Cas9 nuclease system in the target cell comprises introducing into the target cell a polynucleotide that encodes the CRISPR/Cas9 nuclease system.

10. The method of claim 1, wherein an insertion efficiency of at least 50% is achieved.

11. A method for treating a subject, the method comprising:
    (a) introducing a donor DNA sequence into a target cell to prepare a donor cell for the subject, wherein the donor DNA sequence comprises a single-stranded DNA (ssDNA) donor molecule and wherein the donor DNA sequence does not comprise a nucleic acid that is complementary to the ssDNA donor molecule, the ssDNA donor molecule comprising:
       (i) a 5' homology arm having 100% sequence identity to a target DNA sequence in the target cell;
       (ii) an exogenous sequence; and
       (iii) a 3' homology arm having 100% sequence identity to the target DNA sequence in the target cell,
       wherein the ssDNA donor molecule is between 200 and 2,000 nucleotides in length and the 5' homology arm and 3' homology arm are between 50-150 nucleotides in length, and the length of the exogenous sequence to the total length of the 5' homology arm and the 3' homology arm is between about 1.5:1 and 20:1;
    (b) introducing or expressing a CRISPR/Cas9 nuclease system in the target cell, under conditions wherein the CRISPR/Cas9 nuclease system cuts the target DNA sequence and the ssDNA donor molecule is recombined with the target DNA sequence and replaces the target DNA sequence in the target cell to prepare the donor cell; and
    (c) transplanting the donor cell into the subject.

12. The method of claim 11, wherein the target cell that is utilized to prepare the donor cell is obtained from the subject.

13. The method of claim 11, wherein the target cell that is utilized to prepare the donor cell is exogenous to the subject.

14. The method of claim 11, wherein the donor DNA sequence is exogenous to the subject.

15. The method of claim 11, wherein the method comprises replacing multiple target DNA sequences in the target cell with multiple donor DNA sequences.

16. The method of claim 11, wherein the exogenous sequence encodes a protein product, an RNA product, a DNA regulatory element, or a variant DNA sequence.

17. The method of claim 11, wherein the ssDNA donor molecule is produced by a method comprising:
    (a) transcribing a DNA template encoding a promoter operably linked to nucleotide sequence comprising a 5' homology arm having substantial sequence identity to the target DNA sequence, an exogenous sequence, and a 3' homology arm having substantial sequence identity to the target DNA sequence to produce a RNA transcript,
    (b) synthesizing a ssDNA/RNA duplex by reverse transcription of the RNA transcript, and
    (c) degrading the RNA from the ssDNA/RNA duplex using an RNA-degrading enzyme to produce the ssDNA donor molecule.

18. The method of claim 17, further comprising purifying the ssDNA donor molecule prior to introducing the donor DNA sequence into the target cell.

19. The method of claim 11, wherein introducing the CRISPR-Cas9 nuclease system in the target cell comprises introducing into the target cell a polynucleotide that encodes the CRISPR-Cas9 nuclease system.

* * * * *

UNITED STATES PATENT AND TRADEMARK OFFICE
CERTIFICATE OF CORRECTION

| | |
|---|---|
| PATENT NO. | : 11,549,126 B2 |
| APPLICATION NO. | : 15/828979 |
| DATED | : January 10, 2023 |
| INVENTOR(S) | : Channabasavaiah B. Gurumurthy et al. |

It is certified that error appears in the above-identified patent and that said Letters Patent is hereby corrected as shown below:

In the Specification

Column 6, Line 38, "show shows" should be --show--.

Column 7, Line 41, "510%" should be --$\leq$10%--.

Column 19, Line 37, "$(X)_3N+(CH_2)(CH_3)$" should be --$(X)_3N^+(CH_2)_n(CH_3)$--.

Column 36, Line 27, "$(2006)^2$" should be --$(2006)^{23}$--.

Column 36, Line 67, "JIZ 7" should be --JTZ17--.

Column 37, Line 7, "$J7Z17^{26}$" should be --$JTZ17^{26}$--.

Column 37, Line 11, "J7Z17" should be --JTZ17--.

Column 37, Line 20, "(10ng/pd) and sgRNA (10 ng/pd)" should be --(10ng/µl) and sgRNA (10 ng/µl)--.

Column 38, Line 61, "dsDNA 20 knock-in" should be --dsDNA knock-in--.

Column 39, Line 25, "recently 10 generated" should be --recently generated--.

Column 39, Line 28, "genes.miLedu" should be --genes.mit.edu--.

Column 39, Line 54, "J7Z17" should be --JTZ17--.

Column 40, Line 39, "vector 5 supplied" should be --vector supplied--.

Column 47, Line 9, "Sc26a5" should be --Slc26a5--.

Signed and Sealed this
Thirtieth Day of May, 2023

*Katherine Kelly Vidal*

Katherine Kelly Vidal
*Director of the United States Patent and Trademark Office*

Column 49, Line 38-39, "may 15 already" should be --may already--.

Column 49, Line 60, "DTI" should be --DTT--.

SEQUENCE LISTING

```
<160> NUMBER OF SEQ ID NOS: 5

<210> SEQ ID NO 1
<211> LENGTH: 71
<212> TYPE: DNA
<213> ORGANISM: Artificial Sequence
<220> FEATURE:
<223> OTHER INFORMATION: Synthetic

<400> SEQUENCE: 1
atcctggacc ccatcttcaa ggtgggtaag ctgtggcctt gtgcaaacag gtgttcgacg      60
ccatcatgaa c                                                          71

<210> SEQ ID NO 2
<211> LENGTH: 53
<212> TYPE: DNA
<213> ORGANISM: Artificial Sequence
<220> FEATURE:
<223> OTHER INFORMATION: Synthetic

<400> SEQUENCE: 2
tcacctgtgt gcttgactta actgcaggat gtctcaggga cctaggacgt gct            53

<210> SEQ ID NO 3
<211> LENGTH: 53
<212> TYPE: DNA
<213> ORGANISM: Artificial Sequence
<220> FEATURE:
<223> OTHER INFORMATION: Synthetic

<400> SEQUENCE: 3
acttgggccc cggagccccg ataggcgctc gcccagctcc tccccaccca gcc            53

<210> SEQ ID NO 4
<211> LENGTH: 54
<212> TYPE: DNA
<213> ORGANISM: Artificial Sequence
<220> FEATURE:
<223> OTHER INFORMATION: Synthetic

<400> SEQUENCE: 4
gagcccaatg caccacccac caccccgag gcataaaggc cctgtatggg gttg            54

<210> SEQ ID NO 5
<211> LENGTH: 52
<212> TYPE: DNA
<213> ORGANISM: Artificial Sequence
<220> FEATURE:
<223> OTHER INFORMATION: Synthetic

<400> SEQUENCE: 5
ctctcccctg agttctttct gtgagtcctg gcgggtctga gtcctggcgg gt             52
```